United States Patent
McCaffrey et al.

(10) Patent No.: US 12,104,210 B2
(45) Date of Patent: Oct. 1, 2024

(54) BLOOD RNA BIOMARKERS OF CORONARY ARTERY DISEASE

(71) Applicants: The George Washington University, Washington, DC (US); The St. Laurent Institute, Vancouver, WA (US)

(72) Inventors: Timothy A. McCaffrey, Silver Spring, MD (US); Georges St. Laurent, III, MD (US); Ian Toma, Vienna, VA (US); Richard Katz, Bethesda, MD (US)

(73) Assignees: The George Washington University, Washington, DC (US); The St. Laurent Institute, Vancouver, WA (US)

( * ) Notice: Subject to any disclaimer, the term of this patent is extended or adjusted under 35 U.S.C. 154(b) by 0 days.

(21) Appl. No.: 17/498,417

(22) Filed: Oct. 11, 2021

(65) Prior Publication Data

US 2022/0243273 A1    Aug. 4, 2022

Related U.S. Application Data

(63) Continuation of application No. 15/691,517, filed on Aug. 30, 2017, now abandoned.

(60) Provisional application No. 62/382,668, filed on Sep. 1, 2016.

(51) Int. Cl.
*C12Q 1/6883* (2018.01)
*G01N 33/68* (2006.01)

(52) U.S. Cl.
CPC ....... *C12Q 1/6883* (2013.01); *G01N 33/6893* (2013.01); *C12Q 2600/112* (2013.01); *C12Q 2600/118* (2013.01); *C12Q 2600/158* (2013.01); *G01N 2800/324* (2013.01)

(58) Field of Classification Search
None
See application file for complete search history.

(56) References Cited

U.S. PATENT DOCUMENTS

| | | |
|---|---|---|
| 8,914,240 B2 | 12/2014 | Rosenberg |
| 9,122,777 B2 | 9/2015 | Rosenberg |
| 2002/0015950 A1 | 2/2002 | Jones |
| 2002/0111742 A1 | 8/2002 | Rocke |
| 2002/0164662 A1 | 11/2002 | Hazen |
| 2006/0134635 A1 | 6/2006 | Liew |
| 2007/0054282 A1 | 3/2007 | Liew |
| 2012/0110684 A1 | 5/2012 | Rozet |
| 2012/0173160 A1 | 7/2012 | Chodosh |
| 2013/0196873 A1 | 8/2013 | Wurdinger |
| 2016/0264950 A1 | 9/2016 | Rogers |

FOREIGN PATENT DOCUMENTS

| | | |
|---|---|---|
| RU | 2525510 C1 | 8/2014 |
| WO | WO-2010/045346 A1 | 4/2010 |

OTHER PUBLICATIONS

European Communication for EP Application No. 17768297.8, dated Jan. 28, 2022, 7 pgs.
G. S. Thomas, et al., "A Blood-Based Gene Expression Test for Obstructive Coronary Artery Disease Tested in Symptomatic Nondiabetic Patients Referred for Myocardial Perfusion Imaging The COMPASS Study", Circulation: Cardiovascular Genetics, vol. 6, No. 2, 25 pgs.
M. R. Elashoff, et al., "Development of a Blood-Based Gene Expression Algorithm for Assessment of Obstructive Coronary Artery Disease in Non-Diabetic Patients", National Library of Medicine, BMC Med Genomics, Mar. 2011, 2 pgs.
H. Peng, et al., "The Genome-Side Express Profiling to Predict Competitive Endogenous RNA Network in Hepatocellular Cancer", ScienceDirect, Genomics Data, vol. 4, 2015, pp. 93-95.
International Preliminary Report on Patentability for PCT/US2017/049454, dated Mar. 5, 2019, 38 pgs.
Gu, W. et al., Depletion of Abundant Sequences by Hybridization (DASH): using Cas9 to remove unwanted high-abundance species in sequencing libraries and molecular counting applications, Genome Biology (2016) 17:41, DOI 10.1186/s13059-016-0904-5.
Hasib, L et al., Functional and homeostatic defects of regulatory T cells in patients with coronary artery disease, Journal of internal medicine vol. 279, 1 (2016): 63-77. doi:10.1111/joim.12398.
Klingenberg, Roland et al., Depletion of FOXP3+ regulatory T cells promotes hypercholesterolemia and atherosclerosis, The Journal of clinical investigation vol. 123,3 (2013): 1323-34.doi: 10.1172/JCI63891.
Search Report dated Apr. 22, 2021 for Russian Application No. 2019109212, 3 pages.
Asare, Adam L. et al., "Differential gene expression profiles are dependent upon method of peripheral blood collection and RNA isolation", BMC Genomics, 2008, 9:474, pp. 1-10.
Wu (Journal of pathology 2001 vol. 195 p. 53) (Year: 2001).
Newton et al (Journal of Computational Biology 2001 vol. 8 p. 37) (Year: 2001).
Affymetrix U133 Microarray (gene probes listed on Microarray downloaded Apr. 3, 2019) (Year: 2019).

*Primary Examiner* — Katherine D Salmon
(74) *Attorney, Agent, or Firm* — Blank Rome LLP

(57) ABSTRACT

The present invention discloses a unique panel of gene transcripts down-regulated in patients with coronary artery disease (CAD). Methods and compositions for detecting CAD in patient blood samples are provided.

17 Claims, 5 Drawing Sheets

BLOOD RNA BIOMARKERS OF CORONARY ARTERY DISEASE

CROSS-REFERENCE TO RELATED APPLICATIONS

This application is a continuation application of U.S. patent application Ser. No. 15/691,517, filed on Aug. 30, 2017, which claims the benefit of U.S. Provisional Application No. 62/382,668, filed on Sep. 1, 2016. The entire disclosures of which are incorporated herein by reference.

TECHNICAL FIELD

The invention relates to diagnosing coronary artery disease (CAD) in a patient, the method comprising analyzing blood samples drawn from the patient and determining the levels of a panel of bio-markers indicative of CAD.

BACKGROUND OF THE INVENTION

There are more than a million heart attacks each year, and 2,200 Americans die of heart disease each day, about 1 every 39 seconds. Outward symptoms of coronary artery disease (CAD) are chest pain, typically radiating down the left arm, and shortness of breath (dyspnea) upon exertion. However, chest pain and dyspnea alone are not particularly specific warning signs. In a prospective analysis of patients presenting with chest pain, ultimately, most cases were determined to be musculoskeletal (20%), gastrointestinal reflux disease (GERD) (13%), while CAD was diagnosed in 11% of cases, and the remaining cases were either pulmonary, neurological, or idiopathic. The Framingham risk factors of advancing age, male gender, elevated cholesterol, smoking, and hypertension, are very good predictors of long term risk (30 yr. risk, C statistic=0.803), but they are far less accurate in acute clinical settings at determining whether a person has CAD or not (C statistic=0.667, where 0.5 is random chance). Thus, there is a tremendous need for improvement in the diagnosis of CAD. From the >1 million cardiac catheterizations yearly, 622,000 result in interventions such as stent placement. Despite overt symptoms and other clinical tests, such as stress electrocardiograms, suggestive of CAD, 20-40% of angiograms do not detect any occluded arteries. The American College of Cardiology's Registry, covering 398,978 patients, identified 39.2% of angiograms with less than 20% stenosis. Thus, a blood test for CAD would have the potential to avoid as many as 400,000 needless catheterizations per year. Previously, we've shown that expression profiling of blood can be used to diagnose which patients will reocclude on bare metal stents, and thus are likely to benefit from a drug eluting stent. Thus, it is both feasible and important to extend RNA profiling to the diagnosis of coronary artery disease itself.

Several prior studies using microarrays suggested that there was an RNA signature in blood associated with CAD. However, the agreement between these studies on exactly which transcripts are modulated is quite low. Such discrepancies could have several explanations, but likely arises from the noise created by highly abundant signals, such as globins, which can overwhelm true signals in microarrays, and thus potentially mask true changes of low magnitude. Thus, we have employed a more advanced, single-molecule RNA sequencing (RNAseq) methodology to help identify diagnostic transcripts. Using RNAseq of whole blood RNA, we identify a subset of transcripts that are consistent with the potential role of T regulatory (Treg) cell dysfunction as a correlate of CAD.

BRIEF DESCRIPTION OF THE INVENTION

The invention takes advantage of the fact that up to 40% of patients that undergo coronary catheterization actually do not have meaningful coronary blockage. By comparing the mRNA expression pattern of patients with vs. those without CAD, transcripts associated with CAD (TRACs) were identified. The strength of this model is that blood can be taken prior to the catheterization, and the outcome of the angiography is known within hours, which provides an ideal learning environment for designing a transcriptome-based test. After the coronary angiograms were digitally interpreted by an attending physician, the patients were divided into 3 groups, ≤20% stenosis (low CAD), >20% but <70% stenosis of any vessel (mid CAD), and ≥70% stenosis of any artery (CAD).

Clinical parameters: Patients presenting for non-emergent, non-ST elevation myocardial infarction (non-STEMI) complaints of chest pain, exertional dyspnea, or other symptoms suggestive of CAD were consented for participation in this study under an IRB approved protocol. Essentially all subjects consented to opt-in for biobanking of their blood, DNA/RNA, and DNA/RNA sequence data. Patients admitted for cardiac catheterization had 3 Tempus blood RNA tubes (3 ml each) (ThermoFisher Scientific, Grand Island, NY) collected by venipuncture prior to sedation. Additional tubes were collected for plasma (EDTA) and buffy coat (CPT). After venipuncture, these studies were purely observational and did not alter the clinical treatment in any way. All relevant clinical data, including a complete blood count (CBC), was captured for comparison to the genomic studies.

Prior to cardiac catheterization, cardiac medical histories were performed by medical professionals to determine CAD risk factors, as defined by accepted guidelines. Hypertension was defined as a history of blood pressure ≥140/90 mmHg and/or treatment with anti-hypertensive medications. Diabetes mellitus was defined by fasting glucose of ≥126 mg/dl and/or use of insulin or oral hypoglycemic agents. Dyslipidemia was defined according to National Cholesterol Education Program Adult Treatment Panel III guidelines or by treatment with lipid lowering medication. Current smoking status was defined by active smoking within 3 months of presentation. A family history of CAD was defined as MI or cardiac death in a first-degree relative.

Chest pain was classified according to standard criteria for angina pectoris as described by Min, et al. [(Min et al., Am J Med. 128(8):871 (2015)]. Typical angina includes substernal, jaw, and/or arm pain upon exertion, and which resolves within 15 minutes of rest and/or use of nitroglycerin. Atypical angina involves 2 of these characteristics. Patients with non-anginal chest pain experience 1 or less of these symptoms. Dyspneic patients without chest pain are classified as having typical angina.

From these clinical parameters, the risks were scored according to the method of Min et al., whereby the points accumulated from age, gender, hypertension, diabetes, symptom type (typical/atypical chest pain), family history, and smoking status are compared to an ordinal risk model to predict likelihood of CAD.

Transcriptome profiling: RNA was purified from frozen Tempus-preserved blood samples using Tempus blood isolation columns. After aggressive in-solution DNAse treatment (Turbo™ DNAse, ThermoFisher Scientific), typical RNA yield from 2.5 ml blood averaged ~5 μg, with a BioAnalyzer integrity score >8 (10 is maximal). The DNAse-treated total RNA was depleted of ribosomal RNA (rRNA) by RiboZero (Ambion, ThermoFisher Scientific) leaving ~500 ng of rRNA-depleted RNA. RNA sequencing: For RNAseq, 100 ng of rRNA-depleted RNA was fragmented and analyzed on a Heliscope sequencer (SeqLL, Inc., Woburn, MA). The raw reads, typically 40 million at 38 bp average length, were then computationally aligned to the transcriptome or genome using Helisphere software. The number of reads that align to each transcript was counted, yielding Digital Gene Expression (DGE) on ~77K known transcript isoforms (HG19 build). The raw read count is then adjusted by the size of the transcript, so that long transcripts do not appear more highly expressed than short transcripts, and by the number of total reads per sample, to produce "Reads Per Kilobase of transcript, per Million mapped reads" (RPKM). Thus, RPKM corrects the expression level between samples that have different absolute numbers of reads. Although the present examples were based on SeqLL/ Helicos single molecule sequencing for RNA sequencing and ddPCR (BioRad, Hercules, CA) for quantitation, other methods for determining absolute and relative levels of RNA transcripts including without limitation, direct RNA sequencing methods, amplification-based methods, and hybridization methods are well known to those of ordinary skill in the art. RPKM levels were migrated to GeneSpring GX13 (Agilent, Santa Clara, CA), without additional normalization, to identify transcripts that differ between groups (TRACs).

Comparison of blood RNA preservation/isolation methods: To determine whether TRACs were affected by the type of blood RNA preservation method employed, 3 Tempus and 3 Paxgene tubes (PreAnalytix GmbH, Hombrechtikon, Switzerland) were drawn from subjects at the same time and then RNA was purified according to the manufacturer's protocol. The Paxgene tubes were subjected to an on-column DNAse treatment, as specified by the manufacturer, while Tempus RNA was treated with TurboDNAse prior to analysis. Equal amounts of RNA, quantified by Nanodrop 260/ 280, was reverse transcribed with random hexamers using the iScript RT kit (RNAseH+) (BioRad), and then analyzed with a set of 'invariant' PCR targets (18S ribosomal, beta-actin, GAPDH), targets related principally to lymphocytes (SpiB, CD81, FoxP3), or selected targets related principally to neutrophils (ALPL, DEFA1, IL8RB, IL8, NFkB, cMyc). cDNAs from pooled standard dilutions were included and analyzed by droplet digital PCR (ddPCR) on a BioRad QX200 real-time system using the EvaGreen fluorochrome in duplicate. The abundance of each transcript was expressed relative to one or more 'invariant' transcripts for that sample, as specified.

The present biomarkers have several useful applications in current medical practice. Some embodiments include, but are not limited to:

In one embodiment, the predictive panel and methods disclosed herein can replace or reduce the need for coronary angiography. In a preferred embodiment, the RNA biomarkers, or their protein products would be assessed to determine the likelihood that a patient with one or more symptoms of CAD may need interventional testing by coronary angiography. Because angiography requires light sedation, introduction of catheter to the coronary beds, and the injection of contrast media, there are finite and known risks of complications, and considerable expenses that could be avoided if the patient were at low risk of CAD as determined by the present invention.

In one embodiment, the predictive panel and methods disclosed herein can indicate the need for coronary imaging tests, such as magnetic resonance (MR) angiography, or computed tomography (CT) angiography. In situations where coronary imaging instruments are available, the TRACs described here may be used to predict whether such relatively non-invasive tests as MR angiography, or CT angiography would be justified. While less invasive than angiography, CT involves some radiation exposure to the patient. Both MR and CT angiography can involve the use of tracer compounds that could have adverse consequences. Furthermore, due to the high cost of the instruments, MR and CT are not available in many non-urban areas of the U.S., and worldwide.

In another embodiment, the predictive panels and methods disclosed herein can indicate the need for medical intervention. In a preferred embodiment, the TRAC biomarkers are applied to subjects under routine medical care and considered at elevated risk of CAD, and thus prone to untoward events, such as heart attacks, strokes, and aneurysms. In this embodiment, subjects with one or more known risk factors for CAD, such as hypertension, family history, advanced age, and/or elevated cholesterol, would have blood drawn for a TRAC test and the results used to determine the need for medical intervention. Common drug interventions for early CAD include the use of statins to lower cholesterol, low dose aspirin to reduce vascular inflammation and platelet reactivity, and antihypertensive drugs such as ACE inhibitors, diuretics, or beta-blockers. In some cases, tighter control of blood sugar levels, by diet or drugs, can be important. Common lifestyle changes include weight loss, smoking cessation, dietary changes, reduced stress, and increased exercise.

In still another embodiment, the panels of TRAC biomarkers are used in routine physical examination of patients presenting to their primary care physicians. In such an embodiment, the panel of TRACs could be used to identify patients with early CAD, but that are not aware of their disease progression. In fact, almost half of all deaths from CAD-related events are in persons that were apparently unaware that they had CAD. Once identified, the patient's risks could be mitigated by drug and lifestyle interventions as described above.

In one embodiment the TRAC biomarkers comprising a plurality of the transcripts selected from those listed in Tables 1-8 indicate that the subject has an increased likelihood of having or developing coronary artery disease.

In a preferred embodiment, the TRAC biomarkers are selected from the group comprising AML1, CD3E, CD4, CD25, CTLA4, DGKA, DLG1, ETS1, FOXP3, ICOSLG, IL2RB, IL2RG, IL2RA, IKZF4/Eos, RUNX1, SMYD3, TCF3, TRIM28, and ZAP70.

DETAILED DESCRIPTION OF THE INVENTION

EXAMPLES

Example 1. Description of Biomarkers from Midpoint Analysis and Transcriptome Alignment Clinical parameters: A total of 113 patients were entered into the study, with 1 patient excluded post-consent due to undetected exclusion criteria of heart failure. Thus, 112 patients were available for analysis, and RNAseq was successfully completed on 96 patients. The following example analyzed the RNAseq result of the first 48 patients, as well as the overall clinical parameters of the entire cohort, in order to determine whether the time and expense of RNAseq was justified on the remaining patients.

Clinical prediction model: The accumulated clinical risk factors yielded a range of 5 to 12 points per patient. A receiver-operator curve (ROC) was computed using JROCFIT between the clinical risk prediction compared to a true positive for CAD based on 70% stenosis on angiogram. The fitted ROC curve yielded a C=0.663 with an accuracy of 60.7%, sensitivity of 57.7%, and specificity of 61.6%, for all 112 patients, and similar values of X, Y, Z for the 96 RNAseq+pts. These values are slightly lower than the published values for this model (C=0.71–0.77), possibly due to differences in the threshold for stenosis (50% there vs 70% here), and comparable to a Diamond-Forrester prediction model (C=0.64).

Analytical parameters: The yield of RNA and the number of reads per patient, and per group did not vary systematically. With 16 additional patients failing at various technical quality control steps in RNA sequencing, RNAseq was completed on 96 patients. Most failures occurred at 3 key steps: low yield from RNA purification or ribosomal depletion, inefficient cDNA synthesis, or low yield of reads from RNAseq. Because of the high loss during ribo-depletion (>90%), there was not always adequate RNA to repeat the RNAseq process.

Figure 1:
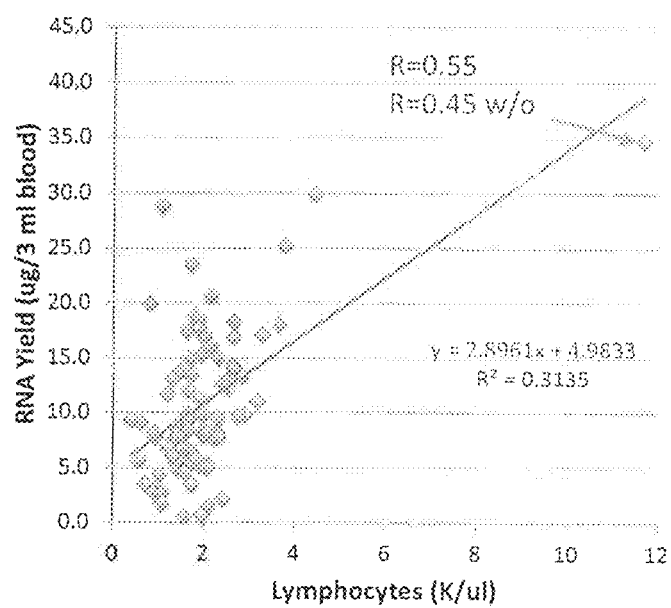
FIG. 1 is a plot of RNA yield per patient (Y axis) in relation to the lymphocyte count in whole blood (X axis).

Sources of variation in RNA yield. Patient blood samples collected with either Paxgene or Tempus RNA preservation tubes show a surprisingly large variation in the RNA yield, with Tempus generally producing higher yield. In the present Tempus-preserved samples, total nucleic acid yield (prior to DNAse treatment) ranged from (0.6-35 µg/3 ml whole blood, mean=10.6 µg). The correlations between RNA yield and any single blood cell count were quite weak, with the strongest correlation to absolute lymphocyte count (r=0.55 with N=112 ($R^2$=0.31) (FIG. 1). While one outlier seems to drive this correlation, it actually has a small impact on the correlation (r=0.45 w/o). This demonstrates that the white cell counts account for only about 30% of the variability in RNA yield, and suggest there may be important differences in the recovery of RNA between patients.

Figure 2:
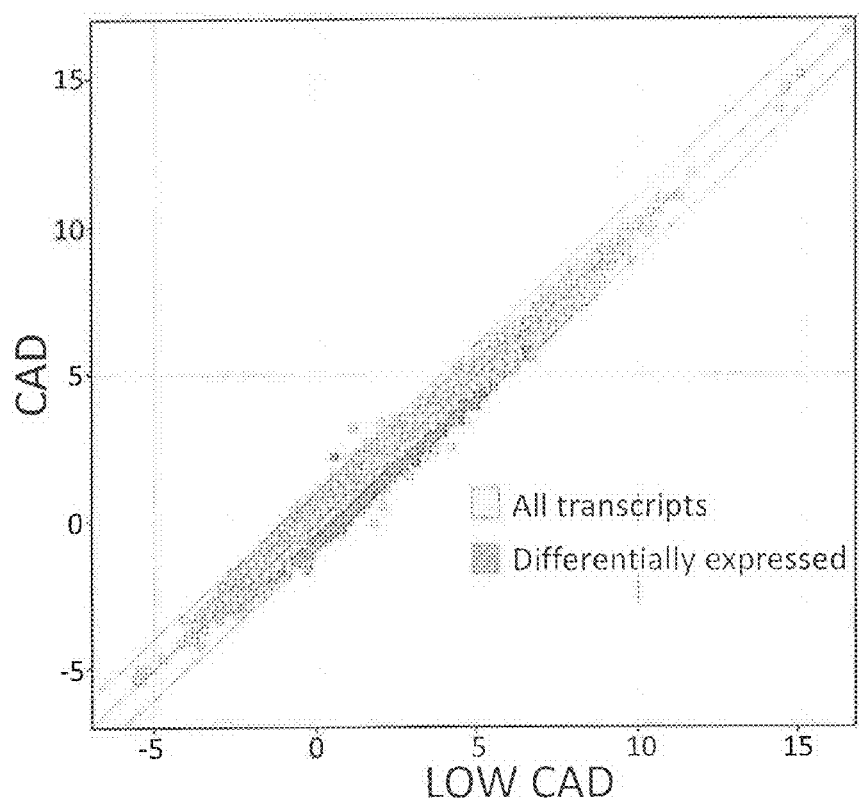
FIG. 2 is a plot of RNAseq linearity with differentially expressed transcripts indicated (dark gray points) relative to all transcripts (light gray points).

Initial identification of TRACs at midpoint: As shown in FIG. 2, there is excellent linear quantitative ability of RNA levels over 25 log 2 orders of magnitude in RPKM without any artificial normalization of the data. To identify TRACs, the patients were divided into LOW (<20% stenosis), MID (20-69%), and HIGH CAD (>70%) groups. To identify differentially expressed transcripts, we compared the LOW vs. the HIGH CAD group, and required a >1.4-fold change and t test p<0.05 uncorrected, resulting in 238 transcripts, highlighted in dark gray in FIG. 2. This combined fold-change/t test strategy has been established in large, multi-center control studies using spiked samples as a reliable approach to identify true differences. The 238 transcript list is presented in Table 1, wherein the relevant transcripts are identified with several different descriptors that are common in the art, especially the UCSC ID (ie uc002rtm.2), maintained by the University of California at Santa Cruz, and the RefSeq ID (ie NM_001113494), maintained by the US National Center for Biotechnology Information (NCBI), as well as the consensus Gene Symbol, and Gene Description.

Classification algorithm: Using ANOVA, we re-analyzed all 3 groups and identified 84 differentially expressed transcripts (Table 2). Using Genespring GX13 software, a Support Vector Machine (SVM) algorithm was built which was 100% sensitive and specific. Leave One Out Cross Validation (LOOCV) applied to the same samples found the model was 87.5% accurate at diagnosing CAD (33.3% is random). For comparison purposes, using the CardioDx transcripts (Elashoff, et al., 2011) to build a comparable SVM yielded only 36.7% accuracy (CAD 37.5%, LOW 45.1%, MID 10%, w/33%=random). This SVM of the CardioDx transcripts, however, does not include the algorithm they employed. For reference, classifying the 48 patients by gender, identified 34 transcripts, mainly from X and Y chromosomes, and yielded an SVM prediction model that was 100% accurate.

Example 2. Description of RNA Biomarkers from Transcriptome Alignment of RNAseq Data from 96 Patients The entire 112 patient cohort was subjected to RNA sequencing using the Helicos (now SeqLL) platform. After RNA purification, ribosomal RNA depletion, and RNA sequencing, it was determined that 96 patient samples were suitable for further analysis.

Discovery and validation sets. Those 96 samples were randomized into a 'Discovery Set' of 45 patients and a 'Validation set' of 51 patients.

Discovery Set. The 45 patients were subdivided into groups according to the degree of CAD as determined upon the same day as blood was drawn for RNAseq. The groups are described above and are composed of LOW (0-20% stenosis), MID (21-69%) and HIGH (≥70%). To identify a relatively small set of biomarkers, with relatively high confidence, the LOW group was compared to the MID+ HIGH groups via a combined T test (p<0.001 uncorrected, and a minimum fold change of 1.5) resulting in 59 transcripts (see Table 3).

A smaller list was constructed of just the top 5 changed transcripts based on both fold-change and a scientific analysis of the transcripts. A PLSD model built on only the 5 transcripts in the DISC group was 84% accurate (91% for LOW, 77% for MID+) (see Table 4).

Because the LOW group includes true 'normals' with essentially 0% stenosis and some patients with small amounts of CAD, we conducted another analysis on the Discovery group that re-arranged the patients by 'normal' (0%) vs 'abnormal' (>0%) and conducted a similar T test yielding 500 transcripts (see Table 5).

Overall prediction models built with the 96 patients. To gain the most powerful model, we included all samples and divided them as in the Discovery/Validation design into LOW vs MID/HIGH (MID+). This yielded 48 patients in each group. Using this design, transcripts were first filtered to exclude transcripts with RPKM<0.01 in 70% of samples, and then TRACs were identified by one-way ANOV of the LOW vs MID+ patients at an uncorrected p value of 0.001, yielding 198 transcripts (see Table 6). These 198 transcripts contain some duplicates that cover essentially the same RNA transcript, yielding 169 non-redundant, unique RNA transcripts.

A PLSD model build on these 198 transcripts was very accurate at a discrimination showing an overall accuracy of 98.9% (100% for LOW, 97.9% for HIGH). This remained fairly robust even with N-fold internal validation yielding overall accuracy of 80% (77% for LOW, 83% for MID+).

Filtering for higher level expression. By filtering the 198 transcripts for those which had a >20$^{th}$ percentile level in both groups, the list was narrowed to 96 transcripts with relatively higher absolute expression than the 198 transcripts. This however, did not improve the predictive ability of the PLSD model built on it, with overall accuracy of 93% (92% for LOW, 94% for MID+), but still produced a quite powerful test, with fewer transcripts (see Table 7).

Identifying a small set of predictive transcripts. To narrow the list even further, the 198 transcripts predictive in the overall cohort were compared for overlap with the transcripts predictive in the DISC set using the LvM+ criteria (Table 3, 59 transcripts). Common to both lists were 14 transcripts that were used to build a new model for the overall cohort. A PLSD model remained powerful with an overall accuracy of 86% (87% for LOW, 85% for MID+) which dropped to 80% overall accuracy in a LOOCV (see Table 8).

Identifying the most comprehensive list of predictive transcripts. For both diagnostic and potential therapeutic uses, there is value in knowing the most comprehensive list of transcripts that might be employed. Thus, by relaxing the ANOVA stringency to p<0.005 (vs. 0.001 in the prior examples), a larger set of 1132 transcripts is identified (see Table 9).

Interpreting the TRAC signature: Both the midpoint and full analysis showed that almost all of the differentially expressed transcripts were down-regulated in the CAD patients, a pattern that rarely occurs in RNA expression analysis, where there is typically a balance between increased and decreased transcripts. Furthermore, the changes are essentially all of the same magnitude (mean=~1.7 fold), while we would normally expect a range of magnitudes. After extensive analysis of the TRACs, the most likely explanation is that TRACs are markers of a particular cell type, and that cell type is reduced in abundance in persons with developing or existing CAD. An extensive literature documents that two relatively selective cell type can be altered in abundance in patients with CAD.

TRACs as markers of a modified population of circulating cells. One way to obtain the uniform decrease in the transcripts is if these transcripts are preferentially associated with a subset of cells, and that subset is reduced in the CAD patients. Certain transcripts identified in the midpoint analysis, such as CCL28, CD2BP2, CD3E, CD5, CD81, KDM2B, LEF1, and MIB2 have been previously associated with various stem and progenitor cell populations. CD81 is interesting because of its well-characterized role in induced pluripotent stem cells (iPSCs), mesenchymal stem cells (MSCs), and hematopoetic stem cells (HSCs).

There is a substantial literature that consistently reports reductions in circulating progenitor cell (CPC) populations in patients with stable CAD or preclinical atherosclerosis. Hypercholesterolemia, smoking and obesity are associated with reduced levels of circulating progenitors. Conversely, circulating endothelial progenitor cells (EPC) are increased in acute MI cases. However, it is unlikely that a decrease in EPC numbers, which are rare (<1%), could cause the substantial shift in RNA levels detected in whole blood. Rather, both EPC decreases and the RNA profile might be two aspects of some larger change in the cellular composition of blood in atherosclerosis.

Figure 3:
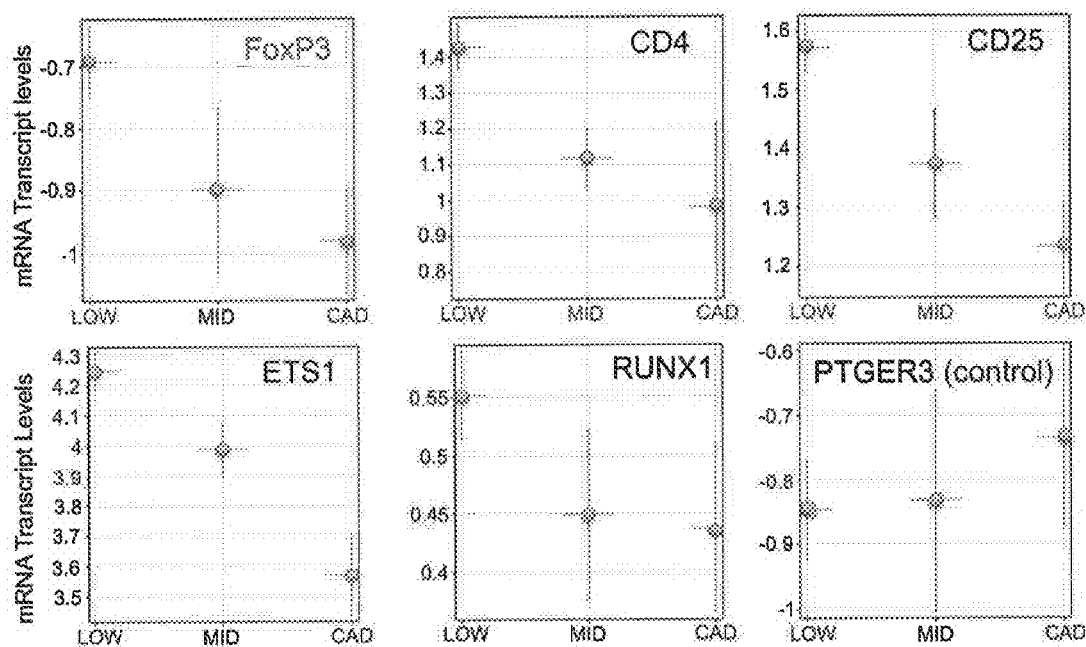
FIG. 3 is a plot of select Treg marker levels (Y axis) in relation to the level of CAD in each of 3 groups (X axis).

TRACs as putative markers of Treg: A second potential explanation for TRACs is that there are known reductions in the T regulatory (Treg) subset of lymphocytes in atherosclerosis. An extensive literature documents reduced Treg abundance, and a relative imbalance in Treg vs T effector (Teff) cells in patients with CAD. To test for the potential changes in Treg, we examined the regulation of known Treg markers in the 3 CAD groups. As shown in FIG. 3, FoxP3, and other markers such as CD4, CD25, ETS1, and RUNX1 mRNA expression levels show a stepwise decrease in expression from LOW, MID, to CAD. By comparison, the expression of an irrelevant marker such as the prostaglandin E receptor 3 (PTGER3) does not show this CAD-related trend.

Treg imbalance is sufficient to create the observed RNA expression pattern. To determine whether a reduction in Treg cell counts in blood would be sufficient in magnitude to produce the observed changes in RNA levels, 8 publications that reported Treg % in normal and CAD patients, such as unstable angina or acute coronary syndrome (ACS), were reviewed and the change in Treg % computed. The average reduction in Tregs, typically defined as CD4+CD25+ CD127low by flow cytometry, was 30.25%, which would translate to a 1.43-fold difference in Treg RNA levels, assuming that these markers are essentially unique to Tregs. Thus, the 1.47-fold reduction in mRNA for the consensus FoxP3 marker is quite consistent with the reported reduction in Treg cell numbers in CAD.

Example 3: Biomarkers Identified by their Relationship to the Treg-Like Pathway

There are not pre-specified pathways or gene ontologies specific to the Treg maturation and differentiation process.

Recent review articles by Li and Rudensky, and others, were adapted to create a functional pathway of Treg signaling to compare with the pattern of RNA changes observed. A striking overlap was observed in the DGEs and known Treg signaling.

Biomarkers of CAD can also be defined by their biological relationship to the Treg pathways and thus we identified a series of markers with known relationship to Tregs differentiation and which varied systemically with CAD status. These include FOXP3, CTLA4, ZAP70 and others (see Table 10).

Using a gene list of just 3 transcripts (FoxP3, Runx1, IL2RA/CD25) associated with relative specificity for Treg cells, but not covered in other TRAC lists, a prediction model was built on the 96 patient cohort whereby 48 subjects are classified as LOW and 48 as MID or HIGH (MID+). Using only these 3 transcripts, a PLSD model showed 60% overall accuracy (67% for LOW, 54% for MID+). However, upon N-fold validation this drops to 46% overall accuracy (47% for LOW, 44% for MID+). This suggests that while the TRACs may be related to Treg numbers or function, the TRACs perform better at predicting CAD than known markers of Treg cells.

Example 4: Prior CAD Prediction Models

Other published and patented works have identified transcripts with predictive value for CAD based on Affymetrix array technology and PaxGene blood RNA preservation tubes (U.S. Pat. Nos. 9,122,777 and 8,914,240, the contents of which are incorporated by reference). Prior studies using microarray profiling of PaxGene preserved blood have led to one blood RNA-based diagnostic (Corus CAD by CardioDx). While the CardioDx test (C=0.745) improves slightly on a purely clinical risk assessment (C=0.732), the present RNAseq test proved to be significantly more accurate (C=0.870). Further, the CorusCAD test by CardioDx uses the age and gender of the subject in calculating their risk score, while the present TRAC method is solely based on gene expression levels.

To compare the methods more directly, we identified 17 best matched transcripts from those patents and publications, without knowledge of the expression levels or predictive values in the current dataset. The expression levels of those 17 CardioDx markers did not differ between Low and MID+ patients in our RNAseq dataset (see Table 11). Nonetheless, we attempted to build a classification model using them, and these 17 transcripts in a PLSD model had 73% overall accuracy (75% for LOW, 71% for MID+), but the accuracy fell to 63.5% in N-fold validation, and 50% would be random chance. Thus, while it is difficult to make an accurate head to head comparison, because they are fundamentally different methods, the present TRAC biomarkers are better at predicting CAD than existing RNA biomarkers.

Example 5: A Small Set of Transcripts with High Predictive Ability

Figure 4:
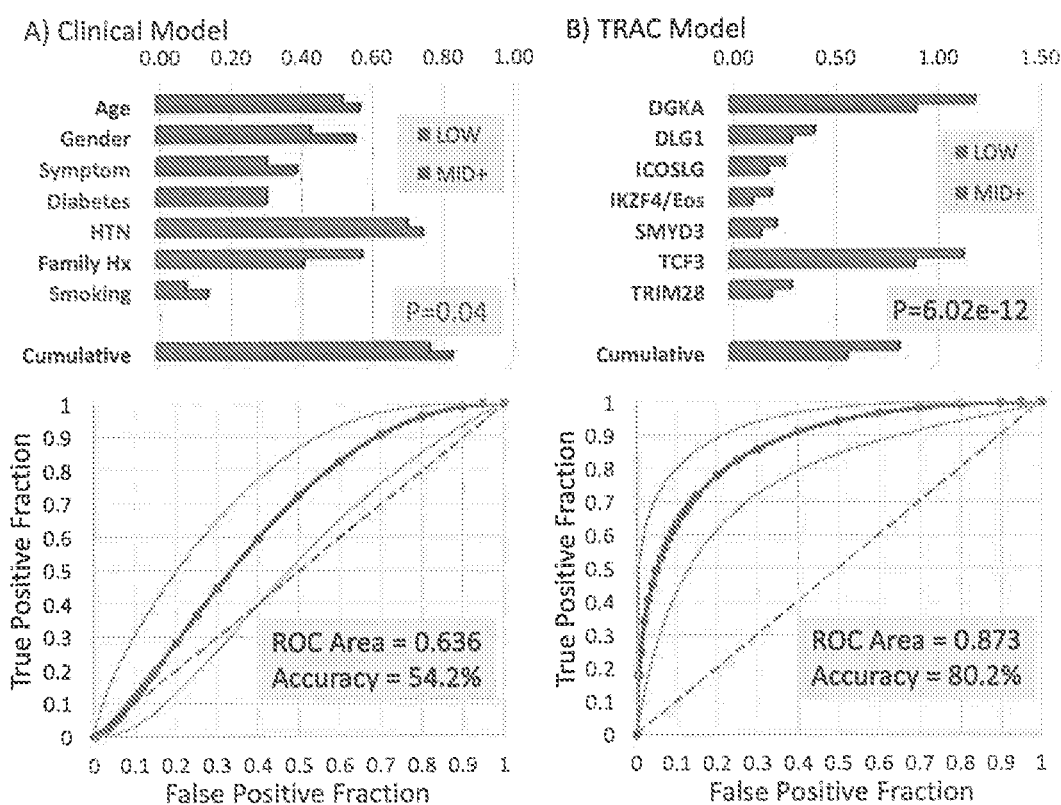
FIG. 4 is a comparison of clinical versus RNA predictors of CAD. Panel A (upper left) shows conventional clinical predictors of CAD plotted for each group, showing Age (decades/10), Gender (% Male), Symptom type (typical/ atypical), Diabetes (%), Hypertension (HTN, %), Family History of CAD (%), and current Smoking (%). A cumulative CAD risk score is calculated for each patient based on the method of Min et al., and divided by 10 for graphic purposes. The relationship between the cumulative risk score and CAD was calculated by the Receiver Operator Characteristic (ROC) and a confusion matrix to identify the accuracy of the method (lower left). Panel B (upper right) shows the performance of 7 RNA transcripts as their gene symbols (i.e. DGKA, DLG1, etc.) expressed as the RPKM by CAD group. A cumulative score was computed expressing each transcript as a ratio to the mean of its expression in the entire group, to prevent highly expressed transcripts from being over-represented. For graphic purposes, the TRIM28 and Cumulative scores are/10. In the lower right panel, the relationship between the cumulative TRAC score (constant-TRAC, to create positive ROC) and angiographically-confirmed CAD is analyzed by ROC similar to the clinical model for the 48 patients in each group

Based upon the medium-sized TRAC lists, specifically Table 6 (198 transcripts, 169 unique), a smaller panel of transcripts was selected based upon specific criteria for their suitability in human diagnostics. These criteria related to the putative association of the transcript with Treg cells, a high level of expression, and relative independence from close gene family members. Using these criteria, 7 transcripts were selected: DLG1, DGKA, ICOSLG, IKZF4/Eos, SMYD3, TCF3, and TRIM28. The levels of these transcripts were extracted from the RNAseq data, expressed as a percentage (ratio) of the mean expression of that transcript in the entire cohort, to minimize overweighting of highly expressed transcripts, and then the normalized levels of the 7 TRACs were added to make a cumulative score, as shown in FIG. 4 (right panel). The classification of the patients into CAD or low CAD was highly accurate (80.2%) based upon this TRAC score alone, with an ROC area (AUC, C-stat) of 0.873. By comparison, using clinical predictors alone, (FIG. 4 left panels), only 54% accuracy (with 50% as random chance) and a C-stat of 0.636 (with 0.500 as random chance) could be achieved.

Example 6: The Effect of Blood RNA Stabilizers on Detection of TRACs

Figure 5:
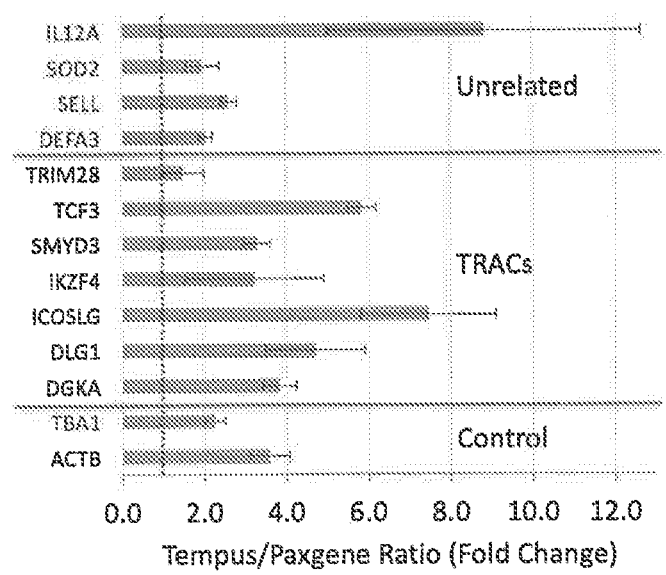
FIG. 5 illustrates the effect of RNA collection/stabilizer solution on expression of TRAC and unrelated transcripts. Whole blood RNA was prepared by two different methods of collection and stabilization from the same donors (n=3). RNA was prepared by PaxGene, which is principally based on a cationic detergent CPC, or Tempus, which is based on the strong denaturant guanidine. Identical quantities of DNAse-treated RNA were reverse transcribed using SuperScript III and then quantitatively amplified using droplet-digital PCR (ddPCR, BioRad). Levels of the transcripts (Y axis) shown are the ratio of transcript abundance in Tempus vs Paxgene (X axis), based on absolute quantities calculated from a Poisson distribution of >20K droplets (+sem).

As discussed, other inventions have described gene panels for CAD that differ completely from the present panels. Those studies employed a preservative for blood RNA called PaxGene, which is based on a cationic detergent, while the present studies employed Tempus preservative, which is based upon guanididium-like denaturants. To determine whether the preservative had an effect on the detection of the TRACs, blood from the same donors were drawn into either PaxGene or Tempus tubes, RNA was prepared by the manufacturer's directions, and then equal amounts of RNA were quantitated by droplet digital PCR, after reverse transcription with iScript (BioRad). The results, shown in FIG. 5, clearly indicate that all of TRACs measured (7) were detected better in the Tempus preservative than in the Paxgene preservative by a range of 1.5 fold (TRIM28) to >7-fold (ICOSLG). Thus, the method of RNA preservation is important to the detection of these TRACs, and the use of differing preservatives may explain some differences between the results.

The accurate diagnosis of CAD via a blood-based test offers several major advantages in clinical medicine. First, it avoids invasive testing, such as cardiac catheterization, as well as allowing more judicious use of imaging resources, such at CT and MR angiography. Secondly, it can improve diagnosis of CAD in rural areas worldwide, where advanced imaging methods are unavailable. Finally, the individual biomarkers within the biomarker panel can serve both as therapeutic targets, and markers to monitor the efficacy of new or existing therapies, such as statins. For instance, Treg numbers have been shown to be responsive to statin therapy, and so it might possible to use TRACs to monitor therapies.

The connection between the immune system and atherosclerosis is well known. Blood components, especially monocytes/macrophages, neutrophils, lymphocytes, and platelets mechanistically contribute to the development of CAD. The present results are consistent with the extensive evidence that CAD is associated with changes in the Treg/Teff ratio, which are thought to be mechanistically related to atherosclerotic progression.

Mechanistically, the present results suggest that changes in the immune system may correlate with the presence of CAD, which has been a substantial line of investigation for many years, progressively building connections between lipid imbalances, inflammation, microbiome changes, and autoimmunity in atherosclerosis. There is a large and fairly consistent literature demonstrating changes in the Treg/Teff ratio in patients with CAD, and those observed cellular changes would be consistent in both direction and magnitude with the current changes in mRNA expression. One interpretation of the beneficial effects of statins is that in addition to lowering LDL cholesterol, statins can induce FoxP3+ Treg cells, via modulation of TGF-ß signaling. Beyond the reproducible clinical correlation, experimental manipulation of Treg levels in mouse models of atherosclerosis lends credence to a potentially causal relationship. Furthermore, it has been suggested that an immune modulatory approach may offer therapeutic potential for atherosclerosis. It is plausible that a stimulatory effect of statins on Treg number could contribute to their anti-atherogenic effect, an effect that has not yet been reported for PCSK9 inhibitors.

An additional relationship can be seen between Treg dysfunction and atherosclerosis through the well-known incidence of atherosclerosis in various autoimmune diseases, but most notably in the case of systemic lupus erythematosus (SLE). While the relationship between Treg and SLE is complex, there is a general consensus that deficient Treg numbers and/or function is one element of SLE, and thus, might also be a component of SLE-associated atherosclerosis. Likewise, psoriasis and psoriatic arthritis, which are associated with Treg imbalances, have well-established associations with atherosclerosis. The immune-CAD connection is further strengthened by an apparently causal relationship in immune-mediated transplant arteriosclerosis.

Potentially the strongest evidence for the immune-CAD connection derives from the proven efficacy of rapamycin, and related compounds which are antibiotics/immunosuppressants, to block restenosis. Rapamycin is known to increase Treg numbers and function at clinically relevant levels.

Many of the TRACs have known relationships with Treg function. Foremost, the forkhead-box transcription factor FoxP3 is considered the definitive marker for the Treg subset, and is thought to transcriptionally regulate a set of transcripts involved in Treg function. FoxP3 is itself epigenetically controlled by promoter demethylation to allow stable expression in Treg, and in turn regulates Treg-specific transcription via known promoter binding sites. Other studies indicate that two isoforms of diacylglycerol kinase (DGKA, DGKZ) have been implicated in T cell anergy, and DGKZ has been implicated in the generation of natural Tregs via modulation of the NFkB signaling through c-rel. The FoxP3 transcription factor is known to interact with Ets transcription factors, and prior work on aortic aneurysm transcript profiling demonstrated that this atherosclerotic condition was associated with coordinated changes in Ets transcription factor-dependent signaling in the aortic tissue. Zap70, the zeta chain associated protein, is preferentially phosphorylated in Treg cells during TCR engagement.

While the underlying cause of the Treg imbalance is currently unknown, there is increasing evidence that changes in the microbiome could alter the type of short-chain fatty acids released into the circulation, thereby modulating both GI and circulating Treg differentiation.

In addition to composing a diagnostic test, it is likely that TRACs can help to elucidate some of the underlying components of CAD, and possibly new targets for therapeutics, in particular, by modulating the Treg/Teff ratio. Through high-throughput screening, dozens of FDA compounds that stimulate Treg generation can be rapidly assessed.

The transcript profile identified here can be adapted to creating a screening test for CAD in asymptomatic individuals, where early detection would allow risk modification and drug therapy. Using microarrays, we've used a similar blood RNA approach to generate new insights into the origin of other cardiovascular diseases, such as adriamycin cardiotoxicity and aspirin resistance (AR), and made the innovative observation that AR is potentially due to an autoimmune antiplatelet syndrome.

There are certain limitations to the present studies: 1) Confounding variables: the TRAC signature could be related to a risk factor or drug treatment that differs between groups. However, based on the clinical variables collected, we cannot identify a co-morbid condition or prescription drug use that would differ sufficiently to create this effect, but it is difficult to completely rule it out. 2) Specificity: It is possible that the TRACs would detect disease in any artery, but even if the test was detecting atherosclerosis in other arteries, it would still have tremendous diagnostic value. The combination of chest pain and a positive TRAC profile in blood would be strong evidence that catheterization, or other follow-up diagnostics, is warranted. Likewise, numbness in the legs, combined with a positive TRAC test, would be sufficient to justify peripheral vascular ultrasound. The Cardiogram group observed that their predictors for CAD also predicted aortic atherosclerosis, suggesting that blood markers are likely to be general predictors of atherosclerosis. Prior work has suggested that the location of atherosclerosis is effectively an endophenotype associated with specific risk factors in a given patient, which one can speculate may be related to the particular autoantigens that are prevalent in particular vascular beds.

TABLE 1

| GeneName | geneSymbol | description | mRNA-Genbank | mRNA-RefSeq |
|---|---|---|---|---|
| uc002jtw.2 | SEPT9 | septin 9 isoform e | NM_001113494 | NM_001113494 |
| uc002rtm.2 | ABCG5 | SubName: Full = ABCG5 protein; SubName: Full = ATP-binding cassette, sub-family G (WHITE), member 5 (Sterolin 1), isoform CRA_a; | BC111541 | NM_022436 |
| uc010pev.1 | ADAM15 | a disintegrin and metalloproteinase domain 15 | AK296925 | NM_207195 |
| uc002zgr.2 | ADARB1 | RNA-specific adenosine deaminase B1 isoform 3 | NM_015834 | NM_015833 |
| uc002lwy.1 | AES | amino-terminal enhancer of split isoform b | NM_001130 | NM_001130 |
| uc0021wz.1 | AES | amino-terminal enhancer of split isoform c | NM_198970 | NM_001130 |
| uc002lxa.1 | AES | amino-terminal enhancer of split isoform b | CR591354 | NM_198969 |
| uc002kqz.1 | AFG3L2 | AFG3 ATPase family gene 3-like 2 | NM_006796 | NM_006796 |
| uc002xai.2 | AHCY | adenosylhomocysteinase isoform 1 | NM_000687 | NM_000687 |
| uc002tsq.1 | PLEKHB2 | cDNA FLJ34479 fis, clone HLUNG2003991. AK091798 | AK091798 | |
| uc002der.3 | PKDIP1 | cDNA FLJ13314 fis, clone OVARC1001506, highly similar to POLYCYSTIN PRECURSOR. | AK126798 | |
| uc001skn.1 | ANKRD33 | ANKRD33 mRNA for ankyrin repeat domain 33, complete cds. | AK098479 | NM_173595 |
| uc002kjk.1 | ARHGDIA | Rho GDP dissociation inhibitor (GDI) alpha | CR619312 | NM_004309 |
| uc002kbp.2 | ARHGDIA | Rho GDP dissociation inhibitor (GDI) alpha | CR590519 | NM_004309 |
| uc002kbq.2 | ARHGDIA | Rho GDP dissociation inhibitor (GDI) alpha | NM_004309 | NM_004309 |

TABLE 1-continued

| GeneName | geneSymbol | description | mRNA-Genbank | mRNA-RefSeq |
|---|---|---|---|---|
| uc003dii.2 | ARHGEF3 | Rho guanine nucleotide exchange factor 3 isoform | AK225688 | NM_019555 |
| uc010owv.1 | ATP1A1 | Na+/K+ -ATPase alpha 1 subunit isoform d | AK296384 | NM_000701 |
| uc003uqm.2 | ATP5J2 | ATP synthase, H+ transporting, mitochondrial F0 | NM_004889 | NM_004889 |
| uc003txt.2 | BC018166 | Homo sapiens, clone IMAGE:3862165, mRNA. | BC018166 | |
| uc011aof.1 | APOBEC3D | SubName: Full = BK150C2.9 protein; SubName: Full = HCG41704, isoform CRA_b; | CU012954 | NM_152426 |
| uc002jsb.1 | SNHG16 | primary hepatoblastoma cDNA, clone:HKMT0728, full insert sequence. | BX647993 | |
| uc002zpk.1 | C22orf39, HIRA | hypothetical protein LOC128977 | NM_173793 | NM_173793 |
| uc002rjf.2 | C2orf28, ATRAID | apoptosis related protein 3 isoform b | NM_080592 | NM_080592 |
| uc004amt.1 | C9orf103 | gluconokinase-like protein | NM_001001551 | NM_001001551 |
| uc010tji.1 | CARKD | SubName: Full = cDNA FUJ52550; | AK296227 | NM_018210 |
| uc011bar.1 | CCDC12 | Coiled-coil domain-containing protein 12; | AK295532 | NM_144716 |
| uc003jnu.2 | CCL28 | chemokine (C-C motif) ligand 28 precursor | NM_148672 | NM_148672 |
| uc002dxr.2 | CD2BP2 | CD2 antigen (cytoplasmic tail) binding protein | NR_024465 | NR_024465 |
| uc001psq.3 | CD3E | CD3E antigen, epsilon polypeptide precursor | NM_000733 | NM_000733 |
| uc009ynk.2 | CD5 | CD5 molecule precursor | NM_014207 | NM_014207 |
| uc001lwg.1 | CD81 | CD81 antigen, tetraspanin family, adhesion | CR622188 | NM_004356 |
| uc004fel.2 | CD99L2 | CD99 antigen-like 2 isoform E3'-E4'-E3-E4 | NM_031462 | NM_031462 |
| uc010wlc.1 | CDK5RAP3 | CDK5 regulatory subunit associated protein 3 | AK300643 | NM_176096 |
| uc003adz.1 | CHEK2 | SubName: Full = CHK2 checkpoint homolog (S. pombe); | CR623156 | NM_007194 |
| uc002mzh.1 | CLEC17A | C-type lectin domain family 17, member A | NM_207390 | NM_207390 |
| uc010xnt.1 | CLEC17A | C-type lectin domain family 17, member A | BC144664 | NM_207390 |
| uc010dzo.1 | CLEC17A | C-type lectin domain family 17, member A | AK127809 | NM_207390 |
| uc002lln.1 | CNDP2 | CNDP dipeptidase 2 | AF258592 | NM_018235 |
| uc001tyn.2 | COQ5 | coenzyme Q5 homolog, methyltransferase | NM_032314 | NM_032314 |
| uc001tyo.2 | COQ5 | coenzyme Q5 homolog, methyltransferase | CR591293 | NM_032314 |
| uc009yrs.1 | CORO1B | coronin, actin binding protein, 1B | CR604899 | NM_020441 |
| uc001nrh.2 | CYBASC3 | cytochrome b, ascorbate dependent 3 isoform 2 | CR600742 | NM 153611 |
| uc010ode.1 | DDOST | dolichyl-diphosphooligosaccharide-protein | AK296041 | NM_005216 |
| uc010twq.1 | DDX24 | DEAD (Asp-Glu-Ala-Asp) box polypeptide 24 | AK297232 | NM_020414 |
| uc009ycf.1 | DEAF1 | deformed epidermal autoregulatory factor 1 | AB209831 | NM_021008 |
| uc001rkk.1 | DENND5B | DENN/MADD domain containing 5B | BC020855 | NM 144973 |
| uc001sij.2 | DGKA | diacylglycerol kinase, alpha 80 kDa | NM_001345 | NM_001345 |
| uc001sik.2 | DGKA | diacylglycerol kinase, alpha 80 kDa | NM_201445 | NM_201445 |
| uc001sim.2 | DGKA | diacylglycerol kinase, alpha 80 kDa | NM_201554 | NM_201554 |
| uc001sin.2 | DGKA | diacylglycerol kinase, alpha 80 kDa | BC031870 | NM_201444 |
| uc009zof.2 | DGKA | Diacylglycerol kinase alpha; | AY930112 | NM_201444 |
| uc010rgq.1 | DGKZ | Diacylglycerol kinase zeta (EC 2.7.1.107); | AK303322 | NM_201533 |
| uc001nck.1 | DGKZ | Diacylglycerol kinase zeta (EC 2.7.1.107); | BX648433 | NM_201533 |
| uc001ncn.1 | DGKZ | diacylglycerol kinase zeta isoform 4 | NM_001105540 | NM_001105540 |
| uc011kzs.1 | DKFZp434C191 | similar to Protein CHMP7. | AK296592 | NM 152272 |
| uc010ybc.1 | DKFZp547H1310 | Carnitine O-palmitoyltransferase I, brain isoform (EC 2.3.1.21); | AK299866 | NM_152359 |
| uc003khn.2 | DKFZp564C0362 | SubName: Full = HSPC116; | CR936787 | NM_012446 |
| uc001ozv.2 | DKFZp686J07132 | SubName: Full = Putative uncharacterized protein DKFZp686J07132; | BX641138 | NM_014488 |
| uc004fek.2 | CD99L2 | cDNA FUJ13714 fis, clone PLACE2000399, weakly similar to T-CELL SURFACE GLYCOPROTEIN E2 PRECURSOR. DKFZp761H2024 | AK125020 | NM_031462 |
| uc001xqv.2 | DLST | dihydrolipoamide S-succinyltransferase (E2 | NM_001933 | NM_001933 |
| uc010tuw.1 | DLSTP | Alpha-ketoglutarate dehydrogenase complex dihydrolipoyl succinyltransferase; | AK299505 | NM_001933 |
| uc002zdj.1 | DQ577420 | H2B histone family, member S, mRNA (cDNA clone IMAGE:8992055). | DQ577420 | |
| uc001zxp.3 | DTWD1 | x 009 protein mRNA, complete cds. | BC018028 | NM_020234 |
| uc011awj.1 | EC45 | RecName: Full = Ribosomal protein L15; | AK293709 | NM_002948 |
| uc002ayn.2 | EDC3 | enhancer of mRNA decapping 3 | NM_001142443 | NM_001142443 |
| uc002ayo.2 | EDC3 | enhancer of mRNA decapping 3 | NM_001142444 | NM_001142444 |
| uc002aym.2 | EDC3 | enhancer of mRNA decapping 3 | NM_025083 | NM_025083 |
| uc010rlw.1 | EEF1G | eukaryotic translation elongation factor 1 | AK300203 | NM_001404 |
| uc001ufm.2 | EIF2B1 | eukaryotic translation initiation factor 2B, | NM_001414 | NM_001414 |
| uc001xrc.1 | EIF2B2 | eukaryotic translation initiation factor 2B, | NM_014239 | NM_014239 |
| uc011amr.1 | EIF3D | eukaryotic translation initiation factor 3 | AK300199 | NM_003753 |
| uc010lbm.2 | EIF4H | eukaryotic translation initiation factor 4H | CR614031 | NM_031992 |
| uc003uaf.1 | EIF4H | Synthetic construct DNA, clone: pF1KA0038, EIF4H gene for eukaryotic translation initiation factor 4H, complete cds, without stop codon, in Flexi system. | CR599953 | NM_031992 |
| uc002xrw.2 | ELMO2 | engulfment and cell motility 2 | BC014207 | NM_182764 |
| uc009yny.1 | EML3 | CDNA FLJ35827 fis, clone TESTI2006453, weakly similar to Microtubule-associated protein like echinoderm EMAP. | AK310579 | NM_153265 |
| uc002piv.2 | EMP3 | epithelial membrane protein 3 | NM_001425 | NM_001425 |
| uc001qej.2 | ETS1 | v-ets erythroblastosis virus E26 oncogene | NM_001143820 | NM_001143820 |
| uc001fqr.2 | ETV3 | ets variant gene 3 isoform 1 | NM_001145312 | NM_001145312 |
| uc001asa.2 | EXOSC10 | exosome component 10 isoform 1 | NM_001001998 | NM_001001998 |
| uc001asb.2 | EXOSC10 | exosome component 10 isoform 2 | NM_002685 | NM_001001998 |
| uc001fke.2 | FDPS | farnesyl diphosphate synthase isoform a | NM_001135821 | NM_001135821 |
| uc002ddj.1 | NPIP | mRNA for FUJ00285 protein. | AK131084 | |

TABLE 1-continued

| GeneName | geneSymbol | description | mRNA-Genbank | mRNA-RefSeq |
|---|---|---|---|---|
| uc010wsi.1 | GALK1 | galactokinase 1 | AK303832 | NM_000154 |
| uc002cxz.1 | GLYR1 | cytokine-like nuclear factor n-pac | BC003693 | NM_032569 |
| uc010uxv.1 | GLYR1 | cytokine-like nuclear factor n-pac | AK296842 | NM_032569 |
| uc002nvf.2 | GPI | glucose phosphate isomerase | AK129884 | NM_000175 |
| uc010xrv.1 | GPI | glucose phosphate isomerase | AK294396 | NM_000175 |
| uc010yma.1 | GPN1 | GPN-loop GTPase 1 isoform c | NM_001145048 | NM_001145048 |
| uc010ymb.1 | GPN1 | GPN-loop GTPase 1 isoform d | NM_001145049 | NM_001145049 |
| uc010ymc.1 | GPN1 | GPN-loop GTPase 1 isoform a | NM_007266 | NM_007266 |
| uc010ymd.1 | GPN1 | GPN-loop GTPase 1 isoform d | NR_026735 | NM_007266 |
| uc001udj.1 | HIP1R | huntingtin interacting protein-1-related | NM_003959 | NM_003959 |
| uc003ngv.2 | HIST1H3D | histone cluster 1, H3d | NM_003530 | NM_003530 |
| uc011hgf.1 | HLA-DPB1 | major histocompatibility complex, class II, DP | L29173 | NM_002121 |
| uc009znj.1 | HNRNPA1 | heterogeneous nuclear ribonucleoprotein A1 | AK308679 | NM_002136 |
| uc002mka.2 | HNRNPM | heterogeneous nuclear ribonucleoprotein M | AB209733 | NM_005968 |
| uc002uui.2 | HSPD1 | chaperonin HSP60 protein 1 | NM_002156 | NM_002156 |
| uc002uuj.2 | HSPD1 | chaperonin | CR619688 | NM_002156 |
| uc010zgx.1 | HSPD1 | chaperonin | AK298632 | NM_002156 |
| uc010rbj.1 | IFP38 | SubName: Full = IFP38; | AK293826 | NM_003754 |
| uc011czk.1 | IK | RED protein | CU687202 | NM_006083 |
| uc003skq.2 | INTS1 | cDNA FUJ36490 fis, clone THYMU2018189. | AX748318 | NM_001080453 |
| uc001lwo.2 | KCNQ1 | potassium voltage-gated channel, KQT-like | NM_181798 | NM_181798 |
| uc001uao.2 | KDM2B | F-box and leucine-rich repeat protein 10 isoform | AK074718 | NM_032590 |
| uc010szx.1 | KDM2B | F-box and leucine-rich repeat protein 10 isoform | AK299827 | NM_032590 |
| uc004dsq.1 | KIAA0312 | mRNA for KIAA0312 gene, partial cds. | BC072421 | NM_031407 |
| uc003dbg.1 | KIAA0800 | mRNA for KIAA0800 protein, partial cds. | BC022792 | NM_014703 |
| uc010hjr.1 | KIAA0890 | mRNA for KIAA0890 protein, partial cds. | AK002076 | NM_138615 |
| uc004dkr.1 | KIAA0901 | SubName: Full = HDAC6 protein; SubName: Full = Histone deacetylase 6; | BC005872 | NM_006044 |
| uc004ckn.1 | KIAA1062 | mRNA for KIAA1062 protein, partial cds. | AL833967 | NM_001606 |
| uc001rfc.2 | LDHB | L-lactate dehydrogenase B | CR612525 | NM_002300 |
| uc003hyw.1 | LEF1 | lymphoid enhancer-binding factor 1, without stop codon, in Flexi system. | AF086339 | NM_001130713 |
| uc003ofe.2 | LEMD2 | LEM domain containing 2 isoform 2 | CR606517 | NM_181336 |
| uc001lht.1 | LHPP | RecName: Full = Phospholysine phosphohistidine inorganic pyrophosphate phosphatase; Short = hLHPP; EC = 3.6.1.1; EC = 3.1.3.-; | BC007324 | NM_022126 |
| uc009yai.1 | LHPP | SubName: Full=Phospholysine phosphohistidine inorganic pyrophosphate phosphatase; | BC073172 | NM_022126 |
| uc002hik.1 | LIG3 | ligase III, DNA, ATP-dependent isoform alpha | NM_013975 | NM_013975 |
| uc002dev.3 | NPIP | hypothetical protein LOC339047 | NM_178541 | NM_178541 |
| uc002dew.3 | LOC339047 | SubName: Full = LOC339047 protein; | BC039707 | NM_178541 |
| uc002dfc.3 | LOC339047 | SubName: Full = LOC339047 protein; | BC039707 | NM_178541 |
| uc002dfd.3 | LOC339047 | hypothetical protein LOC339047 | NM_178541 | NM_178541 |
| uc003huf.3 | METAP1 | methionyl aminopeptidase 1 | NM_015143 | NM_015143 |
| uc010ild.2 | METAP1 | methionine aminopeptidase 1 | AK309465 | NM_015143 |
| uc001wbd.1 | METTL3 | methyltransferase like 3 | CR598589 | NM_019852 |
| uc009vkh.2 | MIB2 | mindbomb homolog 2 | AK097106 | NM_080875 |
| uc001agn.2 | MIB2 | mindbomb homolog 2 | AX747093 | NM_080875 |
| uc009zey.1 | MLF2 | myeloid leukemia factor 2 | AK313998 | NM_005439 |
| uc011aye.1 | MLH1 | MutL protein homolog 1 | AK302807 | NM_000249 |
| uc002ivc.2 | MRPS23 | mitochondrial ribosomal protein S23 | NM_016070 | NM_016070 |
| uc001npd.2 | MS4A6E | membrane-spanning 4-domains, subfamily A, member | NM_139249 | NM_139249 |
| uc003cxg.2 | MST1 | macrophage stimulating 1 (hepatocyte growth | NM_020998 | NM_020998 |
| uc001yqz.1 | MTA1 | metastasis associated protein | BX248755 | NM_004689 |
| uc010ruj.1 | MTMR2 | myotubularin-related protein 2 isoform 2 | AK293243 | NM_201278 |
| uc003phb.3 | MTO1 | mitochondrial translation optimization 1 homolog | BC005808 | NM_133645 |
| uc003hjb.2 | NAAA | N-acylethanolamine acid amidase isoform 1 | NM_014435 | NM_014435 |
| uc001oqp.2 | NADSYN1 | NAD synthetase 1 | AK094022 | NM_018161 |
| uc002tdi.2 | NCK2 | NCK adaptor protein 2 isoform A | NM_001004720 | NM_001004720 |
| uc002och.1 | NFKBID | RecName: Full = NF-kappa-B inhibitor delta; AltName: Full = I-kappa-B-delta; Short = IkappaBdelta; Short = IkB-delta; AltName: Full = IkappaBNS; AltName: Full = T-cell activation NFKB-like protein; AltName: Full = TA-NFKBH; | BC006273 | NM_139239 |
| uc001wjy.2 | NGDN | neuroguidin isoform 1 | NM_001042635 | NM_001042635 |
| uc003bat.2 | NHP2L1 | NHP2 non-histone chromosome protein 2-like 1 | NM_005008 | NM_005008 |
| uc003bau.2 | NHP2L1 | NHP2 non-histone chromosome protein 2-like 1 | CR591470 | NM_005008 |
| uc003bav.2 | NHP2L1 | NHP2 non-histone chromosome protein 2-like 1 | NM_001003796 | NM_001003796 |
| uc003baw.2 | NHP2L1 | NHP2 non-histone chromosome protein 2-like 1 | CR612873 | NM_005008 |
| uc002uwm.2 | NIF3L1 | NIF3 NGG1 interacting factor 3-like 1 isoform 1 | NM_001136039 | NM_001136039 |
| uc003fed.1 | NMD3 | NMD3 homolog | AK094749 | NM_015938 |
| uc003ztb.1 | NOL6 | nucleolar protein family 6 gamma isoform | AF361080 | NM_022917 |
| uc003med.2 | NOP16 | SubName: Full = NOP16 protein; SubName: Full = Putative uncharacterized protein HSPC111; | BC019331 | NM_016391 |
| uc003mee.2 | NOP16 | SubName: Full = NOP16 protein; SubName: Full = Putative uncharacterized protein HSPC111; | BC032424 | NM_016391 |
| uc011dex.1 | NPM1 | nucleophosmin 1 isoform 1 | AY347529 | NM_002520 |
| uc001lfs.2 | NSMCE4A | non-SMC element 4 homolog A | NM_017615 | NM_017615 |

TABLE 1-continued

| GeneName | geneSymbol | description | mRNA-Genbank | mRNA-RefSeq |
|---|---|---|---|---|
| uc003ojl.2 | NUDT3 | nudix-type motif 3 | NM_006703 | NM_006703 |
| uc001ilj.2 | NUDT5 | nudix-type motif 5 | NM_014142 | NM_014142 |
| uc009ysw.1 | NUMA1 | nuclear mitotic apparatus protein 1 | BC008345 | NM_006185 |
| uc001orm.1 | NUMA1 | nuclear mitotic apparatus protein 1 | Z11584 | NM_006185 |
| uc001uap.2 | PCCX2 | PCCX2 mRNA for protein containing CXXC domain 2, partial cds. | AB031230 | NM_032590 |
| uc010uzm.1 | PDXDC1 | pyridoxal-dependent decarboxylase domain | AK299799 | NM_015027 |
| uc002zek.2 | PFKL | RecName: Full = 6-phosphofructokinase, liver type; EC = 2.7.1.11; AltName: Full = Phosphofructokinase 1; AltName: Full = Phosphohexokinase; AltName: Full = Phosphofructo-1-kinase isozyme B; Short = PFK-B; | NR_024108 | NR_024108 |
| uc011cxt.1 | PHF15 | PHD finger protein 15 | AK294327 | NM_015288 |
| uc003kzn.2 | PHF15 | SubName: Full=Putative uncharacterized protein PHF15; | BC012749 | NM_015288 |
| uc004exh.2 | PHF6 | PHD finger protein 6 isoform 2 | NM_032335 | NM_032335 |
| uc010nrr.2 | PHF6 | PHD finger protein 6 isoform 2 | AK290095 | NM_032335 |
| uc003hru.1 | PIGY | phosphatidylinositol glycan anchor biosynthesis, | NM_032906 | NM_001042616 |
| uc010xni.1 | PODNL1 | SubName: Full = cDNA FUJ51218, weakly similar to Mus musculus podocan (Podn), mRNA; | AK296101 | NM_001146254 |
| uc003udl.1 | POM121-2 | POM121-2 mRNA for nuclear pore membrane protein 121-2, partial cds. | BC130589 | NM_001099415 |
| uc002vsc.3 | PTMA | prothymosin, alpha isoform 1 | NM_001099285 | NM_001099285 |
| uc001oli.1 | PTPRCAP | protein tyrosine phosphatase, receptor type, | NM_005608 | NM_005608 |
| uc001goc.2 | QSOX1 | quiescin Q6 sulfhydryl oxidase 1 isoform a | CR601148 | NM_002826 |
| uc009yve.2 | RAB30 | RAB30, member RAS oncogene family | AK291376 | NM_014488 |
| uc001ozu.2 | RAB30 | RAB30, member RAS oncogene family | NM_014488 | NM_014488 |
| uc010rst.1 | RAB30 | RAB30, member RAS oncogene family | AK312233 | NM_014488 |
| uc003dab.1 | RASSF1 | Ras association domain family 1 isoform C | NM 170713 | NM_170713 |
| uc003guz.2 | RHOH | ras homolog gene family, member H precursor | NM_004310 | NM_004310 |
| uc002xux.2 | RNF114 | zinc finger protein 313 | NM_018683 | NM 018683 |
| uc002fzu.2 | RNF167 | ring finger protein 167 precursor | AL834284 | NM_015528 |
| uc001clz.1 | RNF220 | ring finger protein 220 | CR604881 | NM_018150 |
| uc002poa.2 | RPL13a | RecName: Full = Putative 60S ribosomal protein L13a-like MGC87657; | CR596607 | NM_012423 |
| uc010sho.1 | RPL13AP20 | SubName: Full = Ribosomal protein L13a variant; Flags: Fragment; | NR 003932 | NR_003932 |
| uc003ckh.2 | RPL14 | ribosomal protein L14 | NM_001034996 | NM_001034996 |
| uc003ccp.2 | RPL15 | ribosomal protein L15 | CR591026 | NM_002948 |
| uc003mcc.2 | RPL26L1 | ribosomal protein L26-like 1 | NM_016093 | NM_016093 |
| uc003hza.2 | RPL34 | ribosomal protein L34 | NM_033625 | NM_033625 |
| uc002apw.2 | RPL4 | SubName: Full = cDNA FUJ78454, highly similar to ribosomal protein L4 (RPL4), mRNA; SubName: Full = Ribosomal protein L4, isoform CRA_c; SubName: Full = cDNA FUJ78445, highly similar to ribosomal protein L4 (RPL4), mRNA; | CR600936 | NM_000968 |
| uc003zea.2 | RPL8 | SubName: Full = cDNA FUJ76205, highly similar to ribosomal protein L8 (RPL8), transcript variant 1,mRNA; SubName: Full = Ribosomal protein L8, isoform CRA_b; | CR612339 | NM_000973 |
| uc003xsm.2 | RPS20 | ribosomal protein S20 isoform 1 | NM_001146227 | NM_001146227 |
| uc001jzo.2 | RPS24 | ribosomal protein S24 isoform a | CR613997 | NM_001142284 |
| uc010yow.1 | RPS27A | ubiquitin and ribosomal protein S27a precursor | NM_001135592 | NM_001135592 |
| uc010ekw.2 | SAE1 | SUMO1 activating enzyme subunit 1 isoform c | AK027595 | NM_005500 |
| uc002pge.2 | SAE1 | SUMO1 activating enzyme subunit 1 isoform a | NR_027280 | NR_027280 |
| uc001cuq.1 | SCP2 | sterol carrier protein 2 isoform 2 | NM_001007098 | NM_001007098 |
| uc003jao.3 | SDHA | succinate dehydrogenase complex, subunit A, | NM_004168 | NM_004168 |
| uc011clw.1 | SDHA | succinate dehydrogenase complex, subunit A, | AK295937 | NM_004168 |
| uc003jap.3 | SDHA | succinate dehydrogenase complex, subunit A, | CR616767 | NM_004168 |
| uc003zva.3 | SIGMAR1 | sigma non-opioid intracellular receptor 1 | DQ644568 | NM_005866 |
| uc004cpu.2 | SLC25A6 | mRNA for ADP,ATP carrier protein, liver isoform T2 variant protein. | CR619035 | NM_001636 |
| uc004fph.2 | SLC25A6 | mRNA for ADP,ATP carrier protein, liver isoform T2 variant protein. | CR619035 | NM_001636 |
| uc011mml.1 | SLC35A2 | solute carrier family 35, member A2 isoform c | AK293419 | NM_001042498 |
| uc004dlp.1 | SLC35A2 | solute carrier family 35, member A2 isoform c | NM_001042498 | NM_001042498 |
| uc011mmm.1 | SLC35A2 | solute carrier family 35, member A2 isoform c | AK298484 | NM_001042498 |
| uc011mmn.1 | SLC35A2 | solute carrier family 35, member A2 isoform c | AK293415 | NM_001042498 |
| uc004dlr.1 | SLC35A2 | SubName: Full = cDNA FIJ33411 fis, clone BRACE2019467, moderately similar to UDP-GALACTOSE TRANSLOCATOR; | AX746592 | NM_001042498 |
| uc002xro.2 | SLC35C2 | solute carrier family 35, member C2 isoform a | BC025277 | NM_173179 |
| uc001nwd.2 | SLC3A2 CD98 heavy | solute carrier family 3, member 2 isoform c | NM_002394 | NM_002394 |
| uc001nwe.2 | SLC3A2 | solute carrier family 3, member 2 isoform d | NM_001012663 | NM_002394 |
| uc003lyi.1 | SLU7 | step II splicing factor SLU7 mRNA, complete cds. | DQ174516 | NM_006425 |
| uc002psd.2 | SPIB | Spi-B transcription factor (Spi-1/PU.1 related) | NM_003121 | NM_003121 |
| uc003kho.2 | SSBP2 | single-stranded DNA binding protein 2 | NM_012446 | NM_012446 |
| uc003khp.2 | SSBP2 | single-stranded DNA binding protein 2 | AF077048 | NM_012446 |
| uc011ctp.1 | SSBP2 | single-stranded DNA binding protein 2 | AK293544 | NM_012446 |
| uc003frb.2 | ST6GAL1 | ST6 beta-galactosamide | NM_173216 | NM_173216 |

TABLE 1-continued

| GeneName | geneSymbol | description | mRNA-Genbank | mRNA-RefSeq |
|---|---|---|---|---|
| uc003frc.2 | ST6GAL1 | ST6 beta-galactosamide | NM_173217 | NM_173216 |
| uc003frd.2 | ST6GAL1 | ST6 beta-galactosamide | NM_003032 | NM_003032 |
| uc002jbm.2 | STRADA | STE20-related kinase adaptor alpha isoform 1 | NM_001003787 | NM_001003787 |
| uc002jbp.2 | STRADA | STE20-related kinase adaptor alpha isoform 3 | NM_153335 | NM_153335 |
| uc002jbq.2 | STRADA | STE20-related kinase adaptor alpha isoform 4 | CR601658 | NM_001003788 |
| uc003acr.2 | TFIP11 | tuftelin interacting protein 11 | AK025443 | NM_001008697 |
| uc003acs.2 | TFIP11 | tuftelin interacting protein 11 | NM_001008697 | NM_001008697 |
| uc003act.2 | TFIP11 | tuftelin interacting protein 11 | NM_012143 | NM_001008697 |
| uc002euo.2 | THAP11 | THAP domain containing 11 | NM_020457 | NM_020457 |
| uc003gtk.2 | TLR10 | toll-like receptor 10 precursor | NM_001017388 | NM_030956 |
| uc002juj.1 | TMC6 | transmembrane channel-like 6 | AY236496 | NM_007267 |
| uc002jul.1 | TMC6 | transmembrane channel-like 6 | NM_007267 | NM_007267 |
| uc010wtp.1 | TMC6 | SubName: Full = cDNA FUJ55825, highly similar to Transmembrane channel-like protein 6; | AK303165 | NM_007267 |
| uc002gsw.1 | TOP3A | SubName: Full = cDNA FLJ44921 fis, clone BRAMY3011581, highly similar to DNA topoisomerase 3-alpha (EC 5.99.1.2); SubName: Full = cDNA FLJ77764; | AK126869 | NM_004618 |
| uc003bjv.2 | TRABD | TraB domain containing | CR590805 | NM_025204 |
| uc002qth.1 | TRIM28 | tripartite motif-containing 28 protein | AK131063 | NM_005762 |
| uc010gti.1 | UBE2L3 | ubiquitin-conjugating enzyme E2L 3 | CR626405 | NM_003347 |
| uc003sjg.2 | UNC84A | unc-84 homolog A isoform a | BX649069 | NM_001130965 |
| uc011jvr.1 | UNC84A | unc-84 homolog A isoform b | AK304150 | NM_001130965 |
| uc001qrh.3 | USP5 | ubiquitin specific peptidase 5 isoform 2 | NM_003481 | NM_001098536 |
| uc004cea.1 | vWF-CP | vWF-CP(ADAMTS13) mRNA for von Willebrand factor-cleaving protease, complete cds. | BC039251 | NM_139025 |
| uc011bby.1 | WDR6 | WD repeat domain 6 protein | AK297090 | NM_018031 |
| uc010yly.1 | XAB1 | XAB1 mRNA for XPA binding protein 1, complete cds. | AK303566 | NM_032434 |
| uc010yme.1 | XAB1 | SubName: Full = cDNA FUJ61157, highly similar to XPA-binding protein 1; | CR608298 | NM_007266 |
| uc002sye.1 | ZAP70 | zeta-chain associated protein kinase 70kDa | BC039039 | NM_001079 |
| uc010itd.1 | ZDHHC11 | cDNA FUJ13153 fis, clone NT2RP3003409, weakly similar to Human DHHC-domain-containing cysteine-rich protein mRNA. | AK024233 | NM_024786 |
| uc011mlu.1 | ZNF182 | zinc finger protein 21 isoform 2 | AK299325 | NM_001007088 |
| uc011azd.1 | ZNF619 | zinc finger protein 619 isoform 5 | NM_001145083 | NM_001145082 |
| uc010ydi.1 | ZNF836 | zinc finger protein 836 | AK131308 | NM_001102657 |
| uc010ydj.1 | ZNF836 | zinc finger protein 836 | NM_001102657 | NM_001102657 |

TABLE 2

| GeneName | Symbol | Description | GenBank | mRNA-RefSeq |
|---|---|---|---|---|
| uc001ukx.2 | ANKLE2 | ankyrin repeat and LEM domain containing 2 | NM_015114 | NM_015114 |
| uc010glj.2 | APP | amyloid beta A4 protein isoform e precursor | NM_001136129 | NM_001136130 |
| uc009znc.2 | ATP5G2 | ATP synthase, H+ transporting, mitochondrial F0 | AK311357 | NM_001002031 |
| uc001dmq.2 | CCBL2 | kynurenine aminotransferase III isoform 2 | NM_001008662 | NM_001008662 |
| uc004fek.2 | CD99L2 | CD99 antigen-like 2, T-Cell surface glycoprotein E2 precursor | AK125020 | NM_031462 |
| uc002ewt.3 | CIRH1A | cirhin, | BX647265 | NM_032830 |
| uc002tyn.2 | COQ5 | coenzyme Q5 homolog, methyltransferase | NM_032314 | NM_032314 |
| uc001nck.1 | DGKZ | Diacylglycerol kinase zeta (EC 2.7.1.107); | BX648433 | NM_201533 |
| uc010hjr.1 | DHX30 | DEAH box polpeptide 30 | AK002076 | NM_138615 |
| uc010tuw.1 | DLSTP | a-ketoglutarate dehydrogenase, dihydrolipoyl succinyltransferase; | AK299505 | NM_001933 |
| uc010xnr.1 | DNAJB1 | DnaJ (Hsp40) homolog, subfamily B, member 1 | AK301817 | NM_006145 |
| uc001asb.2 | EXOSC10 | exosome component 10; 2, Rrp6p, polymyositis/schleroderma autoantigen | NM_002685 | NM_001001998 |
| uc001zmo.1 | FAM82A2 | family with sequence similarity 82, member A2, PTPIP51 | AK092058 | NM_018145 |
| uc003gzy.2 | FIP1L1 | FIP1 like 1 isoform 1 | NM_030917 | NM_030917 |
| uc001qkz.2 | FKBP4 | FK506 binding protein 52 | NM_002014 | NM_002014 |
| uc010gro.1 | HIRA | HIR histone cell cycle regulation defective | AK289809 | NM_003325 |
| uc002pxi.2 | LET-7E | has-mir-let-7e, low in CAD | AY940866 | |
| uc003huf.3 | METAP1 | methionyl aminopeptidase 1 | NM_015143 | NM_015143 |
| uc003fxb.1 | NCBP2 | nuclear cap binding protein subunit 2, 20 kDa | AK093216 | NM_007362 |
| uc002dlw.2 | NDUFAB1 | NADH dehydrogenase (ubiquinone) 1, alpha/beta | NM_005003 | NM_005003 |
| uc003baw.2 | NHP2L1 | NHP2 non-histone chromosome protein 2-like 1 | CR612873 | NM_005008 |
| uc001lfs.2 | NSMCE4A | non-SMC element 4 homolog A | NM_017615 | NM_017615 |
| uc010uzm.1 | PDXDC1 | pyridoxal-dependent decarboxylase domain | AK299799 | NM_015027 |
| uc003kzl.2 | PHF15 | RecName: Full = Protein Jade-2; AltName: Full = PHD finger protein 1 | AK074123 | NM_015288 |
| uc009yve.2 | RAB30 | RAB30, member RAS oncogene family | AK291376 | NM_014488 |
| uc010hlc.1 | RBM6 | RBM6 protein, RNA binding protein targeted to splicing speckles | AK308794 | NM_005777 |
| uc002xux.2 | RNF114 | zinc finger protein 313 | NM_018683 | NM_018683 |
| uc002fll.2 | RNF166 | FLJ32544 fis, similar to RING finger protein 166; CRA_d; | CR620092 | NM_178841 |
| uc001clz.1 | RNF220 | ring finger protein 220 | CR604881 | NM_018150 |
| uc001dwy.1 | SARS | Seryl-tRNA synthetase, isoform CRA_e; | CR598649 | NM_006513 |
| uc003gdi.1 | SLBP | stem-loop (histone) binding protein | NM_006527 | NM_006527 |
| uc004dlr.1 | SLC35A2 | cDNA FLJ33411 fis, similar to UDP-GALACTOSE TRANSLOCATOR; | AX746592 | NM_001042498 |
| uc010prt.1 | SRGAP2 | SLIT-ROBO Rho GTPase activating protein 2 | AK295845 | NM_001042758 |

TABLE 2-continued

| GeneName | Symbol | Description | GenBank | mRNA-RefSeq |
| --- | --- | --- | --- | --- |
| uc001rxv.1 | TFCP2 | transcription factor CP2, aka LSF, late SV40 factor | AK291264 | NM_005653 |
| uc002euo.2 | THAP11 | THAP domain containing 11 | NM_020457 | NM_020457 |
| uc010onv.1 | TMEM48 | Nucleoporin NDC1; | AK302910 | NM_018087 |
| uc002gsw.1 | TOP3A | DNA topoisomerase 3-alpha (EC 5.99.1.2) | AK126869 | NM_004618 |
| uc002qth.1 | TRIM28 | tripartite motif-containing 28 protein | AK131063 | NM_005762 |
| uc001sqh.2 | TSFM | Ts translation elongation factor, mitochondrial | BC022862 | NM_005726 |
| uc010gti.1 | UBE2L3 | ubiquitin-conjugating enzyme E2L 3 | CR626405 | NM_003347 |
| uc001ucn.2 | ZCCHC8 | zinc finger, CCHC domain containing 8 | NM_017612 | NM_017612 |
| uc002qrs.1 | ZNF274 | zinc finger protein 274 isoform b | NM_016324 | NM_016324 |
| | | Redundant or RPKM less than 1.0 | | |
| uc002rtm.2 | ABCG5 | ABCG5 protein; ATP-binding cassette, G (WHITE), member 5 (Sterolin 1), CRA_a; | BC111541 | NM_022436 |
| uc011acg.1 | APP | amyloid beta A4 protein isoform e precursor | AK295373 | NM_001136130 |
| uc010ccy.1 | ARL2BP | Homo sapiens Arf-like 2 binding protein BART1 mRNA, complete cds. | AK311018 | NM_012106 |
| uc010imf.2 | CCDC109B | coiled-coil domain containing 109B | AK311030 | NM_017918 |
| uc010dzo.1 | CLEC17A | C-type lectin domain family 17, member A | AK127809 | NM_207390 |
| uc002mzh.1 | CLEC17A | C-type lectin domain family 17, member A | NM_207390 | NM_207390 |
| uc010szj.1 | COQ5 | FLJ55122,Ubiquinone biosynthesis methyltransferase COQ5, (EC 2.1.1.-); | AK298214 | NM_032314 |
| uc001tyo.2 | COQ5 | coenzyme Q5 homolog, methyltransferase | CR591293 | NM_032314 |
| uc002wrt.1 | CRNKL1 | crooked neck-like 1 protein | AF255443 | NM_016652 |
| uc001ozv.2 | DKFZp686J07 | DKFZp686J07132; probably RAB30 but maybe SNORA70E | BX641138 | NM_014488 |
| uc002ncn.2 | DQ574353 | DQ574353 | DQ574353 | |
| uc011dhr.1 | FAM136B | hypothetical protein LOC387071 | NM_001012983 | NM_001012983 |
| uc011bzu.1 | FIP1L1 | FIP1 like 1 isoform 2 | NM_001134937 | NM_001134937 |
| uc002ecv.1 | IGH | IGH mRNA for immunoglobulin heavy chain VHDJ region: TRH1-22. | AF209882 | |
| uc003cxg.2 | MST1 | macrophage stimulating 1 (hepatocyte growth | NM_020998 | NM_020998 |
| uc003bau.2 | NHP2L1 | NHP2 non-histone chromosome protein 2-like 1 | CR591470 | NM_005008 |
| uc003bat.2 | NHP2L1 | NHP2 non-histone chromosome protein 2-like 1 | NM_005008 | NM_005008 |
| uc010mru.1 | patched a | patched a isoform mRNA for tumor suppressor | AB233423 | NM_001083602 |
| uc011cxt.1 | PHF15 | PHD finger protein 15 | AK294327 | NM_015288 |
| uc010rst.1 | RAB30 | RAB30, member RAS oncogene family | AK312323 | NM_014488 |
| uc001ozu.2 | RAB30 | RAB30, member RAS oncogene family | NM_014488 | NM_014488 |
| uc010aif.2 | RNASE2 | ribonuclease, RNase A family, 2 (liver, | BC143324 | NM_002934 |
| uc001yxi.2 | SNORD116-2 | small nucleolar RNA, C/D box 116-2 (SNORD116-2) | NR_003317 | NR_003317 |
| uc010gaq.1 | SNORD86 | small nucleolar RNA, C/D box 86 (SNORD86), non-coding RNA. | NR_004399 | NR_004399 |
| uc010prv.1 | SRGAP2 | SLIT-ROBO Rho GTPase activating protein 2 | AK293335 | NM_001042758 |
| uc011jow.1 | STK19 | SubName: Full = Serine/threonine kinase 19; | NR_026717 | NR_026717 |
| uc011hwf.1 | STK19 | SubName: Full = Serine/threonine kinase 19; | NR_026717 | NR_026717 |
| uc011ghs.1 | STK19 | SubName: Full = Serine/threonine kinase 19; | NR_026717 | NR_026717 |
| uc011fjw.1 | STK19 | SubName: Full = Serine/threonine kinase 19; | NR_026717 | NR_026717 |
| uc003nyt.2 | STK19 | SubName: Full = Serine/threonine kinase 19; | NR_026717 | NR_026717 |
| uc010ddw.2 | STRADA | STE20-related kinase adaptor alpha isoform 4 | AK309283 | NM_001003788 |
| uc002jbq.2 | STRADA | STE20-related kinase adaptor alpha isoform 4 | CR601658 | NM_001003788 |
| uc002jbn.2 | STRADA | STE20-related kinase adaptor alpha isoform 4 | NM_001003788 | NM_001003788 |
| uc002jbm.2 | STRADA | STE20-related kinase adaptor alpha isoform 1 | NM_001003787 | NM_001003787 |
| uc001wby.2 | TCRA | T cell receptor alpha variable 12, partial cds, clone: SEB 286. | AF327298 | |
| uc002qrr.1 | ZNF274 | zinc finger protein 274 isoform a | NM_016325 | NM_016325 |
| uc011mlu.1 | ZNF182 | zinc finger protein 21 isoform 2 | AK299325 | NM_001007088 |
| uc010scy.1 | WASH | SubName: Full = Actin nucleation promoting factor; Flags: Fragment; | AK290087 | NR_028269 |
| uc011azd.1 | ZNF619 | zinc finger protein 619 isoform 5 | NM_001145083 | NM_001145082 |
| uc009vzk.2 | TMEM48 | TMEM48 gene for transmembrane protein 48, | AL354612 | NM_018087 |
| uc001cvt.2 | TMEM48 | Nucleoporin NDC1; | AK298909 | NM_018087 |
| uc002ukl.1 | AX747372 | FLJ34815 fis, clone NT2NE2007786 CHR 2 near HOXD6 | AX747372 | |

TABLE 3

| GeneName | Symbol | Description | RefSeq |
| --- | --- | --- | --- |
| uc062qsc.1 | AP2M1 | adaptor-related protein complex 2, mu 1 subunit, transcript variant 2 | NM_001025205 |
| uc059jjm.1 | ARPP19 | cAMP-regulated phosphoprotein, 19 kDa, transcript variant 3 | NM_006628 |
| uc061ihy.1 | ATL2 | atlastin GTPase 2), transcript variant 2 | NM_001135673 |
| uc059ulu.1 | BBS2 | Bardet-Biedl syndrome 2, mRNA | NM_031885 |
| uc003dzb.5 | BTLA | B and T lymphocyte associated, transcript variant 2, mRNA | NM_001085357 |
| uc058mhg.1 | CCDC91 | coiled-coil domain containing 91 | NM_018318 |
| uc060awd.1 | CHD3 | chromodomain helicase DNA binding protein 3 (CHD3), variant 2 | NM_005852 |
| uc021quv.3 | CLEC2D | C-type lectin domain family 2, D (CLEC2D), variant 5, | NM_001197319 |
| uc021quw.3 | CLEC2D | C-type lectin domain family 2, member D (CLEC2D), variant 3, | NM_001197317 |
| uc059ubx.1 | CYLD | cylindromatosis (turban tumor syndrome) (CYLD), variant 1 | NM_015247 |
| uc061otq.1 | CYTIP | cytohesin 1 interacting protein (CYTIP), (NM_004288) | NM_004288 |
| uc011bwt.2 | DEFB131 | defensin, beta 131 (DEFB131), (NM_001040448) | NM_001040448 |
| uc021wlp.2 | DGCR8 | DGCR8 microprocessor complex subunit (DGCR), variant 2 | NM_001190326 |
| uc058pdq.1 | DGKA | diacylglycerol kinase, alpha 80 kDa (DGKA), transcript variant 4 | NM_201554 |
| uc058pdr.1 | DGKA | diacylglycerol kinase, alpha 80 kDa (DGKA RefSeq NM_201554) | NM_201554 |
| uc062seb.1 | DLG1 | discs, large homolog 1 (DLG1), variant 3(from RefSeq NM_001204386) | NM_001204386 |

TABLE 3-continued

| GeneName | Symbol | Description | RefSeq |
| --- | --- | --- | --- |
| uc063nld.1 | DXO, | decapping exoribonuclease (DXO), (NM_005510), | NM_005510 |
| uc063umn.1 | DXO, | decapping exoribonuclease (DXO), (NM_005510), | NM_005510 |
| uc063vry.1 | DXO, | decapping exoribonuclease (DXO), (NM_005510), | NM_005510 |
| uc063xwt.1 | DXO, | decapping exoribonuclease (DXO), (NM_005510), | NM_005510 |
| uc063zcr.1 | DXO, | decapping exoribonuclease (DXO), (NM_005510), | NM_005510 |
| uc064agm.1 | DXO, | decapping exoribonuclease (DXO), (NM_005510), | NM_005510 |
| uc060sqj.1 | FCER2 | Fc fragment of IgE, low affinity II, receptor for (CD23) | NM_002002 |
| uc064glm.1 | FIS1 | fission 1 (mitochondrial outer membrane) (FIS1, RefSeq NM_016068) | NM_016068 |
| uc060mdz.1 | FN3KRP | fructosamine 3 kinase related protein (FN3KRP), transcript variant 1, | NM_024619 |
| uc057dtw.1 | GPATCH3 | G patch domain containing 3 (GPATCH3), (NM_022078) | NM_022078 |
| uc063ixf.1 | GRIA1 | glutamate receptor, ionotropic, AMPA 1 (GRIA1)RefSeq NM_001258023) | NM_001258023 |
| uc058yoe.1 | GRK1 | Retina-specific kinase via phosphorylation of rhodopsin | NM_002929 |
| uc060tku.1 | ILF3 | interleukin enhancer binding factor 3, 90 kDa (ILF3), RefSeq NM_153464) | NM_153464 |
| uc058jgs.1 | JAM3 | junctional adhesion molecule 3 (JAM3)RefSeq NM_032801) | NM_032801 |
| uc057icn.1 | LINC1140 | long intergenic non-protein coding RNA 1140 | NR_026986 |
| uc064euq.1 | LOC101927269 | uncharacterized LOC101927269 long non-coding RNA | NR_110075 |
| uc062bub.1 | MED15 | mediator complex subunit 15 | NM_001293234 |
| uc032pwk.1 | MIR6130 | microRNA 6130 (MIR6130), microRNA. (from RefSeq NR_106746) | NR_106746 |
| uc058szl.1 | MMAB | methylmalonic aciduria (cobalamin deficiency) cblB type (MMAB) | NM_052845 |
| uc058urx.1 | MPHOSPH9 | M-phase phosphoprotein 9 | NR_103517 |
| uc021txo.2 | NT5C3B | 5'-nucleotidase, cytosolic IIIB (NT5C3B) | NM_052935 |
| uc062iet.1 | PLCD1 | phospholipase C, delta 1 (PLCD1) | NM_006225 |
| uc058per.1 | PMEL | premelanosome protein (PMEL)RefSeq NM_006928) | NM_006928 |
| uc063mxz.1 | PSORS1C1, | psoriasis susceptibility 1 candidate 1 (PSORS1C1) | NM_014068 |
| uc064umt.1 | PTCH1 | patched 1 (PTCH1) NM_001083606) | NM_001083606 |
| uc058mvt.1 | PUS7L | pseudouridylate synthase 7 homolog -like (PUS7L)NM_001098614) | NM_001098614 |
| uc058fzv.1 | RAB30 | RAB30, member RAS oncogene family | NM_001286060 |
| uc061mtr.1 | RGPD5 | RANBP2-like and GRIP domain containing 5 (RGPD5) | NM_032260 |
| uc061mvu.1 | RGPD5 | RANBP2-like and GRIP domain containing 5 (RGPD5) | NM_032260 |
| uc061mzr.1 | RGPD5 | RANBP2-like and GRIP domain containing 5 (RGPD5) | NM_005054 |
| uc064ble.1 | RPA3 | replication protein A3 | NM_001302348 |
| uc059xqn.1 | SDR42E1 | short chain dehydrogenase/reductase family 42E, member 1 (SDR42E1) | NM_145168 |
| uc058mys.1 | SLC38A1 | solute carrier family 38 member 1 | NM_001077484 |
| uc061irb.1 | THADA | thyroid adenoma associated | NR_073394 |
| uc058qzc.1 | TMEM19 | transmembrane protein 19 (TMEM19), (NM_018279) | NM_018279 |
| uc058ssh.1 | TMEM263 | transmembrane protein 263 (TMEM263), (NM_152261) | NM_152261 |
| uc062nfe.1 | UMPS | uridine 5'-monophosphate synthase | NR_033437 |
| uc058rwz.1 | VEZT | vezatin, adherens junctions transmembrane protein | NR_038241 |
| uc062brj.1 | ZDHHC8 | zinc finger, DHHC-type containing 8 (ZDHHC8) | NM_001185024 |
| uc061dng.1 | ZNF587 | zinc finger protein 587 (ZNF587) | NM_001204817 |
| uc061dni.1 | ZNF587 | zinc finger protein 587 (ZNF587) | NM_001204817 |
| uc057fla.1 | ZNF691 | zinc finger protein 691 (ZNF691) | NM_001242739 |
| uc060wdl.1 | ZNF93 | zinc finger protein 93 (ZNF93) | NM_031218 |

TABLE 4

| GeneName | Symbol | Description | RefSeq |
| --- | --- | --- | --- |
| uc003dzb.5 | BTLA | B and T lymphocyte associated (BTLA) | NM_001085357 |
| uc058pdr.1 | DGKA | diacylglycerol kinase, alpha 80 kDa (DGKA) | NM_201554 |
| uc059ubx.1 | CYLD | cylindromatosis (turban tumor syndrome) (CYLD) | NM_015247 |
| uc061otq.1 | CYTIP | cytohesin 1 interacting protein (CYTIP) | NM_004288 |
| uc062seb.1 | DLG1 | discs, large homolog 1 (*Drosophila*) (DLG1) | NM_001204386 |

TABLE 5

| GeneName | Symbol | Description | RefSeq |
| --- | --- | --- | --- |
| uc060fqa.1 | AARSD1 | alanyl-tRNA synthetase domain containing 1 (AARSD1), (NM_001261434) | NM_001261434 |
| uc059doe.1 | AC007182.6 | uncharacterized LOC102724153 (LOC102724153), long non-coding RNA. (NR_110552) | NR_110552 |
| uc062nxo.1 | ACAD11 | acyl-CoA dehydrogenase family, member 11 (ACAD11), (NM_032169) | NM_032169 |
| uc062rqu.1 | ACAP2 | ArfGAP with coiled-coil, ankyrin repeat and PH domains 2 (ACAP2), (NM_012287) | NM_012287 |
| uc057sjx.1 | ACBD5 | acyl-CoA binding domain containing 5 (ACBD5), var 2, (NM_001042473) | NM_001042473 |
| uc061wkb.1 | ACSS2 | acyl-CoA synthetase short-chain family member 2 (ACSS2), var 1, (NM_018677) | NM_018677 |
| uc059jsb.1 | ADAM10 | ADAM metallopeptidase domain 10 (ADAM10), (NM_001110) | NM_001110 |
| uc057vxr.1 | ADD3 | adducin 3 (gamma) (ADD3), var 3, (NM_001121) | NM_001121 |
| uc057vxz.1 | ADD3 | adducin 3 (gamma) (ADD3), var 2, (NM_019903) | NM_019903 |
| uc059ldj.1 | ADPGK | ADP-dependent glucokinase (ADPGK), var 1, (NM_031284) | NM_031284 |
| uc062uzv.1 | AFAP1 | actin filament associated protein 1 (AFAP1), var 2, (NM_198595) | NM_198595 |
| uc061jtt.1 | AFTPH | aftiphilin (AFTPH), var 1, (NM_203437) | NM_203437 |

TABLE 5-continued

| GeneName | Symbol | Description | RefSeq |
|---|---|---|---|
| uc064mhz.1 | AGPAT6 | 1-acylglycerol-3-phosphate O-acyltransferase 6 (AGPAT6), (NM_178819) | NM_178819 |
| uc057pqo.1 | AIDA | axin interactor, dorsalization associated (AIDA), (NM_022831) | NM_022831 |
| uc063qjb.1 | AIM1 | absent in melanoma 1 (AIM1), (NM_001624) | NM_001624 |
| uc059muo.1 | AKAP13 | A kinase (PRKA) anchor protein 13 (AKAP13), var 1, (NM_006738) | NM_006738 |
| uc062zbl.1 | ALPK1 | alpha-kinase 1 (ALPK1), var 1, (NM_025144) | NM_025144 |
| uc058uha.1 | ANAPC5 | anaphase promoting complex subunit 5 (ANAPC5), var 1, (NM_016237) | NM_016237 |
| uc064brx.1 | ANKMY2 | ankyrin repeat and MYND domain containing 2 (ANKMY2), (NM_020319) | NM_020319 |
| uc010pbw.3 | ANP32E | acidic (leucine-rich) nuclear phosphoprotein 32 family, member E (ANP32E), var 5, (NM_001280560) | NM_001280560 |
| uc031uyb.2 | ANP32E | acidic (leucine-rich) nuclear phosphoprotein 32 family, member E (ANP32E), var 2, (NM_001136478) | NM_001136478 |
| uc063gan.1 | APC | adenomatous polyposis coli (APC), var 1, (NM_001127511) | NM_001127511 |
| uc058jcu.1 | APLP2 | amyloid beta (A4) precursor-like protein 2 (APLP2), var 3, (NM_001142277) | NM_001142277 |
| uc058bav.1 | ARFGAP2 | ADP-ribosylation factor GTPase activating protein 2 (ARFGAP2), var 1, (NM_032389) | NM_032389 |
| uc063ifk.1 | ARHGAP26 | Rho GTPase activating protein 26 (ARHGAP26), var 2, (NM_001135608) | NM_001135608 |
| uc059jjn.1 | ARPP19 | cAMP-regulated phosphoprotein, 19 kDa (ARPP19), var 3, (NM_006628) | NM_006628 |
| uc063fiy.1 | ARRDC3 | arrestin domain containing 3 (ARRDC3), (NM_020801) | NM_020801 |
| uc064xvk.1 | ARSD | arylsulfatase D (ARSD), (NM_001669) | NM_001669 |
| uc061uez.1 | ASB1 | ankyrin repeat and SOCS box containing 1 (ASB1), (NM_001040445) | NM_001040445 |
| uc063qhc.1 | ASCC3 | activating signal cointegrator 1 complex subunit 3 (ASCC3), var 3, (NM_001284271) | NM_001284271 |
| uc060lsh.1 | ASPSCR1 | alveolar soft part sarcoma chromosome region, candidate 1 (ASPSCR1), var 1, (NM_024083) | NM_024083 |
| uc058lly.1 | ATF7IP | activating transcription factor 7 interacting protein (ATF7IP), var 4, (NM_001286515) | NM_001286515 |
| uc058lmb.1 | ATF7IP | activating transcription factor 7 interacting protein (ATF7IP), var 4, (NM_001286515) | NM_001286515 |
| uc058axh.1 | ATG13 | autophagy related 13 (ATG13), var 5, (NM_001205121) | NM_001205121 |
| uc061ihz.1 | ATL2 | atlastin GTPase 2 (ATL2), var 2, (NM_001135673) | NM_001135673 |
| uc058hbk.1 | ATM | ATM serine/threonine kinase (ATM), (NM_000051) | NM_000051 |
| uc003fla.3 | ATP11B | ATPase, class VI, type 11B (ATP11B), (NM_014616) | NM_014616 |
| uc062qmm.1 | ATP11B | ATPase, class VI, type 11B (ATP11B), (NM_014616) | NM_014616 |
| uc062oov.1 | ATR | ATR serine/threonine kinase (ATR), (NM_001184) | NM_001184 |
| uc065abm.1 | ATRX | alpha thalassemia/mental retardation syndrome X-linked (ATRX), var 2, (NM_138270) | NM_138270 |
| uc060ljk.1 | BAHCC1 | BAH domain and coiled-coil containing 1 (BAHCC1), (NM_001291324) | NM_001291324 |
| uc059ull.1 | BBS2 | Bardet-Biedl syndrome 2 (BBS2), (NM_031885) | NM_031885 |
| uc063rsr.1 | BCLAF1 | BCL2-associated transcription factor 1 (BCLAF1), var 3, (NM_001077441) | NM_001077441 |
| uc063lrz.1 | BLOC1S5 | biogenesis of lysosomal organelles complex-1, subunit 5, muted (BLOC1S5), var 1, (NM_201280) | NM_201280 |
| uc002icu.4 | BRCA1 | breast cancer 1, early onset (BRCA1), var 5, (NM_007299) | NM_007299 |
| uc010juh.4 | BRD2, | bromodomain containing 2 (BRD2), var 3, (NM_001199455), | NM_001199455 |
| uc011glh.3 | BRD2, | bromodomain containing 2 (BRD2), var 3, (NM_001199455), | NM_001199455 |
| uc059fyk.1 | C14orf79 | chromosome 14 open reading frame 79 (C14orf79), (NM_174891) | NM_174891 |
| uc059mpk.1 | C15orf40 | chromosome 15 open reading frame 40 (C15orf40), var 4, (NM_001160115) | NM_001160115 |
| uc010xhm.3 | C19orf71 | chromosome 19 open reading frame 71 (C19orf71), (NM_001135580) | NM_001135580 |
| uc003icv.5 | C4orf3 | chromosome 4 open reading frame 3 (C4orf3), var 2, (NM_001001701) | NM_001001701 |
| uc057whf.1 | CACUL1 | CDK2-associated, cullin domain 1 (CACUL1), (NM_153810) | NM_153810 |
| uc058osu.1 | CALCOCO1 | calcium binding and coiled-coil domain 1 (CALCOCO1), var 1, (NM_020898) | NM_020898 |
| uc060gxl.1 | CALCOCO2 | calcium binding and coiled-coil domain 2 (CALCOCO2), var 4, (NM_001261393) | NM_001261393 |
| uc060gxq.1 | CALCOCO2 | calcium binding and coiled-coil domain 2 (CALCOCO2), var 4, (NM_001261393) | NM_001261393 |
| uc010kyc.3 | CAMK2B | calcium/calmodulin-dependent protein kinase II beta (CAMK2B), var 9, (NM_001293170) | NM_001293170 |
| uc063kpi.1 | CANX | calnexin (CANX), var 1, (NM_001746) | NM_001746 |
| uc063kpk.1 | CANX | calnexin (CANX), var 2, (NM_001024649) | NM_001024649 |
| uc058ags.1 | CAPRIN1 | cell cycle associated protein 1 (CAPRIN1), var 2, (NM_203364) | NM_203364 |
| uc063bie.1 | CASP3 | caspase 3, apoptosis-related cysteine peptidase (CASP3), var alpha, (NM_004346) | NM_004346 |
| uc063big.1 | CASP3 | caspase 3, apoptosis-related cysteine peptidase (CASP3), var alpha, (NM_004346) | NM_004346 |
| uc062mdg.1 | CBLB | Cbl proto-oncogene B, E3 ubiquitin protein ligase (CBLB), (NM_170662) | NM_170662 |
| uc058mgx.1 | CCDC91 | coiled-coil domain containing 91 (CCDC91), (NM_018318) | NM_018318 |
| uc063omy.1 | CCND3 | cyclin D3 (CCND3), var 4, (NM_001136126) | NM_001136126 |
| uc064xux.1 | CD99, | CD99 molecule (CD99), var 2, (NM_001122898), | NM_001122898 |
| uc065coz.1 | CD99, | CD99 molecule (CD99), var 2, (NM_001122898), | NM_001122898 |
| uc063grw.1 | CDC42SE2 | CDC42 small effector 2 (CDC42SE2), var 1, (NM_020240) | NM_020240 |
| uc011lgp.2 | CDH17 | cadherin 17, LI cadherin (liver-intestine) (CDH17), var 2, (NM_001144663) | NM_001144663 |
| uc064vxm.1 | CDK9 | cyclin-dependent kinase 9 (CDK9), (NM_001261) | NM_001261 |
| uc058bfi.1 | CELF1 | CUGBP, Elav-like family member 1 (CELF1), var 4, (NM_001172639) | NM_001172639 |
| uc057rqw.1 | CELF2 | CUGBP, Elav-like family member 2 (CELF2), var 4, (NM_001083591) | NM_001083591 |
| uc063glq.1 | CEP120 | centrosomal protein 120 kDa (CEP120), var 2, (NM_001166226) | NM_001166226 |
| uc064wej.1 | CERCAM | cerebral endothelial cell adhesion molecule (CERCAM), var 2, (NM_001286760) | NM_001286760 |
| uc062ls1.1 | CGGBP1 | CGG triplet repeat binding protein 1 (CGGBP1), var 2, (NM_003663) | NM_003663 |
| uc060awd.1 | CHD3 | chromodomain helicase DNA binding protein 3 (CHD3), var 2, (NM_005852) | NM_005852 |
| uc059wmz.1 | CLEC18A | C-type lectin domain family 18, member A (CLEC18A), var 3, (NM_001271197) | NM_001271197 |
| uc011hbe.1 | CLIC1, | chloride intracellular channel 1 (CLIC1), var 1, (NM_001287593), | NM_001287593 |
| uc059emx.1 | CPSF2 | cleavage and polyadenylation specific factor 2, 100 kDa (CPSF2), (NM_017437) | NM_017437 |
| uc061rvc.1 | CREB1 | cAMP responsive element binding protein 1 (CREB1), var B, (NM_134442) | NM_134442 |
| uc061rvk.1 | CREB1 | cAMP responsive element binding protein 1 (CREB1), var B, (NM_134442) | NM_134442 |
| uc060lyh.1 | CSNK1D | casein kinase 1, delta (CSNK1D), var 1, (NM_001893) | NM_001893 |
| uc060ozj.1 | CTIF | CBP80/20-dependent translation initiation factor (CTIF), var 1, (NM_014772) | NM_014772 |
| uc060ozk.1 | CTIF | CBP80/20-dependent translation initiation factor (CTIF), var 1, (NM_001142397) | NM_001142397 |
| uc060ozl.1 | CTIF | CBP80/20-dependent translation initiation factor (CTIF), var 1, (NM_014772) | NM_014772 |
| uc060ozm.1 | CTIF | CBP80/20-dependent translation initiation factor (CTIF), var 1, (NM_014772) | NM_014772 |
| uc060ozo.1 | CTIF | CBP80/20-dependent translation initiation factor (CTIF), var 1, (NM_014772) | NM_014772 |
| uc057gtx.1 | CYB5RL | cytochrome b5 reductase-like (CYB5RL), (NM_001031672) | NM_001031672 |
| uc060kvy.1 | CYTH1 | cytohesin 1 (CYTH1), var 2, (NM_017456) | NM_017456 |

TABLE 5-continued

| GeneName | Symbol | Description | RefSeq |
|---|---|---|---|
| uc062dxh.1 | CYTH4 | cytohesin 4 (CYTH4), (NM_013385) | NM_013385 |
| uc064bhy.1 | DAGLB | diacylglycerol lipase, beta (DAGLB), var 2, (NM_001142936) | NM_001142936 |
| uc064dej.1 | DBNL | drebrin-like (DBNL), var 5, (NM_001284315) | NM_001284315 |
| uc062efz.1 | DDX17 | DEAD (Asp-Glu-Ala-Asp) box helicase 17 (DDX17), var 1, (NM_006386) | NM_006386 |
| uc058nka.1 | DDX23 | DEAD (Asp-Glu-Ala-Asp) box polypeptide 23 (DDX23), (NM_004818) | NM_004818 |
| uc058nkb.1 | DDX23 | DEAD (Asp-Glu-Ala-Asp) box polypeptide 23 (DDX23), (NM_004818) | NM_004818 |
| uc060iwr.1 | DDX5 | DEAD (Asp-Glu-Ala-Asp) box helicase 5 (DDX5), (NM_004396) | NM_004396 |
| uc058ibi.1 | DDX6 | DEAD (Asp-Glu-Ala-Asp) box helicase 6 (DDX6), var 2, (NM_001257191) | NM_001257191 |
| uc058uoi.1 | DENR | density-regulated protein (DENR), (NM_003677) | NM_003677 |
| uc061wzp.1 | DHX35 | DEAH (Asp-Glu-Ala-His) box polypeptide 35 (DHX35), var 2, (NM_001190809) | NM_001190809 |
| uc059etw.1 | DICER1 | dicer 1, ribonuclease type III (DICER1), var 3, (NM_001195573) | NM_001195573 |
| uc059etz.1 | DICER1 | dicer 1, ribonuclease type III (DICER1), var 3, (NM_001195573) | NM_001195573 |
| uc058nyl.1 | DIP2B | DIP2 disco-interacting protein 2 homolog B (Drosophila) (DIP2B), (NM_173602) | NM_173602 |
| uc011buf.2 | DLG1 | discs, large homolog 1 (Drosophila) (DLG1), var 2, (NM_004087) | NM_004087 |
| uc061wtd.1 | DLGAP4 | discs, large (Drosophila) homolog-associated protein 4 (DLGAP4), var 3, (NM_001042486) | NM_001042486 |
| uc061wte.1 | DLGAP4 | discs, large (Drosophila) homolog-associated protein 4 (DLGAP4), var 1, (NM_014902) | NM_014902 |
| uc061wtf.1 | DLGAP4 | discs, large (Drosophila) homolog-associated protein 4 (DLGAP4), var 3, (NM_001042486) | NM_001042486 |
| uc057pwi.1 | DNAH14 | dynein, axonemal, heavy chain 14 (DNAH14), var 1, (NM_001373) | NM_001373 |
| uc060kvg.1 | DNAH17 | dynein, axonemal, heavy chain 17 (DNAH17), (NM_173628) | NM_173628 |
| uc062abg.1 | DSCR8 | Down syndrome critical region 8 (DSCR8), var 4, long non-coding RNA. (NR_026838) | NR_026838 |
| uc057nxe.1 | EDEM3 | ER degradation enhancer, mannosidase alpha-like 3 (EDEM3), (NM_025191) | NM_025191 |
| uc064rbq.1 | EEF1D, | eukaryotic translation elongation factor 1 delta (guanine nucleotide exchange protein) (EEF1D), var 1, (NM_032378), | NM_032378 |
| uc064rbu.1 | EEF1D, | eukaryotic translation elongation factor 1 delta (guanine nucleotide exchange protein) (EEF1D), var 1, (NM_032378), | NM_032378 |
| uc064rbv.1 | EEF1D, | eukaryotic translation elongation factor 1 delta (guanine nucleotide exchange protein) (EEF1D), var 1, (NM_032378), | NM_032378 |
| uc021qlv.2 | EIF1AD | eukaryotic translation initiation factor 1A domain containing (EIF1AD), var 7, (NM_001242486) | NM_001242486 |
| uc058uud.1 | EIF2B1 | eukaryotic translation initiation factor 2B, subunit 1 alpha, 26 kDa (EIF2B1), (NM_001414) | NM_001414 |
| uc064yjf.1 | EIF2S3 | eukaryotic translation initiation factor 2, subunit 3 gamma, 52 kDa (EIF2S3), (NM_001415) | NM_001415 |
| uc058ojv.1 | EIF4B | eukaryotic translation initiation factor 4B (EIF4B), var 2, (NM_001417) | NM_001417 |
| uc009xrx.4 | EIF5AL1 | eukaryotic translation initiation factor 5A-like 1 (EIF5AL1), (NM_001099692) | NM_001099692 |
| uc064cwd.1 | ELMO1 | engulfment and cell motility 1 (ELMO1), var 1, (NM_014800) | NM_014800 |
| uc057aua.1 | FAM138A | family with sequence similarity 138, member C (FAM138C), long non-coding RNA. (NR_026822) | NR_026822 |
| uc064rsw.1 | FAM138A | family with sequence similarity 138, member C (FAM138C), long non-coding RNA. (NR_026822) | NR_026822 |
| uc064wvy.1 | FAM163B | family with sequence similarity 163, member B (FAM163B), (NM_001080515) | NM_001080515 |
| uc001iod.2 | FAM188A | family with sequence similarity 188, member A (FAM188A), (NM_024948) | NM_024948 |
| uc064tcq.1 | FBXO10 | F-box protein 10 (FBXO10), (NM_012166) | NM_012166 |
| uc057mrz.1 | FCGR2A | Fc fragment of IgG, low affinity IIa, receptor (CD32) (FCGR2A), var 2, (NM_021642) | NM_021642 |
| uc002mny.2 | FDX1L | ferredoxin 1-like (FDX1L), (NM_001031734) | NM_001031734 |
| uc002esl.4 | FHOD1 | formin homology 2 domain containing 1 (FHOD1), (NM_013241) | NM_013241 |
| uc032bem.2 | FUT8 | fucosyltransferase 8 (alpha (1,6) fucosyltransferase) (FUT8), var 4, (NM_004480) | NM_004480 |
| uc060ato.1 | FXR2 | fragile X mental retardation, autosomal homolog 2 (FXR2), (NM_004860) | NM_004860 |
| uc059alo.1 | G2E3 | G2/M-phase specific E3 ubiquitin protein ligase (G2E3), var 1, (NM_017769) | NM_017769 |
| uc062xjk.1 | G3BP2 | GTPase activating protein (SH3 domain) binding protein 2 (G3BP2), var 2, (NM_012297) | NM_012297 |
| uc058fwz.1 | GAB2 | GRB2-associated binding protein 2 (GAB2), var 1, (NM_080491) | NM_080491 |
| uc064dty.1 | GBAS | glioblastoma amplified sequence (GBAS), var 1, (NM_001483) | NM_001483 |
| uc057jua.1 | GDAP2 | ganglioside induced differentiation associated protein 2 (GDAP2), var 2, (NM_001135589) | NM_001135589 |
| uc057rkp.1 | GDI2 | GDP dissociation inhibitor 2 (GDI2), var 1, (NM_001494) | NM_001494 |
| uc061qst.1 | GLS | glutaminase (GLS), var 2, (NM_001256310) | NM_001256310 |
| uc060dnv.1 | GOSR1 | golgi SNAP receptor complex member 1 (GOSR1), var 1, (NM_004871) | NM_004871 |
| uc058uuj.1 | GTF2H3 | general transcription factor IIH, polypeptide 3, 34 kDa (GTF2H3), var 1, (NM_001516) | NM_001516 |
| uc061qxu.1 | GTF3C3 | general transcription factor IIIC, polypeptide 3, 102 kDa (GTF3C3), var 2, (NM_001206774) | NM_001206774 |
| uc060kcl.1 | H3F3B | H3 histone, family 3B (H3.3B) (H3F3B), (NM_005324) | NM_005324 |
| uc062uow.1 | HAUS3 | HAUS augmin-like complex, subunit 3 (HAUS3), var 1, (NM_001303143) | NM_001303143 |
| uc003lwi.3 | HAVCR1 | hepatitis A virus cellular receptor 1 (HAVCR1), var 1, (NM_012206) | NM_012206 |
| uc063xls.1 | HCG27 | HLA complex group 27 (non-protein coding) (HCG27), long non-coding RNA. (NR_026791) | NR_026791 |
| uc010lli.4 | HILPDA | hypoxia inducible lipid droplet-associated (HILPDA), var 2, (NM_001098786) | NM_001098786 |
| uc057klm.1 | HIST2H2BF | histone cluster 2, H2bf (HIST2H2BF), var 2, (NM_001161334) | NM_001161334 |
| uc011hpm.2 | HLA-C, | major histocompatibility complex, class I, C (HLA-C), var 1, (NM_002117), | NM_002117 |
| uc063kni.1 | HNRNPH1 | heterogeneous nuclear ribonucleoprotein H1 (H) (HNRNPH1), var 2, (NM_005520) | NM_005520 |
| uc010jad.5 | HOMER1 | homer scaffolding protein 1 (HOMER1), var 1, (NM_004272) | NM_004272 |
| uc057zqa.1 | HPS5 | Hermansky-Pudlak syndrome 5 (HPS5), var 3, (NM_181508) | NM_181508 |
| uc059fki.1 | HSP90AA1 | heat shock protein 90 kDa alpha (cytosolic), class A member 1 (HSP90AA1), var 2, (NM_005348) | NM_005348 |
| uc058ipc.1 | HSPA8 | heat shock 70 kDa protein 8 (HSPA8), var 2, (NM_153201) | NM_153201 |
| uc062pnl.1 | IFT80 | intraflagellar transport 80 (IFT80), var 1, (NM_020800) | NM_020800 |
| uc063dsb.1 | IL6ST | interleukin 6 signal transducer (IL6ST), var 1, (NM_002184) | NM_002184 |
| uc064vct.1 | INIP | INTS3 and NABP interacting protein (INIP), (NM_021218) | NM_021218 |
| uc058fvh.1 | INTS4 | integrator complex subunit 4 (INTS4), (NM_033547) | NM_033547 |
| uc063bhq.1 | IRF2 | interferon regulatory factor 2 (IRF2), (NM_002199) | NM_002199 |
| uc063bht.1 | IRF2 | interferon regulatory factor 2 (IRF2), (NM_002199) | NM_002199 |
| uc057hez.1 | ITGB38P | integrin beta 3 binding protein (beta3-endonexin) (ITGB3BP), var 2, (NM_014288) | NM_014288 |
| uc065acj.1 | ITM2A | integral membrane protein 2A (ITM2A), var 1, (NM_004867) | NM_004867 |
| uc065ack.1 | ITM2A | integral membrane protein 2A (ITM2A), var 2, (NM_001171581) | NM_001171581 |
| uc057tnu.1 | JMJD1C | jumonji domain containing 1C (JMJD1C), var 3, (NM_001282948) | NM_001282948 |
| uc003awf.4 | JOSD1 | Josephin domain containing 1 (JOSD1), (NM_014876) | NM_014876 |
| uc064miu.1 | KAT6A | K(lysine) acetyltransferase 6A (KAT6A), var 1, (NM_006766) | NM_006766 |
| uc058syp.1 | KCTD10 | potassium channel tetramerization domain containing 10 (KCTD10), (NM_031954) | NM_031954 |

TABLE 5-continued

| GeneName | Symbol | Description | RefSeq |
|---|---|---|---|
| uc058hck.1 | KDELC2 | KDEL (Lys-Asp-Glu-Leu) containing 2 (KDELC2), (NM_153705) | NM_153705 |
| uc060sag.1 | KDM4B | lysine (K)-specific demethylase 4B (KDM4B), (NM_015015) | NM_015015 |
| uc058jos.1 | KDM5A | lysine (K)-specific demethylase 5A (KDM5A), (NM_001042603) | NM_001042603 |
| uc058jox.1 | KDM5A | lysine (K)-specific demethylase 5A (KDMSA), (NM_001042603) | NM_001042603 |
| uc058joy.1 | KDM5A | lysine (K)-specific demethylase 5A (KDM5A), (NM_001042603) | NM_001042603 |
| uc064zkl.1 | KDM5C | lysine (K)-specific demethylase 5C (KDM5C), var 3, (NM_001282622) | NM_001282622 |
| uc064zkp.1 | KDM5C | lysine (K)-specific demethylase 5C (KDM5C), var 2, (NM_001146702) | NM_001146702 |
| uc060jye.1 | KIAA0195 | KIAA0195 (KIAA0195), (NM_014738) | NM_014738 |
| uc057esn.1 | KIAA0319L | KIAA0319-like (KIAA0319L), (NM_024874) | NM_024874 |
| uc058spq.1 | KIAA1033 | KIAA1033 (KIAA1033), var 2, (NM_015275) | NM_015275 |
| uc064sam.1 | KIAA2026 | KIAA2026 (KIAA2026), (NM_001017969) | NM_001017969 |
| uc059fsz.1 | KLC1 | kinesin light chain 1 (KLC1), var 3, (NM_001130107) | NM_001130107 |
| uc003otu.4 | KLC4 | kinesin light chain 4 (KLC4), var 4, (NM_138343) | NM_138343 |
| uc063oov.1 | KLC4 | kinesin light chain 4 (KLC4), var 1, (NM_201521) | NM_201521 |
| uc059bch.1 | KLHL28 | kelch-like family member 28 (KLHL28), var 2, (NM_017658) | NM_017658 |
| uc010eof.4 | KLK3 | kallikrein-related peptidase 3 (KLK3), var 1, (NM_001648) | NM_001648 |
| uc021uyi.2 | KLK3 | kallikrein-related peptidase 3 (KLK3), var 1, (NM_001648) | NM_001648 |
| uc061bti.1 | KLK3 | kallikrein-related peptidase 3 (KLK3), var 1, (NM_001648) | NM_001648 |
| uc064gta.1 | KMT2E | lysine (K)-specific methyltransferase 2E (KMT2E), var 1, (NM_182931) | NM_182931 |
| uc064gtb.1 | KMT2E | lysine (K)-specific methyltransferase 2E (KMT2E), var 1, (NM_182931) | NM_182931 |
| uc010taf.3 | KNTC1 | kinetochore associated 1 (KNTC1), (NM_014708) | NM_014708 |
| uc058nxw.1 | LARP4 | La ribonucleoprotein domain family, member 4 (LARP4), var 5, (NM_001170804) | NM_001170804 |
| uc064wbe.1 | LCN2 | lipocalin 2 (LCN2), (NM_005564) | NM_005564 |
| uc057hgz.1 | LEPROT | leptin receptor overlapping transcript (LEPROT), var 1, (NM_017526) | NM_017526 |
| uc060cva.1 | LGALS9 | lectin, galactoside-binding, soluble, 9 (LGALS9), var 2, (NM_002308) | NM_002308 |
| uc060cvb.1 | LGALS9 | lectin, galactoside-binding, soluble, 9 (LGALS9), var 2, (NM_002308) | NM_002308 |
| uc059eoc.1 | LGMN | legumain (LGMN), var 2, (NM_001008530) | NM_001008530 |
| uc063evg.1 | LHFPL2 | lipoma HMGIC fusion partner-like 2 (LHFPL2), (NM_005779) | NM_005779 |
| uc032idl.2 | LILRB2 | leukocyte immunoglobulin-like receptor, subfamily B (with TM and ITIM domains), member 2 (LILRB2), var 1, (NM_005874), | NM_005874 |
| uc032idm.2 | LILRB2, | leukocyte immunoglobulin-like receptor, subfamily B (with TM and ITIM domains), member 2 (LILRB2), var 2, (NM_001080978), | NM_001080978 |
| uc061msl.1 | LIMS1 | LIM and senescent cell antigen-like domains 1 (LIMS1), var 1, (NM_001193485) | NM_001193485 |
| uc062mdq.1 | LINC00883 | long intergenic non-protein coding RNA 883 (LINC00883), var 2, long non-coding RNA. (NR_028302) | NR_028302 |
| uc058joz.1 | LOC389273 | uncharacterized LOC389273 | XR_241740.2 |
| uc002sty.3 | MAL | mal, T-cell differentiation protein (MAL), var c, (NM_022439) | NM_022439 |
| uc002sua.3 | MAL | mal, T-cell differentiation protein (MAL), var d, (NM_022440) | NM_022440 |
| uc061mla.1 | MAP4K4 | mitogen-activated protein kinase kinase kinase kinase 4 (MAP4K4), var 5, (NM_001242560) | NM_001242560 |
| uc058ykh.1 | MCF2L | MCF.2 cell line derived transforming sequence-like (MCF2L), var 1, (NM_001112732) | NM_001112732 |
| uc057kpe.1 | MCL1 | myeloid cell leukemia 1 (MCL1), var 3, (NM_001197320) | NM_001197320 |
| uc057wjc.1 | MCMBP | minichromosome maintenance complex binding protein (MCMBP), var 3, (NM_001256379) | NM_001256379 |
| uc058qrl.1 | MDM2 | MDM2 proto-oncogene, E3 ubiquitin protein ligase (MDM2), var 2, (NM_001145339) | NM_001145339 |
| uc058qru.1 | MDM2 | MDM2 proto-oncogene, E3 ubiquitin protein ligase (MDM2), var 5, (NM_001278462) | NM_001278462 |
| uc058qsc.1 | MDM2 | MDM2 proto-oncogene, E3 ubiquitin protein ligase (MDM2), var 1, (NM_002392) | NM_002392 |
| uc058qsh.1 | MDM2 | MDM2 proto-oncogene, E3 ubiquitin protein ligase (MDM2), var 3, (NM_001145337) | NM_001145337 |
| uc057ore.1 | MDM4 | MDM4, p53 regulator (MDM4), var 2, (NM_001204171) | NM_001204171 |
| uc059nun.1 | MEF2A | myocyte enhancer factor 2A (MEF2A), var 1, (NM_005587) | NM_005587 |
| uc057pqd.1 | MIA3 | melanoma inhibitory activity family, member 3 (MIA3), var 2, (NM_001300867) | NM_001300867 |
| uc022ahx.1 | MIR3609 | microRNA 3609 (MIR3609), microRNA. (NR_037403) | NR_037403 |
| uc061zyh.1 | MORC3 | MORC family CW-type zinc finger 3 (MORC3), (NM_015358) | NM_015358 |
| uc065bfd.1 | MOSPD1 | motile sperm domain containing 1 (MOSPD1), var 1, (NM_019556) | NM_019556 |
| uc064xzd.1 | MSL3 | male-specific lethal 3 homolog (*Drosophila*) (MSL3), var 5, (NM_001193270) | NM_001193270 |
| uc064xze.1 | MSL3 | male-specific lethal 3 homolog (*Drosophila*) (MSL3), var 5, (NM_001193270) | NM_001193270 |
| uc057iik.1 | MTF2 | metal response element binding transcription factor 2 (MTF2), var 2, (NM_001164392) | NM_001164392 |
| uc058eoh.1 | MTL5 | metallothionein-like 5, testis-specific (tesmin) (MTL5), var 1, (NM_004923) | NM_004923 |
| uc059hcg.1 | MTMR10, | myotubularin related protein 10 (MTMR10), (NM_017762), | NM_017762 |
| uc058glm.1 | MTNR1B | melatonin receptor 1B (MTNR1B), (NM_005959) | NM_005959 |
| uc059yie.1 | MVD | mevalonate (diphospho) decarboxylase (MVD), (NM_002461) | NM_002461 |
| uc059juf.1 | MYO1E | myosin IE (MYO1E), (NM_004998) | NM_004998 |
| uc004dwj.4 | n/a | n/a | NM_001184830 |
| uc009yzb.3 | n/a | n/a | NR_034148 |
| uc009zrh.6 | n/a | n/a | NM_001145340 |
| uc010lxd.3 | n/a | n/a | NM_001305878 |
| uc010rqa.2 | n/a | n/a | NM_001300909 |
| uc011ddh.3 | n/a | n/a | NM_001301086 |
| uc031rql.2 | n/a | n/a | NR_102429 |
| uc032yru.2 | n/a | n/a | NR_130726 |
| uc057feg.1 | n/a | n/a | NM_001105530 |
| uc057ghm.1 | n/a | n/a | NM_001290406 |
| uc057knd.1 | n/a | n/a | NM_001280559 |
| uc057mkc.1 | n/a | n/a | NM_001193644 |
| uc057oir.1 | n/a | n/a | NM_001193570 |
| uc057svn.1 | n/a | n/a | NR_130948 |
| uc057vsc.1 | n/a | n/a | NM_001134373 |
| uc058eer.1 | n/a | n/a | NR_046413 |
| uc058guv.1 | n/a | n/a | NM_001165 |
| uc058hgh.1 | n/a | n/a | NM_001289807 |

TABLE 5-continued

| GeneName | Symbol | Description | RefSeq |
|---|---|---|---|
| uc058mbp.1 | n/a | n/a | NR_038228 |
| uc058mkd.1 | n/a | n/a | NM_001002259 |
| uc058mwc.1 | n/a | n/a | NM_001145256 |
| uc058mys.1 | n/a | n/a | NM_001077484 |
| uc058nzl.1 | n/a | n/a | NR_033422 |
| uc058rwz.1 | n/a | n/a | NR_038241 |
| uc058tqf.1 | n/a | n/a | NR_126425 |
| uc059fgi.1 | n/a | n/a | NR_046473 |
| uc060dou.1 | n/a | n/a | NR_073118 |
| uc060oun.1 | n/a | n/a | NM_001001935 |
| uc060txk.1 | n/a | n/a | NM_001203250 |
| uc060upk.1 | n/a | n/a | NR-038104 |
| uc060wbt.1 | n/a | n/a | NM_001288998 |
| uc060wga.1 | n/a | n/a | NR_117086 |
| uc060wgb.1 | n/a | n/a | NR_117086 |
| uc060wgc.1 | n/a | n/a | NR_117087 |
| uc061cep.1 | n/a | n/a | NM_001105551 |
| uc061cjy.1 | n/a | n/a | NM_001289953 |
| uc061ihw.1 | n/a | n/a | NR_024191 |
| uc061jgl.1 | n/a | n/a | NM_001005369 |
| uc061kmo.1 | n/a | n/a | NM_001252613 |
| uc061kmp.1 | n/a | n/a | NM_001252613 |
| uc061kmt.1 | n/a | n/a | NM_001252613 |
| uc061nys.1 | n/a | n/a | NR_037649 |
| uc061pwt.1 | n/a | n/a | NR_045774 |
| uc061wpc.1 | n/a | n/a | NM_001198838 |
| uc062epc.1 | n/a | n/a | NM_001278589 |
| uc062hyt.1 | n/a | n/a | NM_001256192 |
| uc062hyu.1 | n/a | n/a | NM_001256192 |
| uc062hyv.1 | n/a | n/a | NM_001256192 |
| uc062hyw.1 | n/a | n/a | NM_001256192 |
| uc062qnh.1 | n/a | n/a | NR_120639 |
| uc062shh.1 | n/a | n/a | NM_001145248 |
| uc063dic.1 | n/a | n/a | NR_102752 |
| uc063hcr.1 | n/a | n/a | NR_125341 |
| uc063igg.1 | n/a | n/a | NM_001204265 |
| uc063msn.1 | n/a | n/a | NR_072994 |
| uc063pfr.1 | n/a | n/a | NM_001286276 |
| uc063pgm.1 | n/a | n/a | NR_110742 |
| uc063pgn.1 | n/a | n/a | NR_110742 |
| uc063twg.1 | n/a | n/a | NR_072994 |
| uc063vce.1 | n/a | n/a | NR_072994 |
| uc063wht.1 | n/a | n/a | NR_072994 |
| uc063xhc.1 | n/a | n/a | NR_072994 |
| uc063ymy.1 | n/a | n/a | NR_072994 |
| uc063zst.1 | n/a | n/a | NR_072994 |
| uc064cua.1 | n/a | n/a | NM_001011553 |
| uc064jpb.1 | n/a | n/a | NR_126344 |
| uc064pgq.1 | n/a | n/a | NM_001301668 |
| uc064pzo.1 | n/a | n/a | NR_027427 |
| uc064sde.1 | n/a | n/a | NR_125775 |
| uc064ufl.1 | n/a | n/a | NR_034157 |
| uc064wlb.1 | n/a | n/a | NR_038955 |
| uc010trk.3 | NAA30 | N(alpha)-acetyltransferase 30, NatC catalytic subunit (NAA30), (NM_001011713) | NM_001011713 |
| uc061quf.1 | NABP1 | nucleic acid binding protein 1 (NABP1), var 2, (NM_001254736) | NM_001254736 |
| uc060pne.1 | NARS | asparaginyl-tRNA synthetase (NARS), (NM_004539) | NM_004539 |
| uc021yem.2 | NDUFA2 | NADH dehydrogenase (ubiquinone) 1 alpha subcomplex, 2, 8 kDa (NDUFA2), var 2, (NM_001185012) | NM_001185012 |
| uc060sua.1 | NDUFA7 | NADH dehydrogenase (ubiquinone) 1 alpha subcomplex, 7, 14.5 kDa (NDUFA7), (NM_005001) | NM_005001 |
| uc064ipg.1 | NDUFB2 | NADH dehydrogenase (ubiquinone) 1 beta subcomplex, 2, 8 kDa (NDUFB2), (NM_004546) | NM_004546 |
| uc061rhu.1 | NDUFB3 | NADH dehydrogenase (ubiquinone) 1 beta subcomplex, 3, 12 kDa (NDUFB3), var 1, (NM_002491) | NM_002491 |
| uc063lwh.1 | NEDD9 | neural precursor cell expressed, developmentally down-regulated 9 (NEDD9), var 3, (NM_001142393) | NM_001142393 |
| uc062kpm.1 | NEK4 | NIMA-related kinase 4 (NEK4), var 2, (NM_001193533) | NM_001193533 |
| uc062yor.1 | NFKB1 | nuclear factor of kappa light polypeptide gene enhancer in B-cells 1 (NFKB1), var 2, (NM_001165412) | NM_001165412 |
| uc003ggh.4 | NOP14-AS1 | NOP14 antisense RNA 1 (NOP14-AS1), long non-coding RNA. (NR_015453) | NR_015453 |
| uc063kbs.1 | NSD1 | nuclear receptor binding SET domain protein 1 (NSD1), var 1, (NM_172349) | NM_172349 |
| uc057zmg.1 | NUCB2 | nucleobindin 2 (NUCB2), (NM_005013) | NM_005013 |
| uc032qqz.2 | NUP50 | nucleoporin 50 kDa (NUP50), var 3, (NM_153645) | NM_153645 |
| uc058vyt.1 | NUPL1 | nucleoporin like 1 (NUPL1), var 1, (NM_014089) | NM_014089 |
| uc057wpi.1 | OAT | ornithine aminotransferase (OAT), var 2, (NM_001171814) | NM_001171814 |
| uc057rze.1 | OLAH | oleoyl-ACP hydrolase (OLAH), var 1, (NM_018324) | NM_018324 |
| uc058qat.1 | OS9 | osteosarcoma amplified 9, endoplasmic reticulum lectin (OS9), var 7, (NM_001261422) | NM_001261422 |
| uc064plv.1 | OXR1 | oxidation resistance 1 (OXR1), var 5, (NM_001198534) | NM_001198534 |
| uc063dlu.1 | PARP8 | poly (ADP-ribose) polymerase family, member 8 (PARP8), var 3, (NM_001178056) | NM_001178056 |
| uc061ncw.1 | PAX8-AS1 | PAX8 antisense RNA 1 (PAX8-AS1), var 1, long non-coding RNA. (NR_015377) | NR_015377 |

TABLE 5-continued

| GeneName | Symbol | Description | RefSeq |
|---|---|---|---|
| uc001hvl.3 | PCNXL2 | pecanex-like 2 (*Drosophila*) (PCNXL2), (NM_014801) | NM_014801 |
| uc057vzf.1 | PDCD4 | programmed cell death 4 (neoplastic transformation inhibitor) (PDCD4), var 1, (NM_014456) | NM_014456 |
| uc061jsz.1 | PELI1 | pellino E3 ubiquitin protein ligase 1 (PELI1), (NM_020651) | NM_020651 |
| uc061jtb.1 | PELI1 | pellino E3 ubiquitin protein ligase 1 (PELI1), (NM_020651) | NM_020651 |
| uc057oyp.1 | PFKFB2 | 6-phosphofructo-2-kinase/fructose-2,6-biphosphatase 2 (PFKFB2), var 2, (NM_001018053) | NM_001018053 |
| uc060kui.1 | PGS1 | phosphatidylglycerophosphate synthase 1 (PGS1), var 1, (NM_024419) | NM_024419 |
| uc061wrj.1 | PHF20 | PHD finger protein 20 (PHF20), (NM_016436) | NM_016436 |
| uc064qis.1 | PHF20L1 | PHD finger protein 20-like 1 (PHF20L1), var 1, (NM_016018) | NM_016018 |
| uc064zlz.1 | PHF8 | PHD finger protein 8 (PHF8), var 1, (NM_001184896) | NM_001184896 |
| uc059tvz.1 | PHKB | phosphorylase kinase, beta (PHKB), var 1, (NM_000293) | NM_000293 |
| uc059zgk.1 | PITPNA | phosphatidylinositol transfer protein, alpha (PITPNA), (NM_006224) | NM_006224 |
| uc059ibd.1 | PLA2G4B | phospholipase A2, group IVB (cytosolic) (PLA2G4B), (NM_001114633) | NM_001114633 |
| uc009ypg.3 | PLCB3 | phospholipase C, beta 3 (phosphatidylinositol-specific) (PLCB3), var 1, (NM_000932) | NM_000932 |
| uc009yph.3 | PLCB3 | phospholipase C, beta 3 (phosphatidylinositol-specific) (PLCB3), var 2, (NM_001184883) | NM_001184883 |
| uc009ypi.4 | PLCB3 | phospholipase C, beta 3 (phosphatidylinositol-specific) (PLCB3), var 1, (NM_000932) | NM_000932 |
| uc061jyj.1 | PLEK | pleckstrin (PLEK), (NM_002664) | NM_002664 |
| uc060rxx.1 | PLIN5 | perilipin 5 (PLIN5), (NM_001013706) | NM_001013706 |
| uc058rhy.1 | PPP1R12A | protein phosphatase 1, regulatory subunit 12A (PPP1R12A), var 5, (NM_001244992) | NM_001244992 |
| uc057hys.1 | PRKACB | protein kinase, cAMP-dependent, catalytic, beta (PRKACB), var 10, (NM_001300915) | NM_001300915 |
| uc003cuy.2 | PRKAR2A | protein kinase, cAMP-dependent, regulatory, type II, alpha (PRKAR2A), (NM_004157) | NM_004157 |
| uc062jlv.1 | PRKAR2A | protein kinase, cAMP-dependent, regulatory, type II, alpha (PRKAR2A), (NM_004157) | NM_004157 |
| uc062jlw.1 | PRKAR2A | protein kinase, cAMP-dependent, regulatory, type II, alpha (PRKAR2A), (NM_004157) | NM_004157 |
| uc001ldp.2 | PRLHR | prolactin releasing hormone receptor (PRLHR), (NM_004248) | NM_004248 |
| uc058oqd.1 | PRR13 | proline rich 13 (PRR13), var 3, (NM_001005354) | NM_001005354 |
| uc059byu.1 | PSMA3-AS1 | PSMA3 antisense RNA 1 (PSMA3-AS1), var 1, long non-coding RNA. (NR_029434) | NR_029434 |
| uc004enq.3 | PSMD10 | proteasome (prosome, macropain) 26S subunit, non-ATPase, 10 (PSMD10), var 2, (NM_170750) | NM_170750 |
| uc065apw.1 | PSMD10 | proteasome (prosome, macropain) 26S subunit, non-ATPase, 10 (PSMD10), var 1, (NM_002814) | NM_002814 |
| uc061llc.1 | PTCD3 | pentatricopeptide repeat domain 3 (PTCD3), (NM_017952) | NM_017952 |
| uc064qsd.1 | PTK2 | protein tyrosine kinase 2 (PTK2), var 1, (NM_153831) | NM_153831 |
| uc064prv.1 | RAD21 | RAD21 homolog (*S. pombe*) (RAD21), (NM_006265) | NM_006265 |
| uc064prx.1 | RAD21 | RAD21 homolog (*S. pombe*) (RAD21), (NM_006265) | NM_006265 |
| uc064prz.1 | RAD21 | RAD21 homolog (*S. pombe*) (RAD21), (NM_006265) | NM_006265 |
| uc057dbv.1 | RAP1GAP | RAP1 GTPase activating protein (RAP1GAP), var 2, (NM_001145657) | NM_001145657 |
| uc061hzp.1 | RASGRP3 | RAS guanyl releasing protein 3 (calcium and DAG-regulated) (RASGRP3), var 1, | NM_001139488 |
| uc058zkt.1 | RBM23 | RNA binding motif protein 23 (RBM23), var 3, (NM_001077352)(NM_001139488) | NM_001077352 |
| uc061wqt.1 | RBM39 | RNA binding motif protein 39 (RBM39), var 4, (NM_001242600) | NM_001242600 |
| uc064rzc.1 | RCL1 | RNA terminal phosphate cyclase-like 1 (RCL1), var 4, (NM_001286701) | NM_001286701 |
| uc061mtr.1 | RGPD5 | RANBP2-like and GRIP domain containing 5 (RGPD5), var 2, (NM_032260) | NM_032260 |
| uc061mvu.1 | RGPD5 | RANBP2-like and GRIP domain containing 5 (RGPD5), var 2, (NM_032260) | NM_032260 |
| uc061mzr.1 | RGPD5 | RANBP2-like and GRIP domain containing 5 (RGPD5), var 1, (NM_005054) | NM_005054 |
| uc060kjr.1 | RHBDF2 | rhomboid 5 homolog 2 (*Drosophila*) (RHBDF2), var 2, (NM_001005498) | NM_001005498 |
| uc061xqv.1 | RNF114 | ring finger protein 114 (RNF114), (NM_018683) | NM_018683 |
| uc063rej.1 | RNF146 | ring finger protein 146 (RNF146), var 2, (NM_030963) | NM_030963 |
| uc063aih.1 | RNF175 | ring finger protein 175 (RNF175), (NM_173662) | NM_173662 |
| uc064bfc.1 | RNF216 | ring finger protein 216 (RNF216), var 2, (NM_207116) | NM_207116 |
| uc060qax.1 | RP11-169F17.1 | uncharacterized LOC400655 (LOC400655), long non-coding RNA. (NR_034133) | NR_034133 |
| uc060pzv.1 | RP11-4104.1 | uncharacterized LOC101927481 (LOC101927481), long non-coding RNA. (NR_126336) | NR_126336 |
| uc063sys.1 | RP11-503C24.4 | uncharacterized LOC101929420 (LOC101929420), long non-coding RNA. (NR_110870) | NR_110870 |
| uc062rnb.1 | RP11-699L21.1 | Juncharacterized LOC647323 (LOC647323), long non-coding RNA. (NR_033944) | NR_033944 |
| uc064bkz.1 | RPA3 | replication protein A3, 14 kDa (RPA3), (NM_002947) | NM_002947 |
| uc057dsu.1 | RPS6KA1 | ribosomal protein S6 kinase, 90 kDa, polypeptide 1 (RPS6KA1), var 2, (NM_001006665) | NM_001006665 |
| uc062pjp.1 | RSRC1 | arginine/serine-rich coiled-coil 1 (RSRC1), var 2, (NM_016625) | NM_016625 |
| uc060yco.1 | RYR1 | ryanodine receptor 1 (skeletal) (RYR1), var 2, (NM_001042723) | NM_001042723 |
| uc060sbg.1 | SAFB2 | scaffold attachment factor B2 (SAFB2), (NM_014649) | NM_014649 |
| uc058suy.1 | SART3 | squamous cell carcinoma antigen recognized by T cells 3 (SART3), (NM_014706) | NM_014706 |
| uc010igm.4 | SCFD2 | sec1 family domain containing 2 (SCFD2), (NM_152540) | NM_152540 |
| uc062wpk.1 | SCFD2 | sec1 family domain containing 2 (SCFD2), (NM_152540) | NM_152540 |
| uc002nxo.3 | SCN1B | sodium channel, voltage gated, type I beta subunit (SCN1B), var b, (NM_199037) | NM_199037 |
| uc003bdt.3 | SCUBE1 | signal peptide, CUB domain, EGF-like 1 (SCUBE1), (NM_173050) | NM_173050 |
| uc060pwd.1 | SERPINB11 | serpin peptidase inhibitor, clade B (ovalbumin), member 11 (gene/pseudogene) (SERPINB11), var 1, (NM_080475) | NM_080475 |
| uc064wgj.1 | SET | SET nuclear proto-oncogene (SET), var 4, (NM_001248001) | NM_001248001 |
| uc002uuf.4 | SF3B1 | splicing factor 3b, subunit 1, 155 kDa (SF3B1), var 2, (NM_001005526) | NM_001005526 |
| uc057tgj.1 | SGMS1 | sphingomyelin synthase 1 (SGMS1), (NM_147156) | NM_147156 |
| uc062hby.1 | SH3BP5 | SH3-domain binding protein 5 (BTK-associated) (SH3BP5), var 2, (NM_001018009) | NM_001018009 |
| uc064qjw.1 | SLA | Src-like-adaptor (SLA), var 3, (NM_006748) | NM_006748 |
| uc064qjy.1 | SLA | Src-like-adaptor (SLA), var 1, (NM_001045556) | NM_001045556 |
| uc064qkc.1 | SLA | Src-like-adaptor (SLA), var 3, (NM_006748) | NM_006748 |
| uc057jmz.1 | SLC16A1 | solute carrier family 16 (monocarboxylate transporter), member 1 (SLC16A1), var 1, (NM_003051) | NM_003051 |
| uc058mzf.1 | SLC38A2 | solute carrier family 38, member 2 (SLC38A2), var 1, (NM_018976) | NM_018976 |
| uc058mzi.1 | SLC38A2 | solute carrier family 38, member 2 (SLC38A2), var 1, (NM_018976) | NM_018976 |
| uc064yxk.1 | SLC38A5 | solute carrier family 38, member 5 (SLC38A5), (NM_033518) | NM_033518 |
| uc061ioc.1 | SLC8A1 | solute carrier family 8 (sodium/calcium exchanger), member 1 (SLC8A1), var D, (NM_001112802) | NM_001112802 |
| uc061inw.1 | SLC8A1-AS1 | SLC8A1 antisense RNA 1 (SLC8A1-AS1), long non-coding RNA. (NR_038441) | NR_038441 |
| uc060pfc.1 | SMAD4 | SMAD family member 4 (SMAD4), (NM_005359) | NM_005359 |
| uc057ffg.1 | SMAP2 | small ArfGAP2 (SMAP2), var 3, (NM_001198978) | NM_001198978 |

TABLE 5-continued

| GeneName | Symbol | Description | RefSeq |
|---|---|---|---|
| uc064azr.1 | SNX8 | sorting nexin 8 (SNX8), (NM_013321) | NM_013321 |
| uc061zrd.1 | SON | SON DNA binding protein (SON), var h, (NM_001291412) | NM_001291412 |
| uc060hns.1 | SPAG9 | sperm associated antigen 9 (SPAG9), var 1, (NM_001130528) | NM_001130528 |
| uc061pgu.1 | SPC25, | SPC25, NDC80 kinetochore complex component (SPC25), (NM_020675), | NM_020675 |
| uc062fxt.1 | SPC25, | SPC25, NDC80 kinetochore complex component (SPC25), (NM_020675), | NM_020675 |
| uc010egz.2 | SPTBN4 | spectrin, beta, non-erythrocytic 4 (SPTBN4), var sigma5, (NM_025213) | NM_025213 |
| uc059dvc.1 | SPTLC2 | serine palmitoyltransferase, long chain base subunit 2 (SPTLC2), (NM_004863) | NM_004863 |
| uc062wsf.1 | SRD5A3-AS1 | SRD5A3 antisense RNA 1 (SRD5A3-AS1), long non-coding RNA. (NR_037969) | NR_037969 |
| uc062wsh.1 | SRD5A3-AS1 | SRD5A3 antisense RNA 1 (SRD5A3-AS1), long non-coding RNA. (NR_037969) | NR_037969 |
| uc062wsk.1 | SRD5A3-AS1 | SRD5A3 antisense RNA 1 (SRD5A3-AS1), long non-coding RNA. (NR_037969) | NR_037969 |
| uc057jkv.1 | ST7L | suppression of tumorigenicity 7 like (ST7L), var 4, (NM_138729) | NM_138729 |
| uc057yfa.1 | STIM1 | stromal interaction molecule 1 (STIM1), var 2, (NM_003156) | NM_003156 |
| uc061qwo.1 | STK17B | serine/threonine kinase 17b (STK17B), (NM_004226) | NM_004226 |
| uc058meu.1 | STK38L | serine/threonine kinase 38 like (STK38L), (NM_015000) | NM_015000 |
| uc058mev.1 | STK38L | serine/threonine kinase 38 like (STK38L), (NM_015000) | NM_015000 |
| uc058mey.1 | STK38L | serine/threonine kinase 38 like (STK38L), (NM_015000) | NM_015000 |
| uc061xgx.1 | STK4 | serine/threonine kinase 4 (STK4), (NM_006282) | NM_006282 |
| uc062uwr.1 | STX18-AS1 | STX18 antisense RNA 1 (head to head) (STX18-AS1), long non-coding RNA. (NR_037888) | NR_037888 |
| uc057ivy.1 | STXBP3 | syntaxin binding protein 3 (STXBP3), (NM_007269) | NM_007269 |
| uc064mdp.1 | TACC1 | transforming, acidic coiled-coil containing protein 1 (TACC1), var 2, (NM_001122824) | NM_001122824 |
| uc001hni.3 | TAF1A | TATA box binding protein (TBP)-associated factor, RNA polymerase I, A, 48 kDa (TAF1A), var 2, (NM_139352) | NM_139352 |
| uc009xdz.2 | TAF1A | TATA box binding protein (TBP)-associated factor, RNA polymerase I, A, 48 kDa (TAF1A), var 3, (NM_001201536) | NM_001201536 |
| uc058gnb.1 | TAF1D | TATA box binding protein (TBP)-associated factor, RNA polymerase I, D, 41 kDa (TAF1D), (NM_024116) | NM_024116 |
| uc064pue.1 | TAF2 | TAF2 RNA polymerase II, TATA box binding protein (TBP)-associated factor, 150 kDa (TAF2), (NM_003184) | NM_003184 |
| uc003jhy.5 | TARS | threonyl-tRNA synthetase (TARS), var 1, (NM_152295) | NM_152295 |
| uc011ksx.3 | TAS2R40 | taste receptor, type 2, member 40 (TAS2R40), (NM_176882) | NM_176882 |
| uc062qcl.1 | TBL1XR1 | transducin (beta)-like 1 X-linked receptor 1 (TBL1XR1), (NM_024665) | NM_024665 |
| uc065ajb.1 | TCEAL2 | transcription elongation factor A (SII)-like 2 (TCEAL2), (NM_080390) | NM_080390 |
| uc001tlo.2 | TCP11L2 | t-complex 11, testis-specific-like 2 (TCP11L2), var 2, (NM_001286262) | NM_001286262 |
| uc059efo.1 | TDP1 | tyrosyl-DNA phosphodiesterase 1 (TDP1), var 1, (NM_018319) | NM_018319 |
| uc058yod.1 | TFDP1 | transcription factor Dp-1 (TFDP1), var 1, (NM_007111) | NM_007111 |
| uc057eud.1 | THRAP3 | thyroid hormone receptor associated protein 3 (THRAP3), (NM_005119) | NM_005119 |
| uc059adq.1 | TINF2 | TERF1 (TRF1)-interacting nuclear factor 2 (TINF2), var 1, (NM_001099274) | NM_001099274 |
| uc064twg.1 | TLE4 | transducin-like enhancer of split 4 (TLE4), var 4, (NM_001282753) | NM_001282753 |
| uc063asb.1 | TMA16 | translation machinery associated 16 homolog (S. cerevisiae) (TMA16), (NM_018352) | NM_018352 |
| uc063asc.1 | TMA16 | translation machinery associated 16 homolog (S. cerevisiae) (TMA16), (NM_018352) | NM_018352 |
| uc063asf.1 | TMA16 | translation machinery associated 16 homolog (S. cerevisiae) (TMA16), (NM_018352) | NM_018352 |
| uc058nsk.1 | TMBIM6 | transmembrane BAX inhibitor motif containing 6 (TMBIM6), var 1, (NM_003217) | NM_003217 |
| uc058nsl.1 | TMBIM6 | transmembrane BAX inhibitor motif containing 6 (TMBIM6), var 1, (NM_003217) | NM_003217 |
| uc062ntk.1 | TMCC1-AS1 | TMCC1 antisense RNA 1 (head to head) (TMCC1-AS1), long non-coding RNA. (NR_037893) | NR_037893 |
| uc060xfi.1 | TMEM147-AS1 | TMEM147 antisense RNA 1 (TMEM147-AS1), long non-coding RNA. (NR_038396) | NR_038396 |
| uc032wlm.2 | TMEM14B | transmembrane protein 14B (TMEM14B), var 5, (NM_001286489) | NM_001286489 |
| uc032bmk.2 | TMEM179, | transmembrane protein 179 (TMEM179), var 1, (NM_001286389), | NM_001286389 |
| uc032bov.2 | TMEM179, | transmembrane protein 179 (TMEM179), var 1, (NM_001286389), | NM_001286389 |
| uc064axw.1 | TMEM184A | transmembrane protein 184A (TMEM184A), (NM_001097620) | NM_001097620 |
| uc058ssh.1 | TMEM263 | transmembrane protein 263 (TMEM263), (NM_152261) | NM_152261 |
| uc063elp.1 | TNPO1 | transportin 1 (TNPO1), var 2, (NM_153188) | NM_153188 |
| uc060uxb.1 | TPM4 | tropomyosin 4 (TPM4), var Tpm4.1, (NM_001145160) | NM_001145160 |
| uc057nyz.1 | TPR | translocated promoter region, nuclear basket protein (TPR), (NM_003292) | NM_003292 |
| uc059qbo.1 | TRAP1 | TNF receptor-associated protein 1 (TRAP1), var 1, (NM_016292) | NM_016292 |
| uc060ogn.1 | TRAPPC8 | trafficking protein particle complex 8 (TRAPPC8), (NM_014939) | NM_014939 |
| uc063aho.1 | TRIM2 | tripartite motif containing 2 (TRIM2), var 1, (NM_015271) | NM_015271 |
| uc003npt.4 | TRIM26, | tripartite motif containing 26 (TRIM26), var 2, (NM_001242783), | NM_001242783 |
| uc011ekv.3 | TRIM26, | tripartite motif containing 26 (TRIM26), var 2, (NM_001242783), | NM_001242783 |
| uc011exm.3 | TRIM26, | tripartite motif containing 26 (TRIM26), var 2, (NM_001242783), | NM_001242783 |
| uc011fvz.3 | TRIM26, | tripartite motif containing 26 (TRIM26), var 2, (NM_001242783), | NM_001242783 |
| uc011gsc.3 | TRIM26, | tripartite motif containing 26 (TRIM26), var 2, (NM_001242783), | NM_001242783 |
| uc011iib.3 | TRIM26, | tripartite motif containing 26 (TRIM26), var 2, (NM_001242783), | NM_001242783 |
| uc011jff.3 | TRIM26, | tripartite motif containing 26 (TRIM26), var 2, (NM_001242783), | NM_001242783 |
| uc063mqn.1 | TRIM26, | tripartite motif containing 26 (TRIM26), var 1, (NM_003449), | NM_003449 |
| uc063tev.1 | TRIM26, | tripartite motif containing 26 (TRIM26), var 1, (NM_003449), | NM_003449 |
| uc063val.1 | TRIM26, | tripartite motif containing 26 (TRIM26), var 1, (NM_003449), | NM_003449 |
| uc063wga.1 | TRIM26, | tripartite motif containing 26 (TRIM26), var 1, (NM_003449), | NM_003449 |
| uc063ylg.1 | TRIM26, | tripartite motif containing 26 (TRIM26), var 1, (NM_003449), | NM_003449 |
| uc063zra.1 | TRIM26, | tripartite motif containing 26 (TRIM26), var 1, (NM_003449), | NM_003449 |
| uc010mif.3 | TTC39B | tetratricopeptide repeat domain 39B (TTC39B), var 1, (NM_152574) | NM_152574 |
| uc059ehr.1 | TTC7B | tetratricopeptide repeat domain 7B (TTC7B), (NM_001010854) | NM_001010854 |
| uc061qea.1 | TTN-AS1 | TTN antisense RNA 1 (TTN-AS1), var 1, long non-coding RNA. (NR_038272) | NR_038272 |
| uc061qey.1 | TTN-AS1 | TTN antisense RNA 1 (TTN-AS1), var 1, long non-coding RNA. (NR_038272) | NR_038272 |
| uc031utq.2 | TXNIP | thioredoxin interacting protein (TXNIP), (NM_006472) | NM_006472 |
| uc057kcm.1 | TXNIP | thioredoxin interacting protein (TXNIP), (NM_006472) | NM_006472 |
| uc062oqr.1 | U2SURP | U2 snRNP-associated SURP domain containing (U2SURP), (NM_001080415) | NM_001080415 |
| uc003epa.5 | UBA5 | ubiquitin-like modifier activating enzyme 5 (UBA5), var 1, (NM_024818) | NM_024818 |
| uc058uys.1 | UBC | ubiquitin C (UBC), (NM_021009) | NM_021009 |

TABLE 5-continued

| GeneName | Symbol | Description | RefSeq |
|---|---|---|---|
| uc059igw.1 | UBR1 | ubiquitin protein ligase E3 component n-recognin 1 (UBR1), (NM_174916) | NM_174916 |
| uc064nbb.1 | UBXN2B | UBX domain protein 2B (UBXN2B), (NM_001077619) | NM_001077619 |
| uc061oai.1 | UBXN4 | UBX domain protein 4 (UBXN4), (NM_014607) | NM_014607 |
| uc060vud.1 | UPF1 | UPF1 regulator of nonsense transcripts homolog (yeast) (UPF1), var 2, (NM_002911) | NM_002911 |
| uc058hmj.1 | USP28 | ubiquitin specific peptidase 28 (USP28), var 2, (NM_001301029) | NM_001301029 |
| uc058hmk.1 | USP28 | ubiquitin specific peptidase 28 (USP28), var 2, (NM_001301029) | NM_001301029 |
| uc061jni.1 | USP34 | ubiquitin specific peptidase 34 (USP34), (NM_014709) | NM_014709 |
| uc003ija.5 | USP38 | ubiquitin specific peptidase 38 (USP38), var 2, (NM_001290325) | NM_001290325 |
| uc059jdr.1 | USP8 | ubiquitin specific peptidase 8 (USP8), var 1, (NM_005154) | NM_005154 |
| uc059dud.1 | VIPAS39 | VPS33B interacting protein, apical-basolateral polarity regulator, spe-39 homolog (VIPAS39), var 3, (NM_001193315) | NM_001193315 |
| uc004dwh.3 | VSIG4 | V-set and immunoglobulin domain containing 4 (VSIG4), var 1, (NM_007268) | NM_007268 |
| uc004dwi.3 | VSIG4 | V-set and immunoglobulin domain containing 4 (VSIG4), var 2, (NM_001100431) | NM_001100431 |
| uc064zqm.1 | VSIG4 | V-set and immunoglobulin domain containing 4 (VSIG4), var 5, (NM_001257403) | NM_001257403 |
| uc062vdz.1 | WDR1 | WD repeat domain 1 (WDR1), var 2, (NM_005112) | NM_005112 |
| uc062jnz.1 | WDR6 | WD repeat domain 6 (WDR6), (NM_018031) | NM_018031 |
| uc062joj.1 | WDR6 | WD repeat domain 6 (WDR6), (NM_018031) | NM_018031 |
| uc001dcx.5 | WDR78 | WD repeat domain 78 (WDR78), var 1, (NM_024763) | NM_024763 |
| uc059sly.1 | XPO6 | exportin 6 (XPO6), var 2, (NM_015171) | NM_015171 |
| uc061seo.1 | XRCC5 | X-ray repair complementing defective repair in Chinese hamster cells 5 (double-strand-break rejoining) (XRCC5), (NM_021141) | NM_021141 |
| uc064pcw.1 | YWHAZ | tyrosine 3-monooxygenase/tryptophan 5-monooxygenase activation protein, zeta (YWHAZ), var 6, (NM_001135702) | NM_001135702 |
| uc059qwt.1 | ZC3H7A | zinc finger CCCH-type containing 7A (ZC3H7A), (NM_014153) | NM_014153 |
| uc058rek.1 | ZDHHC17 | zinc finger, DHHC-type containing 17 (ZDHHC17), (NM_015336) | NM_015336 |
| uc002nni.3 | ZNF101 | zinc finger protein 101 (ZNF101), var 1, (NM_033204) | NM_033204 |
| uc060zrn.1 | ZNF112 | zinc finger protein 112 (ZNF112), var 2, (NM_013380) | NM_013380 |
| uc010qev.3 | ZNF33A | zinc finger protein 33A (ZNF33A), var 3, (NM_001278170) | NM_001278170 |
| uc010ary.3 | ZNF410 | zinc finger protein 410 (ZNF410), var 3, (NM_001242926) | NM_001242926 |
| uc061doh.1 | ZNF417 | zinc finger protein 417 (ZNF417), var 1, (NM_152475) | NM_152475 |
| uc063pft.1 | ZNF451 | zinc finger protein 451 (ZNF451), var 2, (NM_015555) | NM_015555 |
| uc063pfw.1 | ZNF451 | zinc finger protein 451 (ZNF451), var 2, (NM_015555) | NM_015555 |
| uc061djm.1 | ZNF548 | zinc finger protein 548 (ZNF548), var 1, (NM_001172773) | NM_001172773 |
| uc060syy.1 | ZNF559-ZNF177 | ZNF559-ZNF177 readthrough (ZNF559-ZNF177), var 2, (NM_001172650) | NM_001172650 |
| uc060szi.1 | ZNF559-ZNF177 | ZNF559-ZNF177 readthrough (ZNF559-ZNF177), var 2, (NM_001172650) | NM_001172650 |
| uc061cav.1 | ZNF614 | zinc finger protein 614 (ZNF614), (NM_025040) | NM_025040 |
| uc010sls.3 | ZNF641 | zinc finger protein 641 (ZNF641), var 3, (NM_001172682) | NM_001172682 |
| uc064tmp.1 | ZNF658 | zinc finger protein 658 (ZNF658), (NM_033160) | NM_033160 |
| uc001ice.3 | ZNF669 | zinc finger protein 669 (ZNF669), var 1, (NM_024804) | NM_024804 |
| uc062huj.1 | ZNF860 | zinc finger protein 860 (ZNF860), (NM_001137674) | NM_001137674 |
| uc060wkk.1 | ZNF91 | zinc finger protein 91 (ZNF91), var 1, (NM_003430) | NM_003430 |
| uc060wdl.1 | ZNF93 | zinc finger protein 93 (ZNF93), (NM_031218) | NM_031218 |

TABLE 6

| GeneName | Symbol | Description | RefSeq |
|---|---|---|---|
| uc061drv.1 | A1BG | alpha-1-B glycoprotein (A1BG), (from RefSeq NM_130786) | NM_130786 |
| uc057ilc.1 | ABCA4 | ATP-binding cassette, sub-family A (ABC1), member 4 (ABCA4), (from RefSeq NM_000350) | NM_000350 |
| uc003wjo.3 | ABCF2 | ATP-binding cassette, sub-family F (GCN20), member 2 (ABCF2), var2, (from RefSeq NM_005692) | NM_005692 |
| uc064bvu.1 | AC099342.1 | uncharacterized LOC101927769, long non-coding RNA | NR_110117 |
| uc059xhj.1 | ADAT1 | adenosine deaminase, tRNA-specific 1 (ADAT1), var1, (from RefSeq NM_012091) | NM_012091 |
| uc021xqj.2 | ADH7 | alcohol dehydrogenase 7 (class IV), mu or sigma polypeptide (ADH7), var1, (from RefSeq NM_001166504) | NM_001166504 |
| uc063bvy.1 | AHRR | aryl-hydrocarbon receptor repressor (AHRR), var2, (from RefSeq NM_001242412) | NM_001242412 |
| uc063bvz.1 | AHRR | aryl-hydrocarbon receptor repressor (AHRR), var2, (from RefSeq NM_001242412) | NM_001242412 |
| uc062jar.1 | ALS2CL | ALS2 C-terminal like | NR_033815 |
| uc064mjf.1 | AP3M2 | adaptor-related protein complex 3, mu 2 subunit (AP3M2), var2, (from RefSeq NM_006803) | NM_006803 |
| uc001mdb.4 | APBB1 | amyloid beta (A4) precursor protein-binding, family B, member 1 (Fe65) (APBB1), var1, (from RefSeq NM_001164) | NM_001164 |
| uc001mdc.3 | APBB1 | amyloid beta (A4) precursor protein-binding, family B, member 1 (Fe65) (APBB1), var2, (from RefSeq NM_145689) | NM_145689 |
| uc057yjv.1 | APBB1 | amyloid beta (A4) precursor protein-binding, family B, member 1 (Fe65) (APBB1), var1, (from RefSeq NM_001164) | NM_001164 |
| uc057yjz.1 | APBB1 | amyloid beta (A4) precursor protein-binding, family B, member 1 (Fe65) (APBB1), var1, (from RefSeq NM_001164) | NM_001164 |
| uc057ykd.1 | APBB1 | amyloid beta (A4) precursor protein-binding, family B, member 1 (Fe65) (APBB1), var6, (from RefSeq NM_001257320) | NM_001257320 |
| uc062dsw.1 | APOL4 | apolipoprotein L, 4 (APOL4), vara, (from RefSeq NM_030643) | NM_030643 |
| uc064snu.1 | APTX | ataxin | NR_036576 |
| uc064soc.1 | APTX | ataxin | NR_036577 |
| uc065ahz.1 | ARMCX6 | armadillo repeat containing, X-linked 6 (ARMCX6), var3, (from RefSeq NM_001184768) | NM_001184768 |

TABLE 6-continued

| GeneName | Symbol | Description | RefSeq |
|---|---|---|---|
| uc064pgy.1 | AZIN1-AS1 | AZIN1 antisense RNA 1 | NR_126339 |
| uc059ulu.1 | BBS2 | Bardet-Biedl syndrome 2 (BBS2), (from RefSeq NM_031885) | NM_031885 |
| uc061wwa.1 | BLCAP | bladder cancer associated protein (BLCAP), var2, (from RefSeq NM_001167820) | NM_001167820 |
| uc058bon.1 | C11orf31 | chromosome 11 open reading frame 31 (C11orf31), (from RefSeq NM_170746) | NM_170746 |
| uc059tos.1 | C16orf58 | chromosome 16 open reading frame 58 (C16orf58), (from RefSeq NM_022744) | NM_022744 |
| uc063kor.1 | C5ORF60 | chromosome 5 open reading frame 60 | NR_131066 |
| uc063nqr.1 | C6orf10, | chromosome 6 open reading frame 10 (C6orf10), var2, (from RefSeq NM_001286474), | NM_001286474 |
| uc064rtg.1 | CBWD1 | COBW domain containing 1 (CBWD1), var1, (from RefSeq NM_018491) | NM_018491 |
| uc064bwy.1 | CDCA7L | cell division cycle associated 7-like (CDCA7L), var2, (from RefSeq NM_001127370) | NM_001127370 |
| uc059xrj.1 | CDH13 | cadherin 13 (CDH13), var5, (from RefSeq NM_001220491) | NM_001220491 |
| uc061mig.1 | CHST10 | carbohydrate sulfotransferase 10 (CHST10), (from RefSeq NM_004854) | NM_004854 |
| uc062hvi.1 | CNOT10 | CCR4-NOT transcription complex subunit 10 | NR_046352 |
| uc064rqz.1 | COMMD5 | COMM domain containing 5 (COMMD5), var3, (from RefSeq NM_001081004) | NM_001081004 |
| uc057ugl.1 | COMTD1 | catechol-O-methyltransferase domain containing 1 (COMTD1), (from RefSeq NM_144589) | NM_144589 |
| uc001tyn.4 | COQ5 | coenzyme Q5 homolog, methyltransferase (S. cerevisiae) (COQ5), (from RefSeq NM_032314) | NM_032314 |
| uc062lwg.1 | CPOX | coproporphyrinogen oxidase (CPOX), (from RefSeq NM_000097) | NM_000097 |
| uc010rgn.2 | CRY2 | cryptochrome circadian clock 2 (CRY2), var1, (from RefSeq NM_021117) | NM_021117 |
| uc058ato.1 | CRY2 | cryptochrome circadian clock 2 (CRY2), var1, (from RefSeq NM_021117) | NM_021117 |
| uc057oir.1 | CSRP1 | cysteine-rich protein | NM_001193570 |
| uc062ukk.1 | CTBP1 | C-terminal binding protein 1 (CTBP1), var2, (from RefSeq NM_001012614) | NM_001012614 |
| uc059zqi.1 | CTNS | cystinosin, lysosomal cystine transporter (CTNS), var2, (from RefSeq NM_004937) | NM_004937 |
| uc057jkc.1 | CTTNBP2NL | CTTNBP2 N-terminal like (CTTNBP2NL), (from RefSeq NM_018704) | NM_018704 |
| uc061otq.1 | CYTIP | cytohesin 1 interacting protein (CYTIP), (from RefSeq NM_004288) | NM_004288 |
| uc058mlq.1 | DDX11 | DEAD/H (Asp-Glu-Ala-Asp/His) box helicase 11 (DDX11), var5, (from RefSeq NM_001257145) | NM_001257145 |
| uc060zfv.1 | DEDD2 | death effector domain containing 2 | NR_073051 |
| uc021wlp.2 | DGCR8 | DGCR8 microprocessor complex subunit (DGCR8), var2, (from RefSeq NM_001190326) | NM_001190326 |
| uc058pdy.1 | DGKA | diacylglycerol kinase, alpha 80 kDa (DGKA), var4, (from RefSeq NM_201554) | NM_201554 |
| uc062jfe.1 | DHX30 | DEAH (Asp-Glu-Ala-His) box helicase 30 (DHX30), var1, (from RefSeq NM_138615) | NM_138615 |
| uc059kmk.1 | DIS3L | DIS3 like exosome 3'-5' exoribonuclease (DIS3L), var2, (from RefSeq NM_133375) | NM_133375 |
| uc062seb.1 | DLG1 | discs, large homolog 1 (Drosophila) (DLG1), var3, (from RefSeq NM_001204386) | NM_001204386 |
| uc061cxr.1 | DNAAF3 | dynein, axonemal, assembly factor 3 (DNAAF3), var1, (from RefSeq NM_001256714) | NM_001256714 |
| uc010wnn.2 | DYNLL2 | dynein, light chain, LC8-type 2 (DYNLL2), (from RefSeq NM_080677) | NM_080677 |
| uc059soq.1 | EIF3CL | eukaryotic translation initiation factor 3, subunit C-like (EIF3CL), (from RefSeq NM_001099661) | NM_001099661 |
| uc002gnz.5 | ELAC2 | elaC ribonuclease Z 2 | NM_018127 |
| uc057gll.1 | EPS15 | epidermal growth factor receptor pathway substrate 15 (EPS15), var1, (from RefSeq NM_001981) | NM_001981 |
| uc059fov.1 | EXOC3L4 | exocyst complex component 3-like 4 (EXOC3L4), (from RefSeq NM_001077594) | NM_001077594 |
| uc060vkb.1 | FAM129C | family with sequence similarity 129, member C (FAM129C), var2, (from RefSeq NM_001098524) | NM_001098524 |
| uc057bod.1 | FAM213B | family with sequence similarity 213, member B (FAM213B), var2, (from RefSeq NM_152371), | NM_152371 |
| uc061fvb.1 | FAM213B, | family with sequence similarity 213, member B (FAM213B), var2, (from RefSeq NM_152371), | NM_152371 |
| uc064tfh.1 | FAM95B1, | family with sequence similarity 95, member B1 (FAM95B1), long non-coding RNA. (from RefSeq NR_026759), | NR_026759 |
| uc060std.1 | FBN3 | fibrillin 3 (FBN3), (from RefSeq NM_032447) | NM_032447 |
| uc058fep.1 | FCHSD2 | FCH and double SH3 domains 2 (FCHSD2), (from RefSeq NM_014824) | NM_014824 |
| uc064glm.1 | FIS1 | fission 1 (mitochondrial outer membrane) homolog (S. cerevisiae) (FIS1), (from RefSeq NM_016068) | NM_016068 |
| uc003djj.3 | FLNB | filamin B, beta (FLNB), var2, (from RefSeq NM_001457) | NM_001457 |
| uc010hnf.3 | FLNB | filamin B, beta (FLNB), var4, (from RefSeq NM_001164319) | NM_001164319 |
| uc064mnv.1 | FNTA | farnesyltransferase, CAAX box, alpha (FNTA), var1, (from RefSeq NM_002027) | NM_002027 |
| uc063okh.1 | FOXP4-AS1 | FOXP4 antisense RNA 1 | NR_126417 |
| uc060atq.1 | FXR2 | fragile X mental retardation, autosomal homolog 2 (FXR2), (from RefSeq NM_004860) | NM_004860 |
| uc004doi.6 | GAGE13 | G antigen 2C (GAGE2C), (from RefSeq NM_001472) | NM_001472 |
| uc059yvw.1 | GAS8 | growth arrest-specific 8 (GAS8), var4, (from RefSeq NM_001286208) | NM_001286208 |
| uc062dbe.1 | GATSL3 | GATS protein-like 3 (GATSL3), (from RefSeq NM_001037666) | NM_001037666 |
| uc002whp.2 | GNRH2 | gonadotropin-releasing hormone 2 (GNRH2), var3, (from RefSeq NM_178331) | NM_178331 |
| uc057dtw.1 | GPATCH3 | G patch domain containing 3 (GPATCH3), (from RefSeq NM_022078) | NM_022078 |
| uc059uvj.1 | GPR56 | adhesion G protein-coupled receptor G1 (ADGRG1), var7, (from RefSeq NM_001145774) | NM_001145774 |
| uc064roh.1 | GPT | glutamic-pyruvate transaminase (alanine aminotransferase) (GPT), (from RefSeq NM_005309) | NM_005309 |
| uc063ixf.1 | GRIA1 | glutamate receptor, ionotropic, AMPA 1 (GRIA1), var7, (from RefSeq NM_001258023) | NM_001258023 |
| uc002iii.2 | HEXIM2 | hexamethylene bis-acetamide inducible 2 | NM_001303442 |
| uc061afd.1 | HIF3A | hypoxia inducible factor 3, alpha subunit (HIF3A), var4, (from RefSeq NM_152796) | NM_152796 |
| uc058uor.1 | HIP1R | huntingtin interacting protein 1 related (HIP1R), var1, (from RefSeq NM_003959) | NM_003959 |
| uc061yty.1 | ICOSLG | inducible T-cell costimulator ligand | NM_001283052 |
| uc058pgk.1 | IKZF4 | IKAROS family zinc finger 4 (Eos) (IKZF4), (from RefSeq NM_022465) | NM_022465 |
| uc063ljh.1 | IRF4 | interferon regulatory factor 4 | NM_001195286 |
| uc061nqc.1 | IWS1 | IWS1 homolog (S. cerevisiae) (IWS1), (from RefSeq NM_017969) | NM_017969 |
| uc063hbv.1 | JADE2 | jade family PHD finger 2 (JADE2), var3, (from RefSeq NM_015288) | NM_015288 |
| uc062lig.1 | KBTBD8 | kelch repeat and BTB (POZ) domain containing 8 (KBTBD8), (from RefSeq NM_032505) | NM_032505 |
| uc064zso.1 | KIF4A | kinesin family member 4A (KIF4A), (from RefSeq NM_012310) | NM_012310 |
| uc057ohz.1 | LAD1 | ladinin 1 (LAD1), (from RefSeq NM_005558) | NM_005558 |
| uc063epk.1 | LINC01336 | long intergenic non-protein coding RNA 1336 (LINC01336), long non-coding RNA. (from RefSeq NR_126375) | NR_126375 |
| uc063ady.1 | LRBA | LPS-responsive vesicle trafficking, beach and anchor containing (LRBA), var2, (from RefSeq NM_006726) | NM_006726 |
| uc058kne.1 | LRRC23 | leucine rich repeat containing 23 (LRRC23), var2, (from RefSeq NM_006992) | NM_006992 |

TABLE 6-continued

| GeneName | Symbol | Description | RefSeq |
|---|---|---|---|
| uc060ltc.1 | LRRC45 | leucine rich repeat containing 45 (LRRC45), (from RefSeq NM_144999) | NM_144999 |
| uc063ecv.1 | MAST4 | microtubule associated serine/threonine kinase family member 4 (MAST4), var4, (from RefSeq NM_001290226) | NM_001290226 |
| uc062pue.1 | MECOM | MDS1 and EVI1 complex locus (MECOM), var3, (from RefSeq NM_001105078) | NM_001105078 |
| uc032ylk.1 | MIR3135B | microRNA 3135b (MIR3135B), microRNA. (from RefSeq NR_039668), | NR_039668 |
| uc032ytr.1 | MIR3135B | microRNA 3135b (MIR3135B), microRNA. (from RefSeq NR_039668), | NR_039668 |
| uc021uqm.1 | MIR3188 | microRNA 3188 (MIR3188), microRNA. (from RefSeq NR_036155) | NR_036155 |
| uc058vgw.1 | MMP17 | matrix metallopeptidase 17 (membrane-inserted) (MMP17), (from RefSeq NM_016155) | NM_016155 |
| uc063sgp.1 | MTHFD1L | methylenetetrahydrofolate dehydrogenase (NADP+ dependent) 1-like (MTHFD1L), var3, (from RefSeq NM_001242768) | NM_001242768 |
| uc060ehm.1 | MYO19 | myosin XIX (MYO19), var3, (from RefSeq NM_001033580) | NM_001033580 |
| uc064kqr.1 | NAT1 | N-acetyltransferase 1 (arylamine N-acetyltransferase) (NAT1), var4, (from RefSeq NM_001160173) | NM_001160173 |
| uc057jyz.1 | NBPF15 | neuroblastoma breakpoint family, member 15 (NBPF15), var2, (from RefSeq NM_173638) | NM_173638 |
| uc057jza.1 | NBPF15 | neuroblastoma breakpoint family, member 15 (NBPF15), var2, (from RefSeq NM_173638) | NM_173638 |
| uc061end.1 | NLRP2 | NLR family, pyrin domain containing 2 (NLRP2), var2, (from RefSeq NM_001174081) | NM_001174081 |
| uc061ctz.1 | NLRP7 | NLR family, pyrin domain containing 7 (NLRP7), var3, (from RefSeq NM_001127255), | NM_001127255 |
| uc061foc.1 | NLRP7 | NLR family, pyrin domain containing 7 (NLRP7), var3, (from RefSeq NM_001127255), | NM_001127255 |
| uc061var.1 | NOP56 | NOP56 ribonucleoprotein (NOP56), var1, (from RefSeq NM_006392) | NM_006392 |
| uc061mjc.1 | NPAS2 | neuronal PAS domain protein 2 (NPAS2), (from RefSeq NM_002518) | NM_002518 |
| uc058cye.1 | NRXN2 | neurexin 2 (NRXN2), varbeta, (from RefSeq NM_138734) | NM_138734 |
| uc059six.1 | NSMCE1 | non-SMC element 1 homolog (S. cerevisiae) (NSMCE1), (from RefSeq NM_145080) | NM_145080 |
| uc021txo.2 | NT5C3B | 5'-nucleotidase, cytosolic IIIB (NT5C3B), var1, (from RefSeq NM_052935) | NM_052935 |
| uc060fdr.1 | NT5C3B | 5'-nucleotidase, cytosolic IIIB (NT5C3B), var1, (from RefSeq NM_052935) | NM_052935 |
| uc061aza.1 | NTF4 | neurotrophin 4 (NTF4), (from RefSeq NM_006179) | NM_006179 |
| uc062xlo.1 | NUP54 | nucleoporin 54 kDa | NR_103781 |
| uc062xlr.1 | NUP54 | nucleoporin 54 kDa | NR_103782 |
| uc061bmx.1 | NUP62 | nucleoporin 62 kDa (NUP62), var1, (from RefSeq NM_153719) | NM_153719 |
| uc057jvt.1 | PHGDH | phosphoglycerate dehydrogenase (PHGDH), (from RefSeq NM_006623) | NM_006623 |
| uc064dvi.1 | PHKG1 | phosphorylase kinase, gamma 1 | NR_047689 |
| uc057xni.1 | PIDD1 | p53-induced death domain protein 1 (PIDD1), var3, (from RefSeq NM_145887) | NM_145887 |
| uc059phr.1 | PKD1 | polycystic kidney disease 1 (autosomal dominant) (PKD1), var2, (from RefSeq NM_000296) | NM_000296 |
| uc059rbn.1 | PLA2G10, | phospholipase A2, group X (PLA2G10), (from RefSeq NM_003561), | NM_003561 |
| uc062iet.1 | PLCD1 | phospholipase C, delta 1 (PLCD1), var2, (from RefSeq NM_006225) | NM_006225 |
| uc061xai.1 | PLCG1 | phospholipase C, gamma 1 (PLCG1), var2, (from RefSeq NM_182811) | NM_182811 |
| uc062fel.1 | PPARA | peroxisome proliferator activated receptor alpha | NM_001001928 |
| uc063msm.1 | PPP1R10 | protein phosphatase 1 regulatory subunit 10 | NR_072994 |
| uc063twf.1 | PPP1R10 | protein phosphatase 1 regulatory subunit 10 | NR_072994 |
| uc063vcd.1 | PPP1R10 | protein phosphatase 1 regulatory subunit 10 | NR_072994 |
| uc063whs.1 | PPP1R10 | protein phosphatase 1 regulatory subunit 10 | NR_072994 |
| uc063xhb.1 | PPP1R10 | protein phosphatase 1 regulatory subunit 10 | NR_072994 |
| uc063ymx.1 | PPP1R10 | protein phosphatase 1 regulatory subunit 10 | NR_072994 |
| uc063zss.1 | PPP1R10 | protein phosphatase 1 regulatory subunit 10 | NR_072994 |
| uc063phe.1 | PRIM2 | primase, DNA, polypeptide 2 (58 kDa) (PRIM2), var1, (from RefSeq NM_000947) | NM_000947 |
| uc010vlg.3 | PRMT7 | protein arginine methyltransferase 7 (PRMT7), var2, (from RefSeq NM_001184824) | NM_001184824 |
| uc064wqo.1 | PRRC2B | proline-rich coiled-coil 2B (PRRC2B), (from RefSeq NM_013318) | NM_013318 |
| uc063mxz.1 | PSORS1C1, | psoriasis susceptibility 1 candidate 1 (PSORS1C1), (from RefSeq NM_014068), | NM_014068 |
| uc058mvt.1 | PUS7L | pseudouridylate synthase 7 homolog (S. cerevisiae)-like (PUS7L), var2, (from RefSeq NM_001098614) | NM_001098614 |
| uc058jqr.1 | RAD52 | RAD52 homolog, DNA repair protein | NM_001297421 |
| uc060sfo.1 | RANBP3 | RAN binding protein 3 (RANBP3), var4, (from RefSeq NM_001300865) | NM_001300865 |
| uc058tuf.1 | RFC5 | replication factor C subunit 5 | NM_001206801 |
| uc059xcn.1 | RFWD3 | ring finger and WD repeat domain 3 (RFWD3), (from RefSeq NM_018124) | NM_018124 |
| uc064qmg.1 | RP11-157E21.1 | uncharacterized LOC101927822 (LOC101927822), long non-coding RNA. (from RefSeq NR_125424) | NR_125424 |
| uc057vee.1 | RRP12 | ribosomal RNA processing 12 homolog (S. cerevisiae) (RRP12), var3, (from RefSeq NM_001284337) | NM_001284337 |
| uc060hiq.1 | RSAD1 | radical S-adenosyl methionine domain containing 1 (RSAD1), var1, (from RefSeq NM_018346) | NM_018346 |
| uc062oaq.1 | RYK | receptor-like tyrosine kinase (RYK), var2, (from RefSeq NM_002958) | NM_002958 |
| uc064bpk.1 | SCIN | scinderin (SCIN), var2, (from RefSeq NM_033128) | NM_033128 |
| uc063exq.1 | SERINC5 | serine incorporator 5 | NM_001174071 |
| uc062evq.1 | SERLH2 | serine hydrolase-like 2 | NR_104301 |
| uc062evt.1 | SERLH2 | serine hydrolase-like 2 | NR_104300 |
| uc062bvk.1 | SERPIND1 | serpin peptidase inhibitor, clade D (heparin cofactor), member 1 (SERPIND1), (from RefSeq NM_000185) | NM_000185 |
| uc062djs.1 | SFI1 | Sfi1 homolog, spindle assembly associated (yeast) (SFI1), var2, (from RefSeq NM_014775) | NM_014775 |
| uc001zwr.5 | SLC12A1 | solute carrier family 12 (sodium/potassium/chloride transporter), member 1 (SLC12A1), var1, (from RefSeq NM_000338) | NM_000338 |
| uc059wbp.1 | SLC12A4 | solute carrier family 12 (potassium/chloride transporter), member 4 (SLC12A4), var5, (from RefSeq NM_001145964) | NM_001145964 |
| uc064wao.1 | SLC25A25 | solute carrier family 25 (mitochondrial carrier; phosphate carrier), member 25 (SLC25A25), var1, (from RefSeq NM_052901) | NM_052901 |
| uc063fxo.1 | SLC25A46 | solute carrier family 25 member 46 | NM_001303250 |
| uc062iym.1 | SLC6A20 | solute carrier family 6 (proline IMINO transporter), member 20 (SLC6A20), var2, (from RefSeq NM_022405) | NM_022405 |
| uc002cxt.4 | SMIM22 | small integral membrane protein 22 (SMIM22), var2, (from RefSeq NM_001253791) | NM_001253791 |
| uc059qjk.1 | SMIM22 | small integral membrane protein 22 (SMIM22), var3, (from RefSeq NM_001253793) | NM_001253793 |

TABLE 6-continued

| GeneName | Symbol | Description | RefSeq |
|---|---|---|---|
| uc061ver.1 | SMOX | spermine oxidase (SMOX), var2, (from RefSeq NM_175840) | NM_175840 |
| uc057qye.1 | SMYD3 | SET and MYND domain containing 3 (SMYD3), var2, (from RefSeq NM_022743) | NM_022743 |
| uc064hsz.1 | SND1 | staphylococcal nuclease and tudor domain containing 1 (SND1), (from RefSeq NM_014390) | NM_014390 |
| uc001tfu.2 | SNORA53 | small nucleolar RNA, H/ACA box 53 (SNORA53), small nucleolar RNA. (from RefSeq NR_003015) | NR_003015 |
| uc064tit.1 | SPATA31A7 | SPATA31 subfamily A, member 7 (SPATA31A7), (from RefSeq NM_015667) | NM_015667 |
| uc063eby.1 | SREK1 | splicing regulatory glutamine/lysine-rich protein 1 (SREK1), var4, (from RefSeq NM_001270493) | NM_001270493 |
| uc058mcg.1 | SSPN | sarcospan (SSPN), var2, (from RefSeq NM_001135823) | NM_001135823 |
| uc010rnb.2 | STIP1 | stress-induced phosphoprotein 1 (STIP1), var3, (from RefSeq NM_001282653) | NM_001282653 |
| uc057jcy.1 | STRIP1 | striatin interacting protein 1 (STRIP1), var2, (from RefSeq NM_001270768) | NM_001270768 |
| uc064egv.1 | STX1A | syntaxin 1A (brain) (STX1A), var2, (from RefSeq NM_001165903) | NM_001165903 |
| uc059pdz.1 | TBL3 | transducin (beta)-like 3 (TBL3), (from RefSeq NM_006453) | NM_006453 |
| uc060rek.1 | TCF3 | transcription factor 3 (TCF3), var1, (from RefSeq NM_003200) | NM_003200 |
| uc061znt.1 | TCP10L | t-complex 10-like (TCP10L), (from RefSeq NM_144659) | NM_144659 |
| uc057kyy.1 | TDRKH | tudor and KH domain containing (TDRKH), var2, (from RefSeq NM_001083963) | NM_001083963 |
| uc060upn.1 | TECR | trans-2,3-enoyl-CoA reductase (TECR), var1, (from RefSeq NM_138501) | NM_138501 |
| uc061ojm.1 | TEX41 | testis expressed 41 (non-protein coding) (TEX41), long non-coding RNA. (from RefSeq NR_033870) | NR_033870 |
| uc061irb.1 | THADA | thyroid adenoma associated | NR_073394 |
| uc061kij.1 | TIA1 | TIA1 cytotoxic granule-associated RNA binding protein (TIA1), var2, (from RefSeq NM_022173) | NM_022173 |
| uc060vxm.1 | TMEM161A | transmembrane protein 161A (TMEM161A), var2, (from RefSeq NM_001256766) | NM_001256766 |
| uc062bjc.1 | TMEM191B | transmembrane protein 191B (TMEM191B), (from RefSeq NM_001242313) | NM_001242313 |
| uc058ssh.1 | TMEM263 | transmembrane protein 263 (TMEM263), (from RefSeq NM_152261) | NM_152261 |
| uc064ooz.1 | TMEM67 | transmembrane protein 67 | NR_024522 |
| uc064vgq.1 | TNC | tenascin C (TNC), (from RefSeq NM_002160) | NM_002160 |
| uc061duf.1 | TRIM28 | tripartite motif containing 28 (TRIM28), (from RefSeq NM_005762) | NM_005762 |
| uc058qdh.1 | TSFM | Ts translation elongation factor, mitochondrial (TSFM), var2, (from RefSeq NM_005726) | NM_005726 |
| uc062atf.1 | UBE2G2 | ubiquitin-conjugating enzyme E2G 2 (UBE2G2), var1, (from RefSeq NM_003343) | NM_003343 |
| uc058dep.1 | VPS51 | vacuolar protein sorting 51 homolog (S. cerevisiae) (VPS51), var1, (from RefSeq NM_013265) | NM_013265 |
| uc058fld.1 | XRRA1 | X-ray radiation resistance associated 1 (XRRA1), var2, (from RefSeq NM_001270380) | NM_001270380 |
| uc060pua.1 | ZCCHC2 | zinc finger, CCHC domain containing 2 (ZCCHC2), var1, (from RefSeq NM_017742) | NM_017742 |
| uc063ezp.1 | ZCCHC9 | zinc finger, CCHC domain containing 9 (ZCCHC9), var2, (from RefSeq NM_001131035) | NM_001131035 |
| uc001knl.5 | ZDHHC16 | zinc finger, DHHC-type containing 16 (ZDHHC16), var2, (from RefSeq NM_198043) | NM_198043 |
| uc057vfd.1 | ZDHHC16 | zinc finger, DHHC-type containing 16 (ZDHHC16), var7, (from RefSeq NM_001287804) | NM_001287804 |
| uc061you.1 | ZGPAT | zinc finger, CCCH-type with G patch domain (ZGPAT), var3, (from RefSeq NM_181485) | NM_181485 |
| uc010tbw.3 | ZNF268 | zinc finger protein 268 (ZNF268), var5, (from RefSeq NM_001165883) | NM_001165883 |
| uc001ico.4 | ZNF496 | zinc finger protein 496 (ZNF496), (from RefSeq NM_032752) | NM_032752 |
| uc002mtq.3 | ZNF563 | zinc finger protein 563 (ZNF563), (from RefSeq NM_145276) | NM_145276 |
| uc060zmo.1 | ZNF576 | zinc finger protein 576 (ZNF576), var2, (from RefSeq NM_001145347) | NM_001145347 |
| uc061dni.1 | ZNF587 | zinc finger protein 587 (ZNF587), var2, (from RefSeq NM_001204817) | NM_001204817 |
| uc062iuz.1 | ZNF852 | zinc finger protein 852 (ZNF852), (from RefSeq NM_001287349) | NM_001287349 |
| uc002bkr.4 | ZSCAN2 | zinc finger and SCAN domain containing 2 (ZSCAN2), var1, (from RefSeq NM_181877) | NM_181877 |
| uc059mrx.1 | ZSCAN2 | zinc finger and SCAN domain containing 2 (ZSCAN2), var1, (from RefSeq NM_181877) | NM_181877 |
| uc059mry.1 | ZSCAN2 | zinc finger and SCAN domain containing 2 (ZSCAN2), var1, (from RefSeq NM_181877) | NM_181877 |
| uc059msa.1 | ZSCAN2 | zinc finger and SCAN domain containing 2 (ZSCAN2), var1, (from RefSeq NM_181877) | NM_181877 |

TABLE 7

| GeneName | Symbol | Description | RefSeq |
|---|---|---|---|
| uc003wjo.3 | ABCF2 | ATP-binding cassette, sub-family F (GCN20), member 2 (ABCF2), var 2, (NM_005692) | NM_005692 |
| uc059xhj.1 | ADAT1 | adenosine deaminase, tRNA-specific 1 (ADAT1), var 1, (NM_012091) | NM_012091 |
| uc001mdb.4 | APBB1 | amyloid beta (A4) precursor protein-binding, family B, member 1 (Fe65) (APBB1), var, (NM_001164) | NM_001164 |
| uc001mdc.3 | APBB1 | amyloid beta (A4) precursor protein-binding, family B, member 1 (Fe65) (APBB1), var 2, (NM_145689) | NM_145689 |
| uc057yjv.1 | APBB1 | amyloid beta (A4) precursor protein-binding, family B, member 1 (Fe65) (APBB1), var 1, (NM_001164) | NM_001164 |
| uc057yjz.1 | APBB1 | amyloid beta (A4) precursor protein-binding, family B, member 1 (Fe65) (APBB1), var 1, (NM_001164) | NM_001164 |
| uc065ahz.1 | ARMCX6 | armadillo repeat containing, X-linked 6 (ARMCX6), var 3, (NM_001184768) | NM_001184768 |
| uc059ulu.1 | BBS2 | Bardet-Biedl syndrome 2 (BBS2), (NM_031885) | NM_031885 |
| uc061wwa.1 | BLCAP | bladder cancer associated protein (BLCAP), var 2, (NM_001167820) | NM_001167820 |
| uc058bon.1 | C11orf31 | chromosome 11 open reading frame 31 (C11orf31), (NM_170746) | NM_170746 |
| uc059tos.1 | C16orf58 | chromosome 16 open reading frame 58 (C16orf58), (NM_022744) | NM_022744 |
| uc062hvi.1 | CNOT10 | CCR4-NOT transcription complex subunit 10 | NR_046352 |
| uc064rqz.1 | COMMD5 | COMM domain containing 5 (COMMD5), var 3, (NM_001081004) | NM_001081004 |
| uc001tyn.4 | COQ5 | coenzyme Q5 homolog, methyltransferase (S. cerevisiae) (COQ5), (NM_032314) | NM_032314 |
| uc001lwg.2 | CPOX | coproporphyrinogen oxidase (CPOX), (NM_000097) | NM_000097 |
| uc010rgn.2 | CRY2 | cryptochrome circadian clock 2 (CRY2), var 1, (NM_021117) | NM_021117 |
| uc058ato.1 | CRY2 | cryptochrome circadian clock 2 (CRY2), var 1, (NM_021117) | NM_021117 |
| uc057oir.1 | CSRP1 | a member of the cysteine-rich protein (CSRP) family | NM_001193570 |
| uc062ukk.1 | CTBP1 | C-terminal binding protein 1 (CTBP1), var 2, (NM_001012614) | NM_001012614 |
| uc057jkc.1 | CTTNBP2NL | CTTNBP2 N-terminal like (CTTNBP2NL), (NM_018704) | NM_018704 |

TABLE 7-continued

| GeneName | Symbol | Description | RefSeq |
|---|---|---|---|
| uc061otq.1 | CYTIP | cytohesin 1 interacting protein (CYTIP), (NM_004288) | NM_004288 |
| uc060zfv.1 | DEDD2 | death effector domain containing 2 | NR_073051 |
| uc021wlp.2 | DGCR8 | DGCR8 microprocessor complex subunit (DGCR8), var 2, (NM_001190326) | NM_001190326 |
| uc058pdy.1 | DGKA | diacylglycerol kinase, alpha 80 kDa (DGKA), var 4, (NM_201554) | NM_201554 |
| uc062jfe.1 | DHX30 | DEAH (Asp-Glu-Ala-His) box helicase 30 (DHX30), var 1, (NM_138615) | NM_138615 |
| uc010wnn.2 | DYNLL2 | dynein, light chain, LC8-type 2 (DYNLL2), (NM_080677) | NM_080677 |
| uc059soq.1 | EIF3CL | eukaryotic translation initiation factor 3, subunit C-like (EIF3CL), (NM_001099661) | NM_001099661 |
| uc002gnz.5 | ELAC2 | elaC ribonuclease Z 2 | NM_018127 |
| uc057gll.1 | EPS15 | epidermal growth factor receptor pathway substrate 15 (EPS15), var 1, (NM_001981) | NM_001981 |
| uc060vkb.1 | FAM129C | family with sequence similarity 129, member C (FAM129C), var 2, (NM_001098524) | NM_001098524 |
| uc058fep.1 | FCHSD2 | FCH and double SH3 domains 2 (FCHSD2), (NM_014824) | NM_014824 |
| uc064glm.1 | FIS1 | fission 1 (mitochondrial outer membrane) homolog (S. cerevisiae) (FIS1), (NM_016068) | NM_016068 |
| uc003djj.3 | FLNB | filamin B, beta (FLNB), var 2, (NM_001457) | NM_001457 |
| uc010hnf.3 | FLNB | filamin B, beta (FLNB), var 4, (NM_001164319) | NM_001164319 |
| uc064mnv.1 | FNTA | farnesyltransferase, CAAX box, alpha (FNTA), var 1, (NM_002027) | NM_002027 |
| uc060atq.1 | FXR2 | fragile X mental retardation, autosomal homolog 2 (FXR2), (NM_004860) | NM_004860 |
| uc002iii.2 | HEXIM2 | hexamethylene bis-acetamide inducible 2 | NM_001303442 |
| uc058uor.1 | HIP1R | huntingtin interacting protein 1 related (HIP1R), var 1, (NM_003959) | NM_003959 |
| uc063ljh.1 | IRF4 | interferon regulatory factor 4 | NM_001195286 |
| uc061nqc.1 | IWS1 | IWS1 homolog (S. cerevisiae) (IWS1), (NM_017969) | NM_017969 |
| uc063hbv.1 | JADE2 | jade family PHD finger 2 (JADE2), var 3, (NM_015288) | NM_015288 |
| uc063ady.1 | LRBA | LPS-responsive vesicle trafficking, beach and anchor containing (LRBA), var 2, (NM_006726) | NM_006726 |
| uc060ltc.1 | LRRC45 | leucine rich repeat containing 45 (LRRC45), (NM_144999) | NM_144999 |
| uc057jyz.1 | NBPF15 | neuroblastoma breakpoint family, member 15 (NBPF15), var 2, (NM_173638) | NM_173638 |
| uc057jza.1 | NBPF15 | neuroblastoma breakpoint family, member 15 (NBPF15), var 2, (NM_173638) | NM_173638 |
| uc061var.1 | NOP56 | NOP56 ribonucleoprotein (NOP56), var 1, (NM_006392) | NM_006392 |
| uc059six.1 | NSMCE1 | non-SMC element 1 homolog (S. cerevisiae) (NSMCE1), (NM_145080) | NM_145080 |
| uc061aza.1 | NTF4 | neurotrophin 4 (NTF4), (NM_006179) | NM_006179 |
| uc062xlo.1 | NUP54 | nucleoporin 54 kDa | NR_103781 |
| uc062xlr.1 | NUP54 | nucleoporin 54 kDa | NR_103782 |
| uc061bmx.1 | NUP62 | nucleoporin 62 kDa (NUP62), var 1, (NM_153719) | NM_153719 |
| uc057jvt.1 | PHGDH | phosphoglycerate dehydrogenase (PHGDH), (NM_006623) | NM_006623 |
| uc059rbn.1 | PLA2G10, | phospholipase A2, group X (PLA2G10), (NM_003561), | NM_003561 |
| uc062iet.1 | PLCD1 | phospholipase C, delta 1 (PLCD1), var 2, (NM_006225) | NM_006225 |
| uc061xai.1 | PLCG1 | phospholipase C, gamma 1 (PLCG1), var 2, (NM_182811) | NM_182811 |
| uc063msm.1 | PPP1R10 | protein phosphatase 1 regulatory subunit 10 | NR_072994 |
| uc063twf.1 | PPP1R10 | protein phosphatase 1 regulatory subunit 10 | NR_072994 |
| uc063vcd.1 | PPP1R10 | protein phosphatase 1 regulatory subunit 10 | NR_072994 |
| uc063whs.1 | PPP1R10 | protein phosphatase 1 regulatory subunit 10 | NR_072994 |
| uc063xhb.1 | PPP1R10 | protein phosphatase 1 regulatory subunit 10 | NR_072994 |
| uc063ymx.1 | PPP1R10 | protein phosphatase 1 regulatory subunit 10 | NR_072994 |
| uc063zss.1 | PPP1R10 | protein phosphatase 1 regulatory subunit 10 | NR_072994 |
| uc064wqo.1 | PRRC2B | proline-rich coiled-coil 2B (PRRC2B), (NM_013318) | NM_013318 |
| uc059xcn.1 | RFWD3 | ring finger and WD repeat domain 3 (RFWD3), (NM_018124) | NM_018124 |
| uc064qmg.1 | RP11-157E21.1 | uncharacterized LOC101927822 (LOC101927822), long non-coding RNA. (NR_125424) | NR_125424 |
| uc060hiq.1 | RSAD1 | radical S-adenosyl methionine domain containing 1 (RSAD1), var 1, (NM_018346) | NM_018346 |
| uc062oaq.1 | RYK | receptor-like tyrosine kinase (RYK), var 2, (NM_002958) | NM_002958 |
| uc062evq.1 | SERHL2 | serine hydrolase-like 2 | NR_104301 |
| uc062evt.1 | SERHL2 | serine hydrolase-like 2 | NR_104300 |
| uc063exq.1 | SERINC5 | serine incorporator 5 | NM_001174071 |
| uc062bvk.1 | SERPIND1 | serpin peptidase inhibitor, clade D (heparin cofactor), member 1 (SERPIND1), (NM_000185) | NM_000185 |
| uc062djs.1 | SFI1 | Sfi1 homolog, spindle assembly associated (yeast) (SFI1), var 2, (NM_014775) | NM_014775 |
| uc001zwr.5 | SLC12A1 | solute carrier family 12 (sodium/potassium/chloride transporter), member 1 (SLC12A1), var 1, (NM_000338) | NM_000338 |
| uc063fxo.1 | SLC25A46 | solute carrier family 25 member 46 | NM_001303250 |
| uc062iym.1 | SLC6A20 | solute carrier family 6 (proline IMINO transporter), member 20 (SLC6A20), var 2, (NM_022405) | NM_022405 |
| uc061ver.1 | SMOX | spermine oxidase (SMOX), var 2, (NM_175840) | NM_175840 |
| uc064hsz.1 | SND1 | staphylococcal nuclease and tudor domain containing 1 (SND1), (NM_014390) | NM_014390 |
| uc063eby.1 | SREK1 | splicing regulatory glutamine/lysine-rich protein 1 (SREK1), var 4, (NM_001270493) | NM_001270493 |
| uc010rnb.2 | STIP1 | stress-induced phosphoprotein 1 (STIP1), var 3, (NM_001282653) | NM_001282653 |
| uc057jcy.1 | STRIP1 | striatin interacting protein 1 (STRIP1), var 2, (NM_001270768) | NM_001270768 |
| uc059pdz.1 | TBL3 | transducin (beta)-like 3 (TBL3), (NM_006453) | NM_006453 |
| uc060rek.1 | TCF3 | transcription factor 3 (TCF3), var 1, (NM_003200) | NM_003200 |
| uc060upn.1 | TECR | trans-2,3-enoyl-CoA reductase (TECR), var 1, (NM_138501) | NM_138501 |
| uc061kij.1 | TIA1 | TIA1 cytotoxic granule-associated RNA binding protein (TIA1), var 2, (NM_022173) | NM_022173 |
| uc058ssh.1 | TMEM263 | transmembrane protein 263 (TMEM263), (NM_152261) | NM_152261 |
| uc061duf.1 | TRIM28 | tripartite motif containing 28 (TRIM28), (NM_005762) | NM_005762 |
| uc062atf.1 | UBE2G2 | ubiquitin-conjugating enzyme E2G 2 (UBE2G2), (NM_003343) | NM_003343 |
| uc058dep.1 | VPS51 | vacuolar protein sorting 51 homolog (S. cerevisiae) (VPS51), var 1, (NM_013265) | NM_013265 |
| uc060pua.1 | ZCCHC2 | zinc finger, CCHC domain containing 2 (ZCCHC2), var 1, (NM_017742) | NM_017742 |
| uc061you.1 | ZGPAT | zinc finger, CCCH-type with G patch domain (ZGPAT), var 3, (NM_181485) | NM_181485 |
| uc001ico.4 | ZNF496 | zinc finger protein 496 (ZNF496), (NM_032752) | NM_032752 |
| uc060zmo.1 | ZNF576 | zinc finger protein 576 (ZNF576), var 2, (NM_001145347) | NM_001145347 |
| uc061dni.1 | ZNF587 | zinc finger protein 587 (ZNF587), var 2, (NM_001204817) | NM_001204817 |

TABLE 7-continued

| GeneName | Symbol | Description | RefSeq |
| --- | --- | --- | --- |
| uc062iuz.1 | ZNF852 | zinc finger protein 852 (ZNF852), (NM_001287349) | NM_001287349 |
| uc059mry.1 | ZSCAN2 | zinc finger and SCAN domain containing 2 (ZSCAN2), var 1, (NM_181877) | NM_181877 |
| uc059msa.1 | ZSCAN2 | zinc finger and SCAN domain containing 2 (ZSCAN2), var 1, (NM_181877) | NM_181877 |

TABLE 8

| GeneName | Symbol | Description | RefSeq |
| --- | --- | --- | --- |
| uc059ulu.1 | BBS2 | Bardet-Biedl syndrome 2 (BBS2)(NM_031885) | NM_031885 |
| uc061otq.1 | CYTIP | cytohesin 1 interacting protein (CYTIP)(NM_004288) | NM_004288 |
| uc021wlp.2 | DGCR8 | DGCR8 microprocessor complex subunit (DGCR8), var 2(NM_001190326) | NM_001190326 |
| uc062seb.1 | DLG1 | discs, large homolog 1 (*Drosophila*) (DLG1), var 3(NM_001204386) | NM_001204386 |
| uc064glm.1 | FIS1 | fission 1 (mitochondrial outer membrane)(FIS1)(NM_016068) | NM_016068 |
| uc057dtw.1 | GPATCH3 | G patch domain containing 3 (GPATCH3)(NM_022078) | NM_022078 |
| uc063ixf.1 | GRIA1 | glutamate receptor, ionotropic, AMPA 1 (GRIA1), var 7(NM_001258023) | NM_001258023 |
| uc021txo.2 | NT5C3B | 5'-nucleotidase, cytosolic IIIB (NT5C3B), var 1(NM_052935) | NM_052935 |
| uc062iet.1 | PLCD1 | phospholipase C, delta 1 (PLCD1), var 2(NM_006225) | NM_006225 |
| uc063mxz.1 | PSORS1C1 | psoriasis susceptibility 1 candidate 1 (PSORS1C1)(NM_014068), | NM_014068 |
| uc058mvt.1 | PUS7L | pseudouridylate synthase 7 homolog like (PUS7L), var 2(NM_001098614) | NM_001098614 |
| uc061irb.1 | THADA | thyroid adenoma associated | NR_073394 |
| uc058ssh.1 | TMEM263 | transmembrane protein 263 (TMEM263)(NM_152261) | NM_152261 |
| uc061dni.1 | ZNF587 | zinc finger protein 587 (ZNF587), var 2(NM_001204817) | NM_001204817 |

TABLE 9

| GeneName | Symbol | Description | RefSeq |
| --- | --- | --- | --- |
| uc004ers.4 | SEPT6 | septin 6 (SEPT6) var III, (NM_145800) | NM_145800 |
| uc060kqb.1 | SEPT9 | septin 9 (SEPT9) var 9, (NM_001293696) | NM_001293696 |
| uc060kqt.1 | SEPT9 | septin 9 (SEPT9) var 9, (NM_001293696) | NM_001293696 |
| uc061drv.1 | A1BG | alpha-1-B glycoprotein (A1BG), (NM_130786) | NM_130786 |
| uc058oph.1 | AAAS | achalasia, adrenocortical insufficiency, alacrimia (AAAS) var 1, (NM_015665) | NM_015665 |
| uc063ayd.1 | AADAT | aminoadipate aminotransferase (AADAT) var 2 , (NM_182662) | NM_182662 |
| uc057ilc.1 | ABCA4 | ATP-binding cassette, sub-family A (ABC1), member 4 (ABCA4), (NM_000350) | NM_000350 |
| uc011eyl.3 | ABCF1 | ATP-binding cassette, sub-family F (GCN20), member 1 (ABCF1) var 1, (NM_001025091), | NM_001025091 |
| uc011fwy.3 | ABCF1 | ATP-binding cassette, sub-family F (GCN20), member 1 (ABCF1) var 1, (NM_001025091), | NM_001025091 |
| uc011gtb.3 | ABCF1 | ATP-binding cassette, sub-family F (GCN20), member 1 (ABCF1) var 1, (NM_001025091), | NM_001025091 |
| uc011hlv.3 | ABCF1 | ATP-binding cassette, sub-family F (GCN20), member 1 (ABCF1) var 1 , (NM_001025091), | NM_001025091 |
| uc011ija.3 | ABCF1 | ATP-binding cassette, sub-family F (GCN20), member 1 (ABCF1) var 1, (NM_001025091), | NM_001025091 |
| uc011jge.3 | ABCF1 | ATP-binding cassette, sub-family F (GCN20), member 1 (ABCF1) var 1, (NM_001025091), | NM_001025091 |
| uc003wjo.3 | ABCF2 | ATP-binding cassette, sub-family F (GCN20), member 2 (ABCF2) var 2, (NM_005692) | NM_005692 |
| uc064jjf.1 | ABCF2 | ATP-binding cassette, sub-family F (GCN20), member 2 (ABCF2) var 2, (NM_005692) | NM_005692 |
| uc057wcy.1 | ABLIM1 | actin binding LIM protein 1 (ABLIM1) var 1, (NM_002313) | NM_002313 |
| uc064bvu.1 | AC099342.1 | uncharacterized LOC101927769 (LOC101927769), long non-coding RNA. (NR_110117) | NR_110117 |
| uc057bbq.1 | ACAP3 | ArfGAP with coiled-coil, ankyrin repeat and PH domains 3 (ACAP3), (NM_030649) | NM_030649 |
| uc060gfn.1 | ACBD4 | acyl-CoA binding domain containing 4 (ACBD4) var 5, (NM_001135707) | NM_001135707 |
| uc064mff.1 | ADAM32 | ADAM metallopeptidase domain 32 (ADAM32), (NM_145004), | NM_145004 |
| uc059xiz.1 | ADAMTS18 | ADAM metallopeptidase with thrombospondin type 1 motif, 18 (ADAMTS18), (NM_199355) | NM_199355 |
| uc002zgr.3 | ADARB1 | adenosine deaminase, RNA-specific, B1 (ADARB1) var 3, (NM_015834) | NM_015834 |
| uc059xhj.1 | ADAT1 | adenosine deaminase, tRNA-specific 1 (ADAT1) var 1, (NM_012091) | NM_012091 |
| uc060yvy.1 | ADCK4 | aarF domain containing kinase 4 (ADCK4) var 1, (NM_024876) | NM_024876 |
| uc062ylf.1 | ADH1C | alcohol dehydrogenase 1C (class I), gamma polypeptide (ADH1C), (NM_000669) | NM_000669 |
| uc021xqj.2 | ADH7 | alcohol dehydrogenase 7 (class IV), mu or sigma polypeptide (ADH7) var 1, (NM_001166504) | NM_001166504 |
| uc060qmg.1 | ADNP2 | ADNP homeobox 2 (ADNP2), (NM_014913) | NM_014913 |
| uc002bmt.3 | AEN | apoptosis enhancing nuclease (AEN), (NM_022767) | NM_022767 |
| uc062apr.1 | AGPAT3 | 1-acylglycerol-3-phosphate O-acyltransferase 3 (AGPAT3) var 2, (NM_001037553) | NM_001037553 |
| uc062apx.1 | AGPAT3 | 1-acylglycerol-3-phosphate O-acyltransferase 3 (AGPAT3) var 2, (NM_001037553) | NM_001037553 |
| uc011kox.1 | AHCYL2 | adenosylhomocysteinase-like 2 (AHCYL2) var 3, (NM_001130722) | NM_001130722 |
| uc063bvy.1 | AHRR | aryl-hydrocarbon receptor repressor (AHRR) var 2, (NM_001242412) | NM_001242412 |
| uc063bvz.1 | AHRR | aryl-hydrocarbon receptor repressor (AHRR) var 2, (NM_001242412) | NM_001242412 |
| uc058kxa.1 | AICDA | activation-induced cytidine deaminase (AICDA), (NM_020661) | NM_020661 |
| uc058kxb.1 | AICDA | activation-induced cytidine deaminase (AICDA), (NM_020661) | NM_020661 |
| uc064uzz.1 | AKAP2 | A kinase (PRKA) anchor protein 2 (AKAP2) var 2, (NM_001136562) | NM_001136562 |
| uc064ieo.1 | AKR1B1 | aldo-keto reductase family 1, member B1 (aldose reductase) (AKR1B1), (NM_001628) | NM_001628 |
| uc064vdz.1 | ALAD | aminolevulinate dehydratase (ALAD), (NM_000031) | NM_000031 |
| uc031sbq.2 | ALDH1L1-AS1 | ALDH1L1 antisense RNA 1 (ALDH1L1-AS1), long non-coding RNA. (NR_046602) | NR_046602 |
| uc001dzb.4 | ALX3 | ALX homeobox 3 (ALX3), (NM_006492) | NM_006492 |
| uc058ugz.1 | ANAPC5 | anaphase promoting complex subunit 5 (ANAPC5) var 1, (NM_016237) | NM_016237 |
| uc064fhw.1 | ANKIB1 | ankyrin repeat and IBR domain containing 1 (ANKIB1), (NM_019004) | NM_019004 |
| uc001ukx.3 | ANKLE2 | ankyrin repeat and LEM domain containing 2 (ANKLE2), (NM_015114) | NM_015114 |
| uc060dka.1 | ANKRD13B | ankyrin repeat domain 13B (ANKRD13B), (NM_152345) | NM_152345 |

TABLE 9-continued

| GeneName | Symbol | Description | RefSeq |
|---|---|---|---|
| uc061lxq.1 | ANKRD23 | ankyrin repeat domain 23 (ANKRD23), (NM_144994) | NM_144994 |
| uc062ear.1 | ANKRD54 | ankyrin repeat domain 54 (ANKRD54) var 1, (NM_138797) | NM_138797 |
| uc062eaw.1 | ANKRD54 | ankyrin repeat domain 54 (ANKRD54) var 1, (NM_138797) | NM_138797 |
| uc059qhs.1 | ANKS3 | ankyrin repeat and sterile alpha motif domain containing 3 (ANKS3) var 1, (NM_133450) | NM_133450 |
| uc062itu.1 | ANO10 | anoctamin 10 (ANO10) var 5, (NM_001204834) | NM_001204834 |
| uc060rik.1 | AP3D1 | adaptor-related protein complex 3, delta 1 subunit (AP3D1) var 2, (NM_003938) | NM_003938 |
| uc064mjf.1 | AP3M2 | adaptor-related protein complex 3, mu 2 subunit (AP3M2) var 2, (NM_006803) | NM_006803 |
| uc001mdb.4 | APBB1 | amyloid beta (A4) precursor protein-binding, family B, member 1 (Fe65) (APBB1) var 1, (NM_001164) | NM_001164 |
| uc001mdc.3 | APBB1 | amyloid beta (A4) precursor protein-binding, family B, member 1 (Fe65) (APBB1) var 2, (NM_145689) | NM_145689 |
| uc001mdd.6 | APBB1 | amyloid beta (A4) precursor protein-binding, family B, member 1 (Fe65) (APBB1) var 8, (NM_001257323) | NM_001257323 |
| uc057yjt.1 | APBB1 | amyloid beta (A4) precursor protein-binding, family B, member 1 (Fe65) (APBB1) var 4, (NM_001257321) | NM_001257321 |
| uc057yjv.1 | APBB1 | amyloid beta (A4) precursor protein-binding, family B, member 1 (Fe65) (APBB1) var 1, (NM_001164) | NM_001164 |
| uc057yjz.1 | APBB1 | amyloid beta (A4) precursor protein-binding, family B, member 1 (Fe65) (APBB1) var 1, (NM_001164) | NM_001164 |
| uc057yka.1 | APBB1 | amyloid beta (A4) precursor protein-binding, family B, member 1 (Fe65) (APBB1) var 11, non-coding RNA. | NR_047512 |
| uc057ykb.1 | APBB1 | amyloid beta (A4) precursor protein-binding, family B, member 1 (Fe65) (APBB1) var 4, (NM_001257321) | NM_001257321 |
| uc057ykd.1 | APBB1 | amyloid beta (A4) precursor protein-binding, family B, member 1 (Fe65) (APBB1) var 6, (NM_001257320) | NM_001257320 |
| uc057yke.1 | APBB1 | amyloid beta (A4) precursor protein-binding, family B, member 1 (Fe65) (APBB1) var 5, (NM_001257326) | NM_001257326 |
| uc058ytf.1 | APEX1 | APEX nuclease (multifunctional DNA repair enzyme) 1 (APEX1) var 1, (NM_001641) | NM_001641 |
| uc062dsw.1 | APOL4 | apolipoprotein L, 4 (APOL4) var a, (NM_030643) | NM_030643 |
| uc061yli.1 | ARFGAP1 | ADP-ribosylation factor GTPase activating protein 1 (ARFGAP1) var 1, (NM_018209) | NM_018209 |
| uc059sgo.1 | ARHGAP17 | Rho GTPase activating protein 17 (ARHGAP17) var 2, (NM_018054) | NM_018054 |
| uc065aip.1 | ARMCX2 | armadillo repeat containing, X-linked 2 (ARMCX2) var 2, (NM_014782) | NM_014782 |
| uc065ahz.1 | ARMCX6 | armadillo repeat containing, X-linked 6 (ARMCX6) var 3, (NM_001184768) | NM_001184768 |
| uc059mjv.1 | ARNT2 | aryl-hydrocarbon receptor nuclear translocator 2 (ARNT2), (NM_014862) | NM_014862 |
| uc003cgd.4 | ARPP21 | cAMP-regulated phosphoprotein, 21 kDa (ARPP21) var 7, (NM_001267618) | NM_001267618 |
| uc062hzx.1 | ARPP21 | cAMP-regulated phosphoprotein, 21 kDa (ARPP21) var 4, (NM_001025069) | NM_001025069 |
| uc061syr.1 | ASIC4 | acid sensing (proton gated) ion channel family member 4 (ASIC4), (NM_182847) | NM_182847 |
| uc003uou.5 | ASNS | asparagine synthetase (glutamine-hydrolyzing) (ASNS) var 3, (NM_183356) | NM_183356 |
| uc059zrw.1 | ATP2A3 | ATPase, Ca++ transporting, ubiquitous (ATP2A3) var 7, (NM_174958) | NM_174958 |
| uc060gym.1 | ATP5G1 | ATP synthase, H+ transporting, mitochondrial Fo complex, subunit C1 (subunit 9) (ATP5G1) var 2, (NM_001002027) | NM_001002027 |
| uc063nbq.1 | ATP6V1G2 | ATPase, H+ transporting, lysosomal 13 kDa, V1 subunit G2 (ATP6V1G2) var 2, (NM_138282) | NM_138282 |
| uc063zxi.1 | ATP6V1G2 | ATPase, H+ transporting, lysosomal 13 kDa, V1 subunit G2 (ATP6V1G2) var 2, (NM_138282) | NM_138282 |
| uc002jfh.4 | AXIN2 | axin 2 (AXIN2), (NM_004655) | NM_004655 |
| uc058qar.1 | B4GALNT1 | beta-1,4-N-acetyl-galactosaminyl transferase 1 (B4GALNT1) var 2, (NM_001276468) | NM_001276468 |
| uc001ynh.3 | BAG5 | BCL2-associated athanogene 5 (BAG5) var 1, (NM_001015049) | NM_001015049 |
| uc059ulu.1 | BBS2 | Bardet-Biedl syndrome 2 (BBS2), (NM_031885) | NM_031885 |
| uc002zwy.4 | BCR | breakpoint cluster region (BCR) var 2, (NM_021574) | NM_021574 |
| uc063ewe.1 | BHMT | betaine--homocysteine S-methyltransferase (BHMT), (NM_001713) | NM_001713 |
| uc061wwa.1 | BLCAP | bladder cancer associated protein (BLCAP) var 2, (NM_001167820) | NM_001167820 |
| uc061wwb.1 | BLCAP | bladder cancer associated protein (BLCAP) var 2, (NM_001167820) | NM_001167820 |
| uc064kgd.1 | BLK | BLK proto-oncogene, Src family tyrosine kinase (BLK), (NM_001715) | NM_001715 |
| uc003mxu.5 | BMP6 | bone morphogenetic protein 6 (BMP6), (NM_001718) | NM_001718 |
| uc063hjj.1 | BRD8 | bromodomain containing 8 (BRD8) var 6, (NM_001300962) | NM_001300962 |
| uc063hjk.1 | BRD8 | bromodomain containing 8 (BRD8) var 6, (NM_001300962) | NM_001300962 |
| uc010jwv.4 | BTBD9 | BTB (POZ) domain containing 9 (BTBD9) var 4, (NM_001172418) | NM_001172418 |
| uc003dzb.5 | BTLA | B and T lymphocyte associated (BTLA) var 2, (NM_001085357) | NM_001085357 |
| uc001kui.4 | C10orf76 | chromosome 10 open reading frame 76 (C10orf76), (NM_024541) | NM_024541 |
| uc058bon.1 | C11orf31 | chromosome 11 open reading frame 31 (C11orf31), (NM_170746) | NM_170746 |
| uc058usc.1 | C12orf65 | chromosome 12 open reading frame 65 (C12orf65) var 1, (NM_152269) | NM_152269 |
| uc059ein.1 | C14orf159 | chromosome 14 open reading frame 159 (C14orf159) var 3, (NM_024952) | NM_024952 |
| uc059gcd.1 | C14orf80 | chromosome 14 open reading frame 80 (C14orf80) var 1, (NM_001134875) | NM_001134875 |
| uc059gce.1 | C14orf80 | chromosome 14 open reading frame 80 (C14orf80) var 1, (NM_001134875) | NM_001134875 |
| uc059tos.1 | C16orf58 | chromosome 16 open reading frame 58 (C16orf58), (NM_022744) | NM_022744 |
| uc021tna.1 | C17orf97 | chromosome 17 open reading frame 97 (C17orf97), (NM_001013672) | NM_001013672 |
| uc057jso.1 | C1orf137 | chromosome 1 open reading frame 137 (C1orf137), (NM_001013643) | NM_001013643 |
| uc057cmh.1 | C1orf195 | chromosome 1 open reading frame 195 (C1orf195) var 2, (NM_001278502) | NM_001278502 |
| uc062aqp.1 | C21orf33 | chromosome 21 open reading frame 33 (C21orf33) var 1, (NM_004649) | NM_004649 |
| uc010ypl.2 | C2orf74 | chromosome 2 open reading frame 74 (C2orf74) var 2, (NM_001143960) | NM_001143960 |
| uc063nqr.1 | C6orf10, | chromosome 6 open reading frame 10 (C6orf10) var 2, (NM_001286474), | NM_001286474 |
| uc063wxg.1 | C6orf10, | chromosome 6 open reading frame 10 (C6orf10) var 2, (NM_001286474), | NM_001286474 |
| uc063zgk.1 | C6orf10, | chromosome 6 open reading frame 10 (C6orf10) var 2, (NM_001286474), | NM_001286474 |
| uc064sfx.1 | C9orf92 | chromosome 9 open reading frame 92 (C9orf92) var 1, (NM_001271829) | NM_001271829 |
| uc057nmb.1 | CACYBP | calcyclin binding protein (CACYBP) var 1, (NM_014412) | NM_014412 |
| uc002rji.4 | CAD | carbamoyl-phosphate synthetase 2, aspartate transcarbamylase, and dihydroorotase (CAD) var 1, (NM_004341) | NM_004341 |
| uc063fyf.1 | CAMK4 | calcium/calmodulin-dependent protein kinase IV (CAMK4), (NM_001744) | NM_001744 |
| uc063fyh.1 | CAMK4 | calcium/calmodulin-dependent protein kinase IV (CAMK4), (NM_001744) | NM_001744 |

TABLE 9-continued

| GeneName | Symbol | Description | RefSeq |
|---|---|---|---|
| uc062jyn.1 | CAMKV | CaM kinase-like vesicle-associated (CAMKV), (NM_024046) | NM_024046 |
| uc010nbg.4 | CAMSAP1 | calmodulin regulated spectrin-associated protein 1 (CAMSAP1), (NM_015447) | NM_015447 |
| uc064rtg.1 | CBWD1 | COBW domain containing 1 (CBWD1) var 1, (NM_018491) | NM_018491 |
| uc031rza.1 | CCDC13-AS1 | CCDC13 antisense RNA 1 (CCDC13-AS1), long non-coding RNA. (NR_046732) | NR_046732 |
| uc021wxn.3 | CCDC51 | coiled-coil domain containing 51 (CCDC51) var 3, (NM_001256965) | NM_001256965 |
| uc062kus.1 | CCDC66 | coiled-coil domain containing 66 (CCDC66) var 1, (NM_001141947) | NM_001141947 |
| uc010aty.4 | CCDC88C | coiled-coil domain containing 88C (CCDC88C), (NM_001080414) | NM_001080414 |
| uc058mhe.1 | CCDC91 | coiled-coil domain containing 91 (CCDC91), (NM_018318) | NM_018318 |
| uc003nsq.5 | CCHCR1 | coiled-coil alpha-helical rod protein 1 (CCHCR1) var 2, (NM_001105563) | NM_001105563 |
| uc010jsk.2 | CCHCR1, | coiled-coil alpha-helical rod protein 1 (CCHCR1) var 3, (NM_019052), | NM_019052 |
| uc063myg.1 | CCHCR1, | coiled-coil alpha-helical rod protein 1 (CCHCR1) var 3, (NM_019052), | NM_019052 |
| uc058jyi.1 | CCND2 | cyclin D2 (CCND2), (NM_001759) | NM_001759 |
| uc058dzl.1 | CCS | copper chaperone for superoxide dismutase (CCS), (NM_005125) | NM_005125 |
| uc061kps.1 | CCT7 | chaperonin containing TCP1, subunit 7 (eta) (CCT7) var 4, (NM_001166285) | NM_001166285 |
| uc059sqx.1 | CD19 | CD19 molecule (CD19) var 2, (NM_001770) | NM_001770 |
| uc060xbh.1 | CD22 | CD22 molecule (CD22) var 4, (NM_001185101) | NM_001185101 |
| uc060xbu.1 | CD22 | CD22 molecule (CD22) var 2, (NM_001185099) | NM_001185099 |
| uc060xci.1 | CD22 | CD22 molecule (CD22) var 5, (NM_001278417) | NM_001278417 |
| uc059lej.1 | CD276 | CD276 molecule (CD276) var 1, (NM_001024736) | NM_001024736 |
| uc010fgt.4 | CD8B | CD8b molecule (CD8B) var 6, (NM_001178100) | NM_001178100 |
| uc064bww.1 | CDCA7L | cell division cycle associated 7-like (CDCA7L) var 3, (NM_001127371) | NM_001127371 |
| uc064bwy.1 | CDCA7L | cell division cycle associated 7-like (CDCA7L) var 2, (NM_001127370) | NM_001127370 |
| uc059xrj.1 | CDH13 | cadherin 13 (CDH13) var 5, (NM_001220491) | NM_001220491 |
| uc059svu.1 | CDIPT | CDP-diacylglycerol--inositol 3-phosphatidyltransferase (CDIPT) var 2, (NM_001286585) | NM_001286585 |
| uc009xbk.3 | CDK18 | cyclin-dependent kinase 18 (CDK18) var 1, (NM_212503) | NM_212503 |
| uc058pfd.1 | CDK2 | cyclin-dependent kinase 2 (CDK2) var 1, (NM_001798) | NM_001798 |
| uc061wgl.1 | CDK5RAP1 | CDK5 regulatory subunit associated protein 1 (CDK5RAP1) var 5, (NM_001278169) | NM_001278169 |
| uc064vir.1 | CDK5RAP2 | CDK5 regulatory subunit associated protein 2 (CDK5RAP2) var 3, (NM_001272039) | NM_001272039 |
| uc063kyx.1 | CDK7, | cyclin-dependent kinase 7 (CDK7), (NM_001799), | NM_001799 |
| uc064skj.1 | CDKN2A | cyclin-dependent kinase inhibitor 2A (CDKN2A) var 4, (NM_058195) | NM_058195 |
| uc062fev.1 | CDPF1 | cysteine-rich, DPF motif domain containing 1 (CDPF1), (NM_207327) | NM_207327 |
| uc057jgz.1 | CEPT1 | choline/ethanolamine phosphotransferase 1 (CEPT1) var 2, (NM_001007794) | NM_001007794 |
| uc058nww.1 | CERS5 | ceramide synthase 5 (CERS5) var 1, (NM_147190) | NM_147190 |
| uc060awd.1 | CHD3 | chromodomain helicase DNA binding protein 3 (CHD3) var 2, (NM_005852) | NM_005852 |
| uc057jhu.1 | CHI3L2 | chitinase 3-like 2 (CHI3L2) var 3, (NM_001025199) | NM_001025199 |
| uc057xqb.1 | CHID1 | chitinase domain containing 1 (CHID1) var 5, (NM_001142677) | NM_001142677 |
| uc062gao.1 | CHL1 | cell adhesion molecule L1-like (CHL1) var 2, (NM_001253387) | NM_001253387 |
| uc064ldx.1 | CHMP7 | charged multivesicular body protein 7 (CHMP7), (NM_152272) | NM_152272 |
| uc064cks.1 | CHN2 | chimerin 2 (CHN2) var 2, (NM_004067) | NM_004067 |
| uc059hfw.1 | CHRM5 | cholinergic receptor, muscarinic 5 (CHRM5), (NM_012125) | NM_012125 |
| uc061mig.1 | CHST10 | carbohydrate sulfotransferase 10 (CHST10), (NM_004854) | NM_004854 |
| uc010rpp.3 | CLCF1 | cardiotrophin-like cytokine factor 1 (CLCF1) var 2, (NM_001166212) | NM_001166212 |
| uc0591jj.1 | CLK3 | CDC-like kinase 3 (CLK3) var 1, (NM_001130028) | NM_001130028 |
| uc0591jk.1 | CLK3 | CDC-like kinase 3 (CLK3) var 2, (NM_003992) | NM_003992 |
| uc063bzj.1 | CLPTM1L, | CLPTM1-like (CLPTM1L), (NM_030782), | NM_030782 |
| uc001aqi.4 | CLSTN1 | calsyntenin 1 (CLSTN1) var 2, (NM_014944) | NM_014944 |
| uc060mtc.1 | CLUL1 | clusterin-like 1 (retinal) (CLUL1) var 2, (NM_199167) | NM_199167 |
| uc062wki.1 | CNGA1 | cyclic nucleotide gated channel alpha 1 (CNGA1), (NM_000087) | NM_000087 |
| uc060tuj.1 | CNN1 | calponin 1, basic, smooth muscle (CNN1) var 1, (NM_001299) | NM_001299 |
| uc062hvt.1 | CNOT10 | CCR4-NOT transcription complex, subunit 10 (CNOT10) var 2, (NM_001256741) | NM_001256741 |
| uc064kms.1 | CNOT7 | CCR4-NOT transcription complex, subunit 7 (CNOT7) var 2, (NM_054026) | NM_054026 |
| uc063jat.1 | CNOT8 | CCR4-NOT transcription complex, subunit 8 (CNOT8) var 3, (NM_001301074) | NM_001301074 |
| uc057egb.1 | COL16A1 | collagen, type XVI, alpha 1 (COL16A1), (NM_001856) | NM_001856 |
| uc064rqz.1 | COMMD5 | COMM domain containing 5 (COMMD5) var 3, (NM_001081004) | NM_001081004 |
| uc057ugl.1 | COMTD1 | catechol-O-methyltransferase domain containing 1 (COMTD1), (NM_144589) | NM_144589 |
| uc057ugm.1 | COMTD1 | catechol-O-methyltransferase domain containing 1 (COMTD1), (NM_144589) | NM_144589 |
| uc057ugn.1 | COMTD1 | catechol-O-methyltransferase domain containing 1 (COMTD1), (NM_144589) | NM_144589 |
| uc001tyn.4 | COQ5 | coenzyme Q5 homolog, methyltransferase (*S. cerevisiae*) (COQ5), (NM_032314) | NM_032314 |
| uc064hyz.1 | CPA4 | carboxypeptidase A4 (CPA4) var 1, (NM_016352) | NM_016352 |
| uc064ofx.1 | CPNE3 | copine III (CPNE3), (NM_003909) | NM_003909 |
| uc062lwg.1 | CPOX | coproporphyrinogen oxidase (CPOX), (NM_000097) | NM_000097 |
| uc057odj.1 | CRB1 | crumbs family member 1, photoreceptor morphogenesis associated (CRB1) var 2, (NM_001193640) | NM_001193640 |
| uc064ijs.1 | CREB3L2 | cAMP responsive element binding protein 3-like 2 (CREB3L2) var 2, (NM_001253775) | NM_001253775 |
| uc057ssj.1 | CREM | cAMP responsive element modulator (CREM) var 19, (NM_183013) | NM_183013 |
| uc057ssk.1 | CREM | cAMP responsive element modulator (CREM) var 2, (NM_001881) | NM_001881 |
| uc009voy.2 | CROCC | ciliary rootlet coiled-coil, rootletin (CROCC), (NM_014675) | NM_014675 |
| uc009ykw.4 | CRY2 | cryptochrome circadian clock 2 (CRY2) var 2, (NM_001127457) | NM_001127457 |
| uc010rgn.2 | CRY2 | cryptochrome circadian clock 2 (CRY2) var 1, (NM_021117) | NM_021117 |
| uc058ato.1 | CRY2 | cryptochrome circadian clock 2 (CRY2) var 1, (NM_021117) | NM_021117 |
| uc058pli.1 | CS | citrate synthase (CS), (NM_004077) | NM_004077 |
| uc063glv.1 | CSNK1G3 | casein kinase 1, gamma 3 (CSNK1G3) var 2, (NM_001031812) | NM_001031812 |
| uc057oit.1 | CSRP1 | cysteine and glycine-rich protein 1 (CSRP1) var 1, (NM_004078) | NM_004078 |
| uc061vvp.1 | CSTL1 | cystatin-like 1 (CSTL1), (NM_138283) | NM_138283 |
| uc062ukk.1 | CTBP1 | C-terminal binding protein 1 (CTBP1) var 2, (NM_001012614) | NM_001012614 |
| uc059zqi.1 | CTNS | cystinosin, lysosomal cystine transporter (CTNS) var 2, (NM_004937) | NM_004937 |
| uc059was.1 | CTRL | chymotrypsin-like (CTRL), (NM_001907) | NM_001907 |
| uc057jkc.1 | CTTNBP2NL | CTTNBP2 N-terminal like (CTTNBP2NL), (NM_018704) | NM_018704 |

TABLE 9-continued

| GeneName | Symbol | Description | RefSeq |
|---|---|---|---|
| uc002leq.5 | CXXC1 | CXXC finger protein 1 (CXXC1) var 2, (NM_014593) | NM_014593 |
| uc063hsv.1 | CXXC5 | CXXC finger protein 5 (CXXC5), (NM_016463) | NM_016463 |
| uc063hsz.1 | CXXC5 | CXXC finger protein 5 (CXXC5), (NM_016463) | NM_016463 |
| uc063htb.1 | CXXC5 | CXXC finger protein 5 (CXXC5), (NM_016463) | NM_016463 |
| uc058cay.1 | CYB561A3 | cytochrome b561 family, member A3 (CYB561A3) var 4, (NM_001300763) | NM_001300763 |
| uc058cbb.1 | CYB561A3 | cytochrome b561 family, member A3 (CYB561A3) var 4, (NM_001300763) | NM_001300763 |
| uc059zsi.1 | CYB5D2 | cytochrome b5 domain containing 2 (CYB5D2) var 2, (NM_001254755) | NM_001254755 |
| uc060uuj.1 | CYP4F8 | cytochrome P450, family 4, subfamily F, polypeptide 8 (CYP4F8), (NM_007253) | NM_007253 |
| uc061otq.1 | CYTIP | cytohesin 1 interacting protein (CYTIP), (NM_004288) | NM_004288 |
| uc060rtj.1 | DAPK3 | death-associated protein kinase 3 (DAPK3), (NM_001348) | NM_001348 |
| uc002tux.2 | DARS | aspartyl-tRNA synthetase (DARS) var 1, (NM_001349) | NM_001349 |
| uc065cvb.1 | DAZ4 | deleted in azoospermia 4 (DAZ4) var 1, (NM_001005375) | NM_001005375 |
| uc061ppi.1 | DCAF17 | DDB1 and CUL4 associated factor 17 (DCAF17) var 2, (NM_001164821) | NM_001164821 |
| uc062wnz.1 | DCUN1D4 | DCN1, defective in cullin neddylation 1, domain containing 4 (DCUN1D4) var 3, (NM_001287755) | NM_001287755 |
| uc058bbm.1 | DDB2 | damage-specific DNA binding protein 2, 48 kDa (DDB2), (NM_000107) | NM_000107 |
| uc058mlq.1 | DDX11 | DEAD/H (Asp-Glu-Ala-Asp/His) box helicase 11 (DDX11) var 5, (NM_001257145) | NM_001257145 |
| uc058mls.1 | DDX11 | DEAD/H (Asp-Glu-Ala-Asp/His) box helicase 11 (DDX11) var 5, (NM_001257145) | NM_001257145 |
| uc057jjs.1 | DDX20 | DEAD (Asp-Glu-Ala-Asp) box polypeptide 20 (DDX20), (NM_007204) | NM_007204 |
| uc004cbs.3 | DDX31 | DEAD (Asp-Glu-Ala-Asp) box polypeptide 31 (DDX31) var 2, (NM_138620) | NM_138620 |
| uc063drm.1 | DDX4 | DEAD (Asp-Glu-Ala-Asp) box polypeptide 4 (DDX4) var 3, (NM_001166533) | NM_001166533 |
| uc060iqf.1 | DDX42 | DEAD (Asp-Glu-Ala-Asp) box helicase 42 (DDX42) var 2, (NM_203499) | NM_203499 |
| uc058utt.1 | DDX55 | DEAD (Asp-Glu-Ala-Asp) box polypeptide 55 (DDX55), (NM_020936) | NM_020936 |
| uc011lif.3 | DERL1 | derlin 1 (DERL1) var 1, (NM_024295) | NM_024295 |
| uc021wlp.2 | DGCR8 | DGCR8 microprocessor complex subunit (DGCR8) var 2, (NM_001190326) | NM_001190326 |
| uc058pdb.1 | DGKA | diacylglycerol kinase, alpha 80 kDa (DGKA) var 4, (NM_201554) | NM_201554 |
| uc058pdq.1 | DGKA | diacylglycerol kinase, alpha 80 kDa (DGKA) var 4, (NM_201554) | NM_201554 |
| uc058pdr.1 | DGKA | diacylglycerol kinase, alpha 80 kDa (DGKA) var 4, (NM_201554) | NM_201554 |
| uc058pdy.1 | DGKA | diacylglycerol kinase, alpha 80 kDa (DGKA) var 4, (NM_201554) | NM_201554 |
| uc064brc.1 | DGKB | diacylglycerol kinase, beta 90 kDa (DGKB) var 2, (NM_145695) | NM_145695 |
| uc062ray.1 | DGKG | diacylglycerol kinase, gamma 90 kDa (DGKG) var 3, (NM_001080745) | NM_001080745 |
| uc058avv.1 | DGKZ | diacylglycerol kinase, zeta (DGKZ) var 7, (NM_001199268) | NM_001199268 |
| uc060uba.1 | DHPS | deoxyhypusine synthase (DHPS) var 1, (NM_001930) | NM_001930 |
| uc062jfb.1 | DHX30 | DEAH (Asp-Glu-Ala-His) box helicase 30 (DHX30) var 1, (NM_138615) | NM_138615 |
| uc062jfe.1 | DHX30 | DEAH (Asp-Glu-Ala-His) box helicase 30 (DHX30) var 1, (NM_138615) | NM_138615 |
| uc058xkw.1 | DIS3 | DIS3 exosome endoribonuclease and 3'-5' exoribonuclease (DIS3) var 1, (NM_014953) | NM_014953 |
| uc059kmk.1 | DIS3L | DIS3 like exosome 3'-5' exoribonuclease (DIS3L) var 2, (NM_133375) | NM_133375 |
| uc062seb.1 | DLG1 | discs, large homolog 1 (*Drosophila*) (DLG1) var 3, (NM_001204386) | NM_001204386 |
| uc064yma.1 | DMD | dystrophin (DMD) var Dp116, (NM_004014) | NM_004014 |
| uc060xdo.1 | DMKN | dermokine (DMKN) var 1, (NM_001035516) | NM_001035516 |
| uc061cxq.1 | DNAAF3 | dynein, axonemal, assembly factor 3 (DNAAF3) var 2, (NM_178837) | NM_178837 |
| uc061cxr.1 | DNAAF3 | dynein, axonemal, assembly factor 3 (DNAAF3) var 1, (NM_001256714) | NM_001256714 |
| uc061cxt.1 | DNAAF3 | dynein, axonemal, assembly factor 3 (DNAAF3) var 4, (NM_001256716) | NM_001256716 |
| uc060ffp.1 | DNAJC7 | DnaJ (Hsp40) homolog, subfamily C, member 7 (DNAJC7) var 2, (NM_001144766) | NM_001144766 |
| uc062eiv.1 | DNAL4 | dynein, axonemal, light chain 4 (DNAL4), (NM_005740) | NM_005740 |
| uc058mps.1 | DNM1L | dynamin 1-like (DNM1L) var 7, (NM_001278466) | NM_001278466 |
| uc060tmm.1 | DNM2 | dynamin 2 (DNM2) var 3, (NM_004945) | NM_004945 |
| uc061hfe.1 | DNMT3A | DNA (cytosine-5-)-methyltransferase 3 alpha (DNMT3A) var 2, (NM_153759) | NM_153759 |
| uc059zkr.1 | DPH1 | diphthamide biosynthesis 1 (DPH1), (NM_001383) | NM_001383 |
| uc064xlz.1 | DPH7 | diphthamide biosynthesis 7 (DPH7), (NM_138778) | NM_138778 |
| uc060rze.1 | DPP9 | dipeptidyl-peptidase 9 (DPP9), (NM_139159) | NM_139159 |
| uc063iju.1 | DPYSL3 | dihydropyrimidinase-like 3 (DPYSL3) var 2, (NM_001387) | NM_001387 |
| uc002kwk.5 | DSC2 | desmocollin 2 (DSC2) var Dsc2b, (NM_004949) | NM_004949 |
| uc059jbx.1 | DTWD1 | DTW domain containing 1 (DTWD1) var 2, (NM_001144955) | NM_001144955 |
| uc060sdo.1 | DUS3L | dihydrouridine synthase 3-like (*S. cerevisiae*) (DUS3L) var 1, (NM_020175) | NM_020175 |
| uc060sds.1 | DUS3L | dihydrouridine synthase 3-like (*S. cerevisiae*) (DUS3L) var 1, (NM_020175) | NM_020175 |
| uc010wnn.2 | DYNLL2 | dynein, light chain, LC8-type 2 (DYNLL2), (NM_080677) | NM_080677 |
| uc060rva.1 | EBI3 | Epstein-Barr virus induced 3 (EBI3), (NM_005755) | NM_005755 |
| uc060ttv.1 | ECSIT | ECSIT signalling integrator (ECSIT) var 3, (NM_001142465) | NM_001142465 |
| uc0591kb.1 | EDC3 | enhancer of mRNA decapping 3 (EDC3) var 3, (NM_025083) | NM_025083 |
| uc011lki.2 | EEF1D, | eukaryotic translation elongation factor 1 delta (guanine nucleotide exchange protein) (EEF1D) var | NM_001130057 |
| uc033cfb.1 | EEF1D, | eukaryotic translation elongation factor 1 delta (guanine nucleotide exchange protein) (EEF1D) var | NM_001130057 |
| uc059soq.1 | EIF3CL | eukaryotic translation initiation factor 3, subunit C-like (EIF3CL), (NM_001099661) | NM_001099661 |
| uc059fpj.1 | EIF5 | eukaryotic translation initiation factor 5 (EIF5) var 1, (NM_001969) | NM_001969 |
| uc064eht.1 | ELN | elastin (ELN) var 3, (NM_001081753) | NM_001081753 |
| uc057wfo.1 | EMX2OS | EMX2 opposite strand/antisense RNA (EMX2OS), long non-coding RNA. (NR_002791) | NR_002791 |
| uc062xsy.1 | ENOPH1 | enolase-phosphatase 1 (ENOPH1) var 1, (NM_021204) | NM_021204 |
| uc062xsz.1 | ENOPH1 | enolase-phosphatase 1 (ENOPH1) var 2, (NM_001292017) | NM_001292017 |
| uc060mtq.1 | ENOSF1 | enolase superfamily member 1 (ENOSF1) var 2, (NM_001126123) | NM_001126123 |
| uc065bcs.1 | ENOX2 | ecto-NOX disulfide-thiol exchanger 2 (ENOX2) var 1, (NM_006375) | NM_006375 |
| uc058vib.1 | EP400 | E1A binding protein p400 (EP400), (NM_015409) | NM_015409 |
| uc063rjd.1 | EPB41L2 | erythrocyte membrane protein band 4.1-like 2 (EPB41L2) var 2, (NM_001135555) | NM_001135555 |
| uc063gag.1 | EPB41L4A | erythrocyte membrane protein band 4.1 like 4A (EPB41L4A), (NM_022140) | NM_022140 |
| uc064iwe.1 | EPHA1 | EPH receptor A1 (EPHA1), (NM_005232) | NM_005232 |
| uc064ght.1 | EPHB4 | EPH receptor B4 (EPHB4), (NM_004444) | NM_004444 |
| uc057gll.1 | EPS15 | epidermal growth factor receptor pathway substrate 15 (EPS15) var 1, (NM_001981) | NM_001981 |

TABLE 9-continued

| GeneName | Symbol | Description | RefSeq |
|---|---|---|---|
| uc060uys.1 | EPS15L1 | epidermal growth factor receptor pathway substrate 15-like 1 (EPS15L1) var 3, (NM_001258375) | NM_001258375 |
| uc058pgx.1 | ERBB3 | v-erb-b2 avian erythroblastic leukemia viral oncogene homolog 3 (ERBB3) var 1, (NM_001982) | NM_001982 |
| uc059fov.1 | EXOC3L4 | exocyst complex component 3-like 4 (EXOC3L4), (NM_001077594) | NM_001077594 |
| uc062igr.1 | EXOG | endo/exonuclease (5'-3'), endonuclease G-like (EXOG) var 2, (NM_001145464) | NM_001145464 |
| uc058wlo.1 | EXOSC8 | exosome component 8 (EXOSC8), (NM_181503) | NM_181503 |
| uc063rmk.1 | EYA4 | EYA transcriptional coactivator and phosphatase 4 (EYA4) var 5, (NM_001301012) | NM_001301012 |
| uc011kuh.3 | EZH2 | enhancer of zeste homolog 2 (*Drosophila*) (EZH2) var 4, (NM_001203248) | NM_001203248 |
| uc060vkb.1 | FAM129C | family with sequence similarity 129, member C (FAM129C) var 2, (NM_001098524) | NM_001098524 |
| uc060vkc.1 | FAM129C | family with sequence similarity 129, member C (FAM129C) var 2, (NM_001098524) | NM_001098524 |
| uc011bvm.3 | FAM193A | family with sequence similarity 193, member A (FAM193A) var 4, (NM_001256667) | NM_001256667 |
| uc011bvn.3 | FAM193A | family with sequence similarity 193, member A (FAM193A) var 5, (NM_001256668) | NM_001256668 |
| uc057bod.1 | FAM213B, | family with sequence similarity 213, member B (FAM213B) var 2, (NM_152371), | NM_152371 |
| uc061fvb.1 | FAM213B, | family with sequence similarity 213, member B (FAM213B) var 2, (NM_152371), | NM_152371 |
| uc064tfh.1 | FAM95B1, | family with sequence similarity 95, member B1 (FAM95B1), long non-coding RNA. (NR_026759), | NR_026759 |
| uc064tmd.1 | FAM95B1, | family with sequence similarity 95, member B1 (FAM95B1), long non-coding RNA. (NR_026759), | NR_026759 |
| uc002rpa.2 | FAM98A | family with sequence similarity 98, member A (FAM98A) var 1, (NM_015475) | NM_015475 |
| uc010jnv.2 | FARS2 | phenylalanyl-tRNA synthetase 2, mitochondrial (FARS2), (NM_006567) | NM_006567 |
| uc060lwd.1 | FASN | fatty acid synthase (FASN), (NM_004104) | NM_004104 |
| uc060ynr.1 | FBL | fibrillarin (FBL), (NM_001436) | NM_001436 |
| uc062fcw.1 | FBLN1 | fibulin 1 (FBLN1) var C, (NM_001996) | NM_001996 |
| uc060std.1 | FBN3 | fibrillin 3 (FBN3), (NM_032447) | NM_032447 |
| uc058ttr.1 | FBXO21 | F-box protein 21 (FBXO21) var 1, (NM_033624) | NM_033624 |
| uc060sqj.1 | FCER2 | Fc fragment of IgE, low affinity II, receptor for (CD23) (FCER2) var 1, (NM_002002) | NM_002002 |
| uc060sqm.1 | FCER2 | Fc fragment of IgE, low affinity II, receptor for (CD23) (FCER2) var 1, (NM_002002) | NM_002002 |
| uc058fep.1 | FCHSD2 | FCH and double SH3 domains 2 (FCHSD2), (NM_014824) | NM_014824 |
| uc058fes.1 | FCHSD2 | FCH and double SH3 domains 2 (FCHSD2), (NM_014824) | NM_014824 |
| uc064glm.1 | FIS1 | fission 1 (mitochondrial outer membrane) homolog (*S. cerevisiae*) (FIS1), (NM_016068) | NM_016068 |
| uc058jvh.1 | FKBP4 | FK506 binding protein 4, 59 kDa (FKBP4), (NM_002014) | NM_002014 |
| uc003djj.3 | FLNB | filamin B, beta (FLNB) var 2, (NM_001457) | NM_001457 |
| uc003djk.3 | FLNB | filamin B, beta (FLNB) var 3, (NM_001164318) | NM_001164318 |
| uc003djm.3 | FLNB | filamin B, beta (FLNB) var 4, (NM_001164319) | NM_001164319 |
| uc010hne.3 | FLNB | filamin B, beta (FLNB) var 1, (NM_001164317) | NM_001164317 |
| uc010hnf.3 | FLNB | filamin B, beta (FLNB) var 4, (NM_001164319) | NM_001164319 |
| uc062kyo.1 | FLNB | filamin B, beta (FLNB) var 4, (NM_001164319) | NM_001164319 |
| uc059prq.1 | FLYWCH1 | FLYWCH-type zinc finger 1 (FLYWCH1) var 1, (NM_032296) | NM_032296 |
| uc061sdc.1 | FN1 | fibronectin 1 (FN1) var 5, (NM_212476) | NM_212476 |
| uc064mnv.1 | FNTA | farnesyltransferase, CAAX box, alpha (FNTA) var 1, (NM_002027) | NM_002027 |
| uc062lln.1 | FOXP1 | forkhead box P1 (FOXP1) var 6, (NM_001244813) | NM_001244813 |
| uc064vxp.1 | FPGS | folylpolyglutamate synthase (FPGS) var 1, (NM_004957) | NM_004957 |
| uc064vxr.1 | FPGS | folylpolyglutamate synthase (FPGS) var 1, (NM_004957) | NM_004957 |
| uc058djl.1 | FRMD8 | FERM domain containing 8 (FRMD8) var 1, (NM_031904) | NM_031904 |
| uc058djm.1 | FRMD8 | FERM domain containing 8 (FRMD8) var 2, (NM_001300832) | NM_001300832 |
| uc062mwn.1 | FSTL1 | follistatin-like 1 (FSTL1), (NM_007085) | NM_007085 |
| uc060iqx.1 | FTSJ3 | FtsJ homolog 3 (*E. coli*) (FTSJ3), (NM_017647) | NM_017647 |
| uc060irb.1 | FTSJ3 | FtsJ homolog 3 (*E. coli*) (FTSJ3), (NM_017647) | NM_017647 |
| uc057wzg.1 | FUOM | fucose mutarotase (FUOM) var 1, (NM_001098483) | NM_001098483 |
| uc060atq.1 | FXR2 | fragile X mental retardation, autosomal homolog 2 (FXR2), (NM_004860) | NM_004860 |
| uc058huk.1 | FXYD2 | FXYD domain containing ion transport regulator 2 (FXYD2) var b, (NM_021603) | NM_021603 |
| uc060wyx.1 | FXYD3 | FXYD domain containing ion transport regulator 3 (FXYD3) var 1, (NM_005971) | NM_005971 |
| uc004doi.6 | GAGE13 | G antigen 2C (GAGE2C), (NM_001472) | NM_001472 |
| uc059jas.1 | GALK2 | galactokinase 2 (GALK2) var 2, (NM_001001556) | NM_001001556 |
| uc063iyn.1 | GALNT10 | polypeptide N-acetylgalactosaminyltransferase 10 (GALNT10), (NM_198321) | NM_198321 |
| uc061zqx.1 | GART | phosphoribosylglycinamide formyltransferase, phosphoribosylglycinamide synthetase, phosphoribosylaminoimidazole synthetase (GART) var 2, (NM_175085) | NM_175085 |
| uc059yvt.1 | GAS8 | growth arrest-specific 8 (GAS8) var 5, (NM_001286209) | NM_001286209 |
| uc059yvw.1 | GAS8 | growth arrest-specific 8 (GAS8) var 4, (NM_001286208) | NM_001286208 |
| uc060wah.1 | GATAD2A | GATA zinc finger domain containing 2A (GATAD2A) var 2, (NM_017660) | NM_017660 |
| uc062das.1 | GATSL3 | GATS protein-like 3 (GATSL3), (NM_001037666) | NM_001037666 |
| uc062daw.1 | GATSL3 | GATS protein-like 3 (GATSL3), (NM_001037666) | NM_001037666 |
| uc062dbe.1 | GATSL3 | GATS protein-like 3 (GATSL3), (NM_001037666) | NM_001037666 |
| uc064dtx.1 | GBAS | glioblastoma amplified sequence (GBAS) var 1, (NM_001483) | NM_001483 |
| uc060uez.1 | GCDH | glutaryl-CoA dehydrogenase (GCDH) var 2, (NM_013976) | NM_013976 |
| uc058tzd.1 | GCN1L1 | GCN1 general control of amino-acid synthesis 1-like 1 (yeast) (GCN1L1), (NM_006836) | NM_006836 |
| uc058tzh.1 | GCN1L1 | GCN1 general control of amino-acid synthesis 1-like 1 (yeast) (GCN1L1), (NM_006836) | NM_006836 |
| uc060djs.1 | GIT1 | G protein-coupled receptor kinase interacting ArfGAP 1 (GIT1) var 2, (NM_014030) | NM_014030 |
| uc061suk.1 | GLB1L | galactosidase, beta 1-like (GLB1L) var 3, (NM_001286427) | NM_001286427 |
| uc062kpb.1 | GLT8D1 | glycosyltransferase 8 domain containing 1 (GLT8D1) var 2, (NM_018446) | NM_018446 |
| uc063mrx.1 | GNL1, | guanine nucleotide binding protein-like 1 (GNL1), (NM_005275), | NM_005275 |
| uc063mrz.1 | GNL1, | guanine nucleotide binding protein-like 1 (GNL1), (NM_005275), | NM_005275 |
| uc063tfz.1 | GNL1, | guanine nucleotide binding protein-like 1 (GNL1), (NM_005275), | NM_005275 |
| uc063tvq.1 | GNL1, | guanine nucleotide binding protein-like 1 (GNL1), (NM_005275), | NM_005275 |
| uc063tvs.1 | GNL1, | guanine nucleotide binding protein-like 1 (GNL1), (NM_005275), | NM_005275 |
| uc063vbo.1 | GNL1, | guanine nucleotide binding protein-like 1 (GNL1), (NM_005275), | NM_005275 |
| uc063vbq.1 | GNL1, | guanine nucleotide binding protein-like 1 (GNL1), (NM_005275), | NM_005275 |
| uc063whd.1 | GNL1, | guanine nucleotide binding protein-like 1 (GNL1), (NM_005275), | NM_005275 |
| uc063whf.1 | GNL1, | guanine nucleotide binding protein-like 1 (GNL1), (NM_005275), | NM_005275 |
| uc063xgm.1 | GNL1, | guanine nucleotide binding protein-like 1 (GNL1), (NM_005275), | NM_005275 |
| uc063xgo.1 | GNL1, | guanine nucleotide binding protein-like 1 (GNL1), (NM_005275), | NM_005275 |

TABLE 9-continued

| GeneName | Symbol | Description | RefSeq |
|---|---|---|---|
| uc063ymi.1 | GNL1, | guanine nucleotide binding protein-like 1 (GNL1), (NM_005275), | NM_005275 |
| uc063ymk.1 | GNL1, | guanine nucleotide binding protein-like 1 (GNL1), (NM_005275), | NM_005275 |
| uc063zsd.1 | GNL1, | guanine nucleotide binding protein-like 1 (GNL1), (NM_005275), | NM_005275 |
| uc063zsf.1 | GNL1, | guanine nucleotide binding protein-like 1 (GNL1), (NM_005275), | NM_005275 |
| uc002whp.2 | GNRH2 | gonadotropin-releasing hormone 2 (GNRH2) var 3, (NM_178331) | NM_178331 |
| uc002whr.2 | GNRH2 | gonadotropin-releasing hormone 2 (GNRH2) var 1, (NM_001501) | NM_001501 |
| uc061vcw.1 | GNRH2 | gonadotropin-releasing hormone 2 (GNRH2) var 2, (NM_178332) | NM_178332 |
| uc059lgi.1 | GOLGA6A | golgin A6 family, member A (GOLGA6A), (NM_001038640) | NM_001038640 |
| uc057dtw.1 | GPATCH3 | G patch domain containing 3 (GPATCH3), (NM_022078) | NM_022078 |
| uc062hus.1 | GPD1L | glycerol-3-phosphate dehydrogenase 1-like (GPD1L), (NM_015141) | NM_015141 |
| uc061rtp.1 | GPR1 | G protein-coupled receptor 1 (GPR1) var 4, (NM_001261453) | NM_001261453 |
| uc059uvj.1 | GPR56 | adhesion G protein-coupled receptor G1 (ADGRG1) var 7, (NM_001145774) | NM_001145774 |
| uc060and.1 | GPS2 | G protein pathway suppressor 2 (GPS2), (NM_004489) | NM_004489 |
| uc064roh.1 | GPT | glutamic-pyruvate transaminase (alanine aminotransferase) (GPT), (NM_005309) | NM_005309 |
| uc063ixf.1 | GRIA1 | glutamate receptor, ionotropic, AMPA 1 (GRIA1) var 7, (NM_001258023) | NM_001258023 |
| uc057idf.1 | GTF2B | general transcription factor IIB (GTF2B), (NM_001514) | NM_001514 |
| uc001moi.3 | GTF2H1 | general transcription factor IIH, polypeptide 1, 62 kDa (GTF2H1) var 2, (NM_001142307) | NM_001142307 |
| uc058waz.1 | GTF3A | general transcription factor IIIA (GTF3A), (NM_002097) | NM_002097 |
| uc064wsm.1 | GTF3C4 | general transcription factor IIIC, polypeptide 4, 90 kDa (GTF3C4), (NM_012204) | NM_012204 |
| uc004cci.5 | GTF3C5 | general transcription factor IIIC, polypeptide 5, 63 kDa (GTF3C5) var 2, (NM_012087) | NM_012087 |
| uc033dju.2 | GTF3C5 | general transcription factor IIIC, polypeptide 5, 63 kDa (GTF3C5) var 3, (NM_001286709) | NM_001286709 |
| uc057reu.1 | GTPBP4 | GTP binding protein 4 (GTPBP4), (NM_012341) | NM_012341 |
| uc064xvf.1 | GYG2 | glycogenin 2 (GYG2) var 4, (NM_001184703) | NM_001184703 |
| uc063mxv.1 | HCG22 | HLA complex group 22 (HCG22), long non-coding RNA. (NR_003948) | NR_003948 |
| uc062kga.1 | HEMK1 | HemK methyltransferase family member 1 (HEMK1), (NM_016173) | NM_016173 |
| uc057ivq.1 | HENMT1 | HEN1 methyltransferase homolog 1 (Arabidopsis) (HENMT1) var 2, (NM_001102592) | NM_001102592 |
| uc060lmt.1 | HGS | hepatocyte growth factor-regulated tyrosine kinase substrate (HGS), (NM_004712) | NM_004712 |
| uc061afd.1 | HIF3A | hypoxia inducible factor 3, alpha subunit (HIF3A) var 4, (NM_152796) | NM_152796 |
| uc061aff.1 | HIF3A | hypoxia inducible factor 3, alpha subunit (HIF3A) var 4, (NM_152796) | NM_152796 |
| uc001udj.2 | HIP1R | huntingtin interacting protein 1 related (HIP1R) var 1, (NM_003959) | NM_003959 |
| uc058uor.1 | HIP1R | huntingtin interacting protein 1 related (HIP1R) var 1, (NM_003959) | NM_003959 |
| uc058uot.1 | HIP1R | huntingtin interacting protein 1 related (HIP1R) var 1, (NM_003959) | NM_003959 |
| uc003nhf.4 | HIST1H4G | histone cluster 1, H4g (HIST1H4G), (NM_003547) | NM_003547 |
| uc060xtr.1 | HKR1 | HKR1, GLI-Kruppel zinc finger family member (HKR1), (NM_181786) | NM_181786 |
| uc063nrr.1 | HLA-DQB2, | major histocompatibility complex, class II, DQ beta 2 (HLA-DQB2) var 2, (NM_001198858), | NM_001198858 |
| uc064alr.1 | HLA-DQB2, | major histocompatibility complex, class II, DQ beta 2 (HLA-DQB2) var 2, (NM_001198858), | NM_001198858 |
| uc059mpd.1 | HOMER2 | homer scaffolding protein 2 (HOMER2) var 1, (NM_004839) | NM_004839 |
| uc057zpz.1 | HPS5 | Hermansky-Pudlak syndrome 5 (HPS5) var 3, (NM_181508) | NM_181508 |
| uc057zqa.1 | HPS5 | Hermansky-Pudlak syndrome 5 (HPS5) var 3, (NM_181508) | NM_181508 |
| uc063gye.1 | HSPA4 | heat shock 70 kDa protein 4 (HSPA4), (NM_002154) | NM_002154 |
| uc062kdo.1 | HYAL1 | hyaluronoglucosaminidase 1 (HYAL1) var 2, (NM_153282) | NM_153282 |
| uc057uwb.1 | IDE | insulin-degrading enzyme (IDE) var 2, (NM_001165946) | NM_001165946 |
| uc064mgi.1 | IDO2 | indoleamine 2,3-dioxygenase 2 (IDO2), (NM_194294) | NM_194294 |
| uc062uib.1 | IDUA | iduronidase, alpha-L- (IDUA) var 1, (NM_000203) | NM_000203 |
| uc059erh.1 | IFI27L1, | interferon, alpha-inducible protein 27-like 1 (IFI27L1) var 1, (NM_145249) | NM_145249 |
| uc059gnj.1 | IFI27L1, | interferon, alpha-inducible protein 27-like 1 (IFI27L1) var 1, (NM_145249), | NM_145249 |
| uc058hzx.1 | IFT46 | intraflagellar transport 46 (IFT46) var 2, (NM_001168618) | NM_001168618 |
| uc064sma.1 | IFT74 | intraflagellar transport 74 (IFT74) var 4, (NM_001099224) | NM_001099224 |
| uc059kja.1 | IGDCC3 | immunoglobulin superfamily, DCC subclass, member 3 (IGDCC3), (NM_004884) | NM_004884 |
| uc058pgk.1 | IKZF4 | IKAROS family zinc finger 4 (Eos) (IKZF4), (NM_022465) | NM_022465 |
| uc061mlw.1 | IL1R1 | interleukin 1 receptor, type I (IL1R1) var 2, (NM_001288706) | NM_001288706 |
| uc063dsb.1 | IL6ST | interleukin 6 signal transducer (IL6ST) var 1, (NM_002184) | NM_002184 |
| uc063dsj.1 | IL6ST | interleukin 6 signal transducer (IL6ST) var 3, (NM_001190981) | NM_001190981 |
| uc060tkx.1 | ILF3 | interleukin enhancer binding factor 3, 90 kDa (ILF3) var 3, (NM_153464) | NM_153464 |
| uc060tla.1 | ILF3 | interleukin enhancer binding factor 3, 90 kDa (ILF3) var 4, (NM_017620) | NM_017620 |
| uc060urt.1 | ILVBL | ilvB (bacterial acetolactate synthase)-like (ILVBL), (NM_006844) | NM_006844 |
| uc057wxq.1 | INPP5A | inositol polyphosphate-5-phosphatase, 40 kDa (INPP5A), (NM_005539) | NM_005539 |
| uc058xwf.1 | IPO5 | importin 5 (IPO5), (NM_002271) | NM_002271 |
| uc065cai.1 | IRAK1 | interleukin-1 receptor-associated kinase 1 (IRAK1) var 2, (NM_001025242) | NM_001025242 |
| uc057sqo.1 | ITGB1 | integrin, beta 1 (fibronectin receptor, beta polypeptide, antigen CD29 includes MDF2, MSK12) (ITGB1) var1D, (NM_033668) | NM_033668 |
| uc058omr.1 | ITGB7 | integrin, beta 7 (ITGB7) var 1, (NM_000889) | NM_000889 |
| uc061ztm.1 | ITSN1 | intersectin 1 (SH3 domain protein) (ITSN1) var 2, (NM_001001132) | NM_001001132 |
| uc061hcx.1 | ITSN2 | intersectin 2 (ITSN2) var 2, (NM_147152) | NM_147152 |
| uc061nqc.1 | IWS1 | IWS1 homolog (S. cerevisiae) (IWS1), (NM_017969) | NM_017969 |
| uc063hbu.1 | JADE2 | jade family PHD finger 2 (JADE2) var 3, (NM_015288) | NM_015288 |
| uc063hbv.1 | JADE2 | jade family PHD finger 2 (JADE2) var 3, (NM_015288) | NM_015288 |
| uc062gol.1 | JAGN1 | jagunal homolog 1 (JAGN1), (NM_032492) | NM_032492 |
| uc010bcm.2 | JMJD7 | jumonji domain containing 7 (JMJD7), (NM_001114632) | NM_001114632 |
| uc061lwd.1 | KANSL3 | KAT8 regulatory NSL complex subunit 3 (KANSL3) var 7, non-coding RNA. (NR_047658) | NR_047658 |
| uc058dom.1 | KAT5 | K(lysine) acetyltransferase 5 (KAT5) var 2, (NM_006388) | NM_006388 |
| uc058doo.1 | KAT5 | K(lysine) acetyltransferase 5 (KAT5) var 3, (NM_182709) | NM_182709 |
| uc062lif.1 | KBTBD8 | kelch repeat and BTB (POZ) domain containing 8 (KBTBD8), (NM_032505) | NM_032505 |
| uc062lig.1 | KBTBD8 | kelch repeat and BTB (POZ) domain containing 8 (KBTBD8), (NM_032505) | NM_032505 |
| uc062pgf.1 | KCNAB1 | potassium channel, voltage gated subfamily A regulatory beta subunit 1 (KCNAB1) var 1, (NM_172160) | NM_172160 |
| uc059gfj.1 | KIAA0125 | KIAA0125 (KIAA0125), long non-coding RNA. (NR_026800) | NR_026800 |
| uc059gjv.1 | KIAA0125 | KIAA0125 (KIAA0125), long non-coding RNA. (NR_026800) | NR_026800 |

TABLE 9-continued

| GeneName | Symbol | Description | RefSeq |
|---|---|---|---|
| uc060jxt.1 | KIAA0195 | KIAA0195 (KIAA0195), (NM_014738) | NM_014738 |
| uc059auf.1 | KIAA0391 | KIAA0391 (KIAA0391) var 2, (NM_001256678) | NM_001256678 |
| uc059sub.1 | KIF22 | kinesin family member 22 (KIF22) var 1, (NM_007317) | NM_007317 |
| uc064zso.1 | KIF4A | kinesin family member 4A (KIF4A), (NM_012310) | NM_012310 |
| uc064rnn.1 | KIFC2 | kinesin family member C2 (KIFC2), (NM_145754) | NM_145754 |
| uc064bys.1 | KLHL7 | kelch-like family member 7 (KLHL7) var 1, (NM_001031710) | NM_001031710 |
| uc060fbs.1 | KRT19 | keratin 19, type I (KRT19), (NM_002276) | NM_002276 |
| uc058oie.1 | KRT73-AS1 | KRT73 antisense RNA 1 (KRT73-AS1), long non-coding RNA. (NR_126005) | NR_126005 |
| uc002zfs.1 | KRTAP12-4 | keratin associated protein 12-4 (KRTAP12-4), (NM_198698) | NM_198698 |
| uc059bik.1 | L2HGDH | L-2-hydroxyglutarate dehydrogenase (L2HGDH), (NM_024884) | NM_024884 |
| uc059bil.1 | L2HGDH | L-2-hydroxyglutarate dehydrogenase (L2HGDH), (NM_024884) | NM_024884 |
| uc061xdd.1 | L3MBTL1 | l(3)mbt-like 1 (*Drosophila*) (L3MBTL1) var I, (NM_015478) | NM_015478 |
| uc057ohy.1 | LAD1 | ladinin 1 (LAD1), (NM_005558) | NM_005558 |
| uc057ohz.1 | LAD1 | ladinin 1 (LAD1), (NM_005558) | NM_005558 |
| uc064wom.1 | LAMC3 | laminin, gamma 3 (LAMC3), (NM_006059) | NM_006059 |
| uc003cop.2 | LARS2 | leucyl-tRNA synthetase 2, mitochondrial (LARS2), (NM_015340) | NM_015340 |
| uc062ixl.1 | LARS2 | leucyl-tRNA synthetase 2, mitochondrial (LARS2), (NM_015340) | NM_015340 |
| uc057laj.1 | LCE1E | late cornified envelope 1E (LCE1E), (NM_178353) | NM_178353 |
| uc064xgd.1 | LCN12 | lipocalin 12 (LCN12), (NM_178536) | NM_178536 |
| uc060nql.1 | LDLRAD4 | low density lipoprotein receptor class A domain containing 4 (LDLRAD4) var a1, (NM_181481) | NM_181481 |
| uc011cfk.3 | LEF1 | lymphoid enhancer-binding factor 1 (LEF1) var 4, (NM_001166119) | NM_001166119 |
| uc062ywq.1 | LEF1 | lymphoid enhancer-binding factor 1 (LEF1) var 4, (NM_001166119) | NM_001166119 |
| uc062ywz.1 | LEF1 | lymphoid enhancer-binding factor 1 (LEF1) var 4, (NM_001166119) | NM_001166119 |
| uc057otb.1 | LEMD1 | LEM domain containing 1 (LEMD1) var 4, (NM_001199052) | NM_001199052 |
| uc057otc.1 | LEMD1 | LEM domain containing 1 (LEMD1) var 4, (NM_001199052) | NM_001199052 |
| uc062umv.1 | LETM1 | leucine zipper-EF-hand containing transmembrane protein 1 (LETM1), (NM_012318) | NM_012318 |
| uc060kxh.1 | LGALS3BP | lectin, galactoside-binding, soluble, 3 binding protein (LGALS3BP), (NM_005567) | NM_005567 |
| uc060cek.1 | LGALS9C | lectin, galactoside-binding, soluble, 9C (LGALS9C), (NM_001040078) | NM_001040078 |
| uc009yaj.3 | LHPP | phospholysine phosphohistidine inorganic pyrophosphate phosphatase (LHPP) var 2, (NM_001167880) | NM_001167880 |
| uc061aqf.1 | LIG1 | ligase I, DNA, ATP-dependent (LIG1) var 1, (NM_000234) | NM_000234 |
| uc061nqu.1 | LIMS2 | LIM and senescent cell antigen-like domains 2 (LIMS2) var 4, (NM_001256542) | NM_001256542 |
| uc058wse.1 | LINC00284 | long intergenic non-protein coding RNA 284 (LINC00284), long non-coding RNA. (NR_026955) | NR_026955 |
| uc058ujc.1 | LINC01089 | long intergenic non-protein coding RNA 1089 (LINC01089), long non-coding RNA. (NR_002809) | NR_002809 |
| uc063epk.1 | LINC01336 | long intergenic non-protein coding RNA 1336 (LINC01336), long non-coding RNA. (NR_126375) | NR_126375 |
| uc057lvz.1 | LMNA | lamin A/C (LMNA) var 5, (NM_001282624) | NM_001282624 |
| uc057lwf.1 | LMNA | lamin A/C (LMNA) var 3, (NM_170708) | NM_170708 |
| uc060umo.1 | LPHN1 | adhesion G protein-coupled receptor L1 (ADGRL1) var 2, (NM_014921) | NM_014921 |
| uc058bpn.1 | LPXN | leupaxin (LPXN) var 2, (NM_004811) | NM_004811 |
| uc063ady.1 | LRBA | LPS-responsive vesicle trafficking, beach and anchor containing (LRBA) var 2, (NM_006726) | NM_006726 |
| uc058kne.1 | LRRC23 | leucine rich repeat containing 23 (LRRC23) var 2, (NM_006992) | NM_006992 |
| uc060ltc.1 | LRRC45 | leucine rich repeat containing 45 (LRRC45), (NM_144999) | NM_144999 |
| uc001akx.2 | LRRC47 | leucine rich repeat containing 47 (LRRC47), (NM_020710) | NM_020710 |
| uc002gqg.3 | LRRC75A | leucine rich repeat containing 75A (LRRC75A) var 1, (NM_001113567) | NM_001113567 |
| uc063tkx.1 | LSM2, | LSM2 homolog, U6 small nuclear RNA associated (*S. cerevisiae*) (LSM2), (NM_021177), | NM_021177 |
| uc063ujn.1 | LSM2, | LSM2 homolog, U6 small nuclear RNA associated (*S. cerevisiae*) (LSM2), (NM_021177), | NM_021177 |
| uc063voz.1 | LSM2, | LSM2 homolog, U6 small nuclear RNA associated (*S. cerevisiae*) (LSM2), (NM_021177), | NM_021177 |
| uc063xtz.1 | LSM2, | LSM2 homolog, U6 small nuclear RNA associated (*S. cerevisiae*) (LSM2), (NM_021177), | NM_021177 |
| uc063yzr.1 | LSM2, | LSM2 homolog, U6 small nuclear RNA associated (*S. cerevisiae*) (LSM2), (NM_021177), | NM_021177 |
| uc064cqe.1 | LSM5 | LSM5 homolog, U6 small nuclear RNA associated (*S. cerevisiae*) (LSM5) var 1, (NM_012322) | NM_012322 |
| uc011gbw.3 | TA, | lymphotoxin alpha (LTA) var 2, (NM_000595), | NM_000595 |
| uc011hqv.3 | LTA, | lymphotoxin alpha (LTA) var 2, (NM_000595), | NM_000595 |
| uc011iof.3 | LTA, | lymphotoxin alpha (LTA) var 2, (NM_000595), | NM_000595 |
| uc063ude.1 | LTA, | lymphotoxin alpha (LTA) var 2, (NM_000595), | NM_000595 |
| uc010jnu.5 | LYRM4 | LYR motif containing 4 (LYRM4) var 3, (NM_001164841) | NM_001164841 |
| uc057vlr.1 | LZTS2 | leucine zipper, putative tumor suppressor 2 (LZTS2) (NM_032429) | NM_032429 |
| uc057vlt.1 | LZTS2 | leucine zipper, putative tumor suppressor 2 (LZTS2), (NM_032429) | NM_032429 |
| uc059ian.1 | MAPKBP1 | mitogen-activated protein kinase binding protein 1 (MAPKBP1) var 3, (NM_001265611) | NM_001265611 |
| uc063ecv.1 | MAST4 | microtubule associated serine/threonine kinase family member 4 (MAST4) var 4, (NM_001290226) | NM_001290226 |
| uc059awv.1 | MBIP | MAP3K12 binding inhibitory protein 1 (MBIP) var 2, (NM_001144891) | NM_001144891 |
| uc003fle.4 | MCCC1 | methylcrotonoyl-CoA carboxylase 1 (alpha) (MCCC1) var 1, (NM_020166) | NM_020166 |
| uc062qnd.1 | MCCC1 | methylcrotonoyl-CoA carboxylase 1 (alpha) (MCCC1) var 1, (NM_020166) | NM_020166 |
| uc062qne.1 | MCCC1 | methylcrotonoyl-CoA carboxylase 1 (alpha) (MCCC1) var 1, (NM_020166) | NM_020166 |
| uc001jtc.3 | MCU | mitochondrial calcium uniporter (MCU) var 1, (NM_138357) | NM_138357 |
| uc057tzd.1 | MCU | mitochondrial calcium uniporter (MCU) var 1, (NM_138357) | NM_138357 |
| uc003pnn.2 | MDN1 | MDN1, midasin homolog (yeast) (MDN1), (NM_014611) | NM_014611 |
| uc063qcd.1 | MDN1 | MDN1, midasin homolog (yeast) (MDN1), (NM_014611) | NM_014611 |
| uc062pue.1 | MECOM | MDS1 and EVI1 complex locus (MECOM) var 3, (NM_001105078) | NM_001105078 |
| uc060ewj.1 | MED24 | mediator complex subunit 24 (MED24) var 1, (NM_014815) | NM_014815 |
| uc064ged.1 | MEPCE | methylphosphate capping enzyme (MEPCE) var 4, (NM_001194992) | NM_001194992 |
| uc064iaz.1 | MEST | mesoderm specific transcript (MEST) var 3, (NM_177525) | NM_177525 |
| uc001gia.4 | METTL13 | methyltransferase like 13 (METTL13) var 2, (NM_014955) | NM_014955 |
| uc059znk.1 | METTL16 | methyltransferase like 16 (METTL16), (NM_024086) | NM_024086 |
| uc062dxv.1 | MFNG | MFNG O-fucosylpeptide 3-beta-N-acetylglucosaminyltransferase (MFNG) var 1, (NM_002405) | NM_002405 |
| uc060ccx.1 | MIEF2 | mitochondrial elongation factor 2 (MIEF2) var 1, (NM_139162) | NM_139162 |
| uc064bkt.1 | MIOS | missing oocyte, meiosis regulator, homolog (Drosophila) (MIOS), (NM_019005) | NM_019005 |
| uc032ylk.1 | MIR3135B, | microRNA 3135b (MIR3135B), microRNA. (NR_039668), | NR_039668 |
| uc032ytr.1 | MIR3135B, | microRNA 3135b (MIR3135B), microRNA. (NR_039668), | NR_039668 |

TABLE 9-continued

| GeneName | Symbol | Description | RefSeq |
|---|---|---|---|
| uc021uqm.1 | MIR3188 | microRNA 3188 (MIR3188), microRNA. (NR_036155) | NR_036155 |
| uc031yjg.1 | MIR6090 | microRNA 6090 (MIR6090), microRNA. (NR_106738) | NR_106738 |
| uc059pjc.1 | MLST8 | MTOR associated protein, LST8 homolog (*S. cerevisiae*) (MLST8) var 1, (NM_022372) | NM_022372 |
| uc058vgw.1 | MMP17 | matrix metallopeptidase 17 (membrane-inserted) (MMP17), (NM_016155) | NM_016155 |
| uc057vfm.1 | MMS19 | MMS19 nucleotide excision repair homolog (*S. cerevisiae*) (MMS19) var 2, (NM_001289403) | NM_001289403 |
| uc059lni.1 | MPI | mannose phosphate isomerase (MPI) var 2, (NM_001289155) | NM_001289155 |
| uc060fve.1 | MPP2 | membrane protein, palmitoylated 2 (MAGUK p55 subfamily member 2) (MPP2) var 9, (NM_001278381) | NM_001278381 |
| uc003xsa.3 | MRPL15 | mitochondrial ribosomal protein L15 (MRPL15), (NM_014175) | NM_014175 |
| uc060hhd.1 | MRPL27 | mitochondrial ribosomal protein L27 (MRPL27), (NM_016504) | NM_016504 |
| uc060hhf.1 | MRPL27 | mitochondrial ribosomal protein L27 (MRPL27), (NM_016504) | NM_016504 |
| uc059mwq.1 | MRPL46 | mitochondrial ribosomal protein L46 (MRPL46), (NM_022163) | NM_022163 |
| uc063ekk.1 | MRPS27 | mitochondrial ribosomal protein S27 (MRPS27) var 3, (NM_001286751) | NM_001286751 |
| uc064nwv.1 | MRPS28 | mitochondrial ribosomal protein S28 (MRPS28), (NM_014018) | NM_014018 |
| uc010yjt.3 | MSGN1 | mesogenin 1 (MSGN1), (NM_001105569) | NM_001105569 |
| uc062uwx.1 | MSX1 | msh homeobox 1 (MSX1), (NM_002448) | NM_002448 |
| uc001yqy.4 | MTA1 | metastasis associated 1 (MTA1) var 2, (NM_001203258) | NM_001203258 |
| uc061ipp.1 | MTA3 | metastasis associated 1 family, member 3 (MTA3) var 3, (NM_020744) | NM_020744 |
| uc057dns.1 | MTFR1L | mitochondrial fission regulator 1-like (MTFR1L) var 1, (NM_019557) | NM_019557 |
| uc063sgp.1 | MTHFD1L | methylenetetrahydrofolate dehydrogenase (NADP+ dependent) 1-like (MTHFD1L) var 3, (NM_001242768) | NM_001242768 |
| uc058xpe.1 | MYCBP2 | MYC binding protein 2, E3 ubiquitin protein ligase (MYCBP2), (NM_015057) | NM_015057 |
| uc060ehm.1 | MYO19 | myosin XIX (MYO19) var 3, (NM_001033580) | NM_001033580 |
| uc059zff.1 | MYO1C | myosin IC (MYO1C) var 2, (NM_001080950) | NM_001080950 |
| uc059zfp.1 | MYO1C | myosin IC (MYO1C) var 2, (NM_001080950) | NM_001080950 |
| uc001udy.2 | n/a | n/a | NM_001304835 |
| uc002fjp.3 | n/a | n/a | NM_001159380 |
| uc002gnz.5 | n/a | n/a | NM_018127 |
| uc002gva.2 | n/a | n/a | NM_001291905 |
| uc002gvb.2 | n/a | n/a | NM_001291905 |
| uc002iii.2 | n/a | n/a | NM_001303442 |
| uc003lmr.4 | n/a | n/a | NM_001144935 |
| uc003zjz.4 | n/a | n/a | NR_046386 |
| uc010dzm.2 | n/a | n/a | NR_046366 |
| uc010jba.3 | n/a | n/a | NR_003149 |
| uc010mdi.4 | n/a | n/a | NR_037873 |
| uc010yly.3 | n/a | n/a | NM_001271287 |
| uc011kkq.2 | n/a | n/a | NR_038967 |
| uc021qlu.2 | n/a | n/a | NM_001242482 |
| uc032qsv.2 | n/a | n/a | NR_034118 |
| uc032qyp.2 | n/a | n/a | NR_034118 |
| uc032tgw.1 | n/a | n/a | NM_001278363 |
| uc057axr.1 | n/a | n/a | NR_026874 |
| uc057bnh.1 | n/a | n/a | NR_037844 |
| uc057hsg.1 | n/a | n/a | NR_073562 |
| uc057icn.1 | n/a | n/a | NR_026986 |
| uc057ijq.1 | n/a | n/a | NR_034089 |
| uc057ipd.1 | n/a | n/a | NR_033716 |
| uc057jor.1 | n/a | n/a | NM_001253853 |
| uc057lqe.1 | n/a | n/a | NM_001278229 |
| uc057oir.1 | n/a | n/a | NM_001193570 |
| uc057wmj.1 | /a | n/a | NM_001167865 |
| uc057wxg.1 | n/a | n/a | NR_026559 |
| uc057zdl.1 | n/a | n/a | NM_001018057 |
| uc057zoc.1 | n/a | n/a | NR_104041 |
| uc058ayk.1 | n/a | n/a | NM_001184751 |
| uc058dls.1 | n/a | n/a | NM_001164266 |
| uc058exu.1 | n/a | n/a | NR_104476 |
| uc058fzu.1 | n/a | n/a | NM_001286060 |
| uc058gdh.1 | n/a | n/a | NM_001193538 |
| uc058hfs.1 | n/a | n/a | NR_038364 |
| uc058hrr.1 | n/a | n/a | NR_110282 |
| uc058jqr.1 | n/a | n/a | NM_001297421 |
| uc058lgl.1 | n/a | n/a | NM_001291315 |
| uc058msp.1 | n/a | n/a | NM_173600 |
| uc058myu.1 | n/a | n/a | NM_001077484 |
| uc058rwz.1 | n/a | n/a | NR_038241 |
| uc058tuf.1 | n/a | n/a | NM_001206801 |
| uc058uon.1 | n/a | n/a | NM_001303097 |
| uc058upr.1 | n/a | n/a | NM_001304834 |
| uc058upt.1 | n/a | n/a | NM_001304835 |
| uc058yvg.1 | n/a | n/a | NR_033909 |
| uc059aun.1 | n/a | n/a | NR_104110 |
| uc059hcz.1 | n/a | n/a | NM_001243538 |
| uc059hkf.1 | n/a | n/a | NM_001290232 |
| uc059hul.1 | n/a | n/a | NM_001304802 |
| uc059iqz.1 | n/a | n/a | NR_125376 |
| uc059jcf.1 | n/a | n/a | NR_073597 |

TABLE 9-continued

| GeneName | Symbol | Description | RefSeq |
|---|---|---|---|
| uc059ols.1 | n/a | n/a | NM_001172665 |
| uc059otm.1 | n/a | n/a | NR_033645 |
| uc059qij.1 | n/a | n/a | NR_040252 |
| uc059rhp.1 | n/a | n/a | NR_036447 |
| uc059xki.1 | n/a | n/a | NM_001291997 |
| uc059xwd.1 | n/a | n/a | NM_001291454 |
| uc059yne.1 | n/a | n/a | NR_045839 |
| uc060bsq.1 | n/a | n/a | NR_027175 |
| uc060cik.1 | n/a | n/a | NM_001291904 |
| uc060fvx.1 | n/a | n/a | NM_001304814 |
| uc060hxx.1 | n/a | n/a | NR_038416 |
| uc060ipk.1 | n/a | n/a | NM_001003786 |
| uc060myc.1 | n/a | n/a | NM_001278684 |
| uc060nfo.1 | n/a | n/a | NM_001083625 |
| uc060nmt.1 | n/a | n/a | NM_001303526 |
| uc060qln.1 | n/a | n/a | NM_001303471 |
| uc060tmn.1 | n/a | n/a | NR_104015 |
| uc060zfv.1 | n/a | n/a | NR_073051 |
| uc061bfs.1 | n/a | n/a | NM_001270960 |
| uc061bnb.1 | n/a | n/a | NM_001193357 |
| uc061bnn.1 | n/a | n/a | NM_001258017 |
| uc061dkz.1 | n/a | n/a | NM_001291745 |
| uc061fuf.1 | n/a | n/a | NR_037844 |
| uc061gqf.1 | n/a | n/a | NM_182626 |
| uc061irb.1 | n/a | n/a | NR_073394 |
| uc061kqd.1 | n/a | n/a | NR_029403 |
| uc061nvl.1 | n/a | n/a | NM_001105193 |
| uc061plb.1 | n/a | n/a | NR_110576 |
| uc061plc.1 | n/a | n/a | NR_110576 |
| uc061sne.1 | n/a | n/a | NM_001079866 |
| uc061tok.1 | n/a | n/a | NR_046476 |
| uc061vea.1 | n/a | n/a | NM_001287524 |
| uc061vlr.1 | n/a | n/a | NR_029377 |
| uc061vyu.1 | n/a | n/a | NR_110001 |
| uc061wtr.1 | ln/a | n/a | NM_001199513 |
| uc061xwg.1 | n/a | n/a | NM_198433 |
| uc061xwh.1 | n/a | n/a | NM_198433 |
| uc061yty.1 | n/a | n/a | NM_001283052 |
| uc062evq.1 | n/a | n/a | INR_104301 |
| uc062evs.1 | n/a | n/a | NR_104301 |
| uc062evt.1 | n/a | n/a | NR_104300 |
| uc062fel.1 | n/a | n/a | NM_001001928 |
| uc062fxf.1 | n/a | n/a | NR_111920 |
| uc062hvi.1 | n/a | n/a | NR_046352 |
| uc062jao.1 | n/a | n/a | NR_033815 |
| uc062jap.1 | n/a | n/a | NR_033815 |
| uc062jaq.1 | n/a | n/a | NR_033815 |
| uc062jar.1 | n/a | n/a | NR_033815 |
| uc062jbi.1 | n/a | n/a | NR_102269 |
| uc062kuu.1 | n/a | n/a | NR_024460 |
| uc062lut.1 | n/a | n/a | NM_001261829 |
| uc062ozu.1 | n/a | n/a | NM_001303264 |
| uc062qnh.1 | n/a | n/a | NR_120639 |
| uc062rsf.1 | n/a | n/a | NR_003265 |
| uc062sjd.1 | n/a | n/a | NR_003265 |
| uc062tkr.1 | n/a | n/a | NR_003265 |
| uc062xko.1 | n/a | n/a | NM_001288984 |
| uc062xlo.1 | n/a | n/a | NR_103781 |
| uc062xlr.1 | n/a | n/a | NR_103782 |
| uc063djw.1 | n/a | n/a | NR_073113 |
| uc063dpc.1 | n/a | n/a | NR_104662 |
| uc063exq.1 | n/a | n/a | NM_001174071 |
| uc063fxo.1 | n/a | n/a | NM_001303250 |
| uc063jxj.1 | n/a | n/a | NR_036494 |
| uc063jys.1 | n/a | n/a | NR_045724 |
| uc063kor.1 | n/a | n/a | NR_131066 |
| uc063lje.1 | n/a | n/a | NM_001195286 |
| uc063ljh.1 | n/a | n/a | NM_001195286 |
| uc063msm.1 | n/a | n/a | NR_072994 |
| uc063okh.1 | n/a | n/a | NR_126417 |
| uc063twf.1 | n/a | n/a | NR_072994 |
| uc063vcd.1 | n/a | n/a | NR_072994 |
| uc063whs.1 | n/a | n/a | NR_072994 |
| uc063xhb.1 | n/a | n/a | NR_072994 |
| uc063ymx.1 | n/a | n/a | NR_072994 |
| uc063zss.1 | n/a | n/a | NR_072994 |
| uc064dvi.1 | n/a | n/a | NR_047689 |
| uc064efz.1 | n/a | n/a | NR_045512 |

TABLE 9-continued

| GeneName | Symbol | Description | RefSeq |
|---|---|---|---|
| uc064egh.1 | n/a | n/a | NR_045512 |
| uc064hve.1 | n/a | n/a | NM_001282788 |
| uc064jzg.1 | n/a | n/a | NR_125425 |
| uc064ooz.1 | n/a | n/a | NR_024522 |
| uc064pgy.1 | n/a | n/a | NR_126339 |
| uc064qlx.1 | n/a | n/a | NM_003033 |
| uc064rdj.1 | n/a | n/a | NR_110193 |
| uc064snu.1 | n/a | n/a | NR_036576 |
| uc064sny.1 | n/a | n/a | NR_036577 |
| uc064soc.1 | n/a | n/a | NR_036577 |
| uc064sye.1 | n/a | n/a | NM_001301226 |
| uc064tdf.1 | n/a | n/a | NR_104612 |
| uc064voi.1 | n/a | n/a | NR_033234 |
| uc064wmj.1 | n/a | n/a | NM_001110303 |
| uc065ama.1 | n/a | n/a | NM_001142423 |
| uc059bwu.1 | NAA30 | N(alpha)-acetyltransferase 30, NatC catalytic subunit (NAA30), (NM_001011713) | NM_001011713 |
| uc002giz.4 | NAA38 | N(alpha)-acetyltransferase 38, NatC auxiliary subunit (NAA38), (NM_032356) | NM_032356 |
| uc058csl.1 | NAA40 | N(alpha)-acetyltransferase 40, NatD catalytic subunit (NAA40) var 1, (NM_024771) | NM_024771 |
| uc059qle.1 | NAGPA | N-acetylglucosamine-1-phosphodiester alpha-N-acetylglucosaminidase (NAGPA), (NM_016256) | NM_016256 |
| uc059orr.1 | NARFL | nuclear prelamin A recognition factor-like (NARFL) var 1, (NM_022493) | NM_022493 |
| uc064kqr.1 | NAT1 | N-acetyltransferase 1 (arylamine N-acetyltransferase) (NAT1) var 4, (NM_001160173) | NM_001160173 |
| uc064ohv.1 | NBN | nibrin (NBN), (NM_002485) | NM_002485 |
| uc057jyz.1 | NBPF15 | neuroblastoma breakpoint family, member 15 (NBPF15) var 2, (NM_173638) | NM_173638 |
| uc057jza.1 | NBPF15 | neuroblastoma breakpoint family, member 15 (NBPF15) var 2, (NM_173638) | NM_173638 |
| uc062jkq.1 | NCKIPSD | NCK interacting protein with SH3 domain (NCKIPSD) var 2, (NM_184231) | NM_184231 |
| uc063rds.1 | NCOA7 | nuclear receptor coactivator 7 (NCOA7) var 5, (NM_001199621) | NM_001199621 |
| uc059scz.1 | NDUFAB1 | NADH dehydrogenase (ubiquinone) 1, alpha/beta subcomplex, 1, 8 kDa (NDUFAB1), (NM_005003) | NM_005003 |
| uc064ipg.1 | NDUFB2 | NADH dehydrogenase (ubiquinone) 1 beta subcomplex, 2, 8 kDa (NDUFB2), (NM_004546) | NM_004546 |
| uc064qad.1 | NDUFB9 | NADH dehydrogenase (ubiquinone) 1 beta subcomplex, 9, 22 kDa (NDUFB9) var 1, (NM_005005) | NM_005005 |
| uc057mpx.1 | NDUFS2 | NADH dehydrogenase (ubiquinone) Fe-S protein 2, 49 kDa (NADH-coenzyme Q reductase) (NDUFS2) var | NM_004550 |
| uc061wgs.1 | NECAB3 | N-terminal EF-hand calcium binding protein 3 (NECAB3) var 1, (NM_031231) | NM_031231 |
| uc061wgy.1 | NECAB3 | N-terminal EF-hand calcium binding protein 3 (NECAB3) var 1, (NM_031231) | NM_031231 |
| uc059dmz.1 | NEK9 | NIMA-related kinase 9 (NEK9), (NM_033116) | NM_033116 |
| uc060anh.1 | NEURL4 | neuralized E3 ubiquitin protein ligase 4 (NEURL4) var 2, (NM_001005408) | NM_001005408 |
| uc060gtm.1 | NFE2L1 | nuclear factor, erythroid 2-like 1 (NFE2L1), (NM_003204) | NM_003204 |
| uc062yok.1 | NFKB1 | nuclear factor of kappa light polypeptide gene enhancer in B-cells 1 (NFKB1) var 1, (NM_003998) | NM_003998 |
| uc060eaq.1 | NLE1 | notchless homolog 1 (*Drosophila*) (NLE1) var 2, (NM_001014445) | NM_001014445 |
| uc061end.1 | NLRP2, | NLR family, pyrin domain containing 2 (NLRP2) var 2, (NM_001174081), | NM_001174081 |
| uc061ctz.1 | NLRP7, | NLR family, pyrin domain containing 7 (NLRP7) var 3, (NM_001127255), | NM_001127255 |
| uc061foc.1 | NLRP7, | NLR family, pyrin domain containing 7 (NLRP7) var 3, (NM_001127255), | NM_001127255 |
| uc063dkf.1 | NNT | nicotinamide nucleotide transhydrogenase (NNT) var 2, (NM_182977) | NM_182977 |
| uc003naz.4 | NOL7 | nucleolar protein 7, 27 kDa (NOL7), (NM_016167) | NM_016167 |
| uc061var.1 | NOP56 | NOP56 ribonucleoprotein (NOP56) var 1, (NM_006392) | NM_006392 |
| uc061rnb.1 | NOP58 | NOP58 ribonucleoprotein (NOP58), (NM_015934) | NM_015934 |
| uc032awd.2 | NOP9 | NOP9 nucleolar protein (NOP9) var 2, (NM_001286367) | NM_001286367 |
| uc061mjc.1 | NPAS2 | neuronal PAS domain protein 2 (NPAS2), (NM_002518) | NM_002518 |
| uc058rvs.1 | NR2C1 | nuclear receptor subfamily 2, group C, member 1 (NR2C1) var 1, (NM_003297) | NM_003297 |
| uc058rvy.1 | NR2C1 | nuclear receptor subfamily 2, group C, member 1 (NR2C1) var 2, (NM_001032287) | NM_001032287 |
| uc058cye.1 | NRXN2 | neurexin 2 (NRXN2) var beta, (NM_138734) | NM_138734 |
| uc059six.1 | NSMCE1 | non-SMC element 1 homolog (S. cerevisiae) (NSMCE1), (NM_145080) | NM_145080 |
| uc021txo.2 | NT5C3B | 5'-nucleotidase, cytosolic IIIB (NT5C3B) var 1, (NM_052935) | NM_052935 |
| uc060fdr.1 | NT5C3B | 5'-nucleotidase, cytosolic IIIB (NT5C3B) var 1, (NM_052935) | NM_052935 |
| uc060fdx.1 | INT5C3B | 5'-nucleotidase, cytosolic IIIB (NT5C3B) var 1, (NM_052935) | NM_052935 |
| uc061aza.1 | NTF4 | neurotrophin 4 (NTF4), (NM_006179) | NM_006179 |
| uc058qqv.1 | NUP107 | nucleoporin 107 kDa (NUP107), (NM_020401) | NM_020401 |
| uc061bmx.1 | NUP62 | nucleoporin 62 kDa (NUP62) var 1, (NM_153719) | NM_153719 |
| uc060jui.1 | NUP85 | nucleoporin 85 kDa (NUP85) var 1, (NM_024844) | NM_024844 |
| uc002gbo.3 | NUP88 | nucleoporin 88 kDa (NUP88), (NM_002532) | NM_002532 |
| uc057qef.1 | OBSCN | obscurin, cytoskeletal calmodulin and titin-interacting RhoGEF (OBSCN) var IC, (NM_001271223) | NM_001271223 |
| uc057qeh.1 | OBSCN | obscurin, cytoskeletal calmodulin and titin-interacting RhoGEF (OBSCN) var IC, (NM_001271223) | NM_001271223 |
| uc011mbf.3 | ODF2 | outer dense fiber of sperm tails 2 (ODF2) var 7, (NM_153440) | NM_153440 |
| uc003qpt.3 | OPRM1 | opioid receptor, mu 1 (OPRM1) var MOR-10, (NM_001008503) | NM_001008503 |
| uc063skb.1 | OPRM1 | opioid receptor, mu 1 (OPRM1) var MOR-10, (NM_001008503) | NM_001008503 |
| uc058eqx.1 | ORAOV1 | oral cancer overexpressed 1 (ORAOV1), (NM_153451) | NM_153451 |
| uc057fbq.1 | PABPC4 | poly(A) binding protein, cytoplasmic 4 (inducible form) (PABPC4) var 3, (NM_001135654) | NM_001135654 |
| uc010nba.2 | PAEP | progestagen-associated endometrial protein (PAEP) var 1, (NM_001018049) | NM_001018049 |
| uc059sdf.1 | PALB2 | partner and localizer of BRCA2 (PALB2), (NM_024675) | NM_024675 |
| uc059rap.1 | PARN, | poly(A)-specific ribonuclease (PARN) var 3, (NM_001242992), | NM_001242992 |
| uc063dll.1 | PARP8 | poly (ADP-ribose) polymerase family, member 8 (PARP8) var 1, (NM_001178055) | NM_001178055 |
| uc003aks.4 | PATZ1 | POZ (BTB) and AT hook containing zinc finger 1 (PATZ1) var 4, (NM_032051) | NM_032051 |
| uc010mls.3 | PAX5 | paired box 5 (PAX5) var 5, (NM_001280550) | NM_001280550 |
| uc064kpk.1 | PCM1 | pericentriolar material 1 (PCM1), (NM_006197) | NM_006197 |
| uc062mbe.1 | PCNP | PEST proteolytic signal containing nuclear protein (PCNP), (NM_020357) | NM_020357 |
| uc060wvu.1 | PDCD2L | programmed cell death 2-like (PDCD2L), (NM_032346) | NM_032346 |
| uc057xls.1 | PDDC1 | Parkinson disease 7 domain containing 1 (PDDC1), (NM_182612) | NM_182612 |

TABLE 9-continued

| GeneName | Symbol | Description | RefSeq |
|---|---|---|---|
| uc058fbw.1 | PDE2A | phosphodiesterase 2A, cGMP-stimulated (PDE2A) var 2, (NM_001143839) | NM_001143839 |
| uc001emb.3 | PDE4DIP | phosphodiesterase 4D interacting protein (PDE4DIP) var 5, (NM_001002811) | NM_001002811 |
| uc062zgs.1 | PDE5A | phosphodiesterase 5A, cGMP-specific (PDE5A) var 3, (NM_033437) | NM_033437 |
| uc062alz.1 | PDE9A | phosphodiesterase 9A (PDE9A) var 2, (NM_001001567) | NM_001001567 |
| uc059rcs.1 | PDXDC1, | pyridoxal-dependent decarboxylase domain containing 1 (PDXDC1) var 1, (NM_015027), | NM_015027 |
| uc060baa.1 | PFAS | phosphoribosylformylglycinamidine synthase (PFAS), (NM_012393) | NM_012393 |
| uc062zmx.1 | PGRMC2 | progesterone receptor membrane component 2 (PGRMC2), (NM_006320) | NM_006320 |
| uc058kyj.1 | PHC1 | polyhomeotic homolog 1 (Drosophila) (PHC1), (NM_004426) | NM_004426 |
| uc057jvt.1 | PHGDH | phosphoglycerate dehydrogenase (PHGDH), (NM_006623) | NM_006623 |
| uc003try.3 | PHKG1 | phosphorylase kinase, gamma 1 (muscle) (PHKG1) var 2, (NM_006213) | NM_006213 |
| uc064kza.1 | PHYHIP | phytanoyl-CoA 2-hydroxylase interacting protein (PHYHIP) var 2, (NM_014759) | NM_014759 |
| uc021yzd.2 | PI16 | peptidase inhibitor 16 (PI16) var 2, (NM_001199159) | NM_001199159 |
| uc057xni.1 | PIDD1 | p53-induced death domain protein 1 (PIDD1) var 3, (NM_145887) | NM_145887 |
| uc057xnk.1 | PIDD1 | p53-induced death domain protein 1 (PIDD1) var 3, (NM_145887) | NM_145887 |
| uc061iwd.1 | PIGF | phosphatidylinositol glycan anchor biosynthesis, class F (PIGF) var 1, (NM_002643) | NM_002643 |
| uc064kfe.1 | PINX1 | PIN2/TERF1 interacting, telomerase inhibitor 1 (PINX1) var 2, (NM_001284356) | NM_001284356 |
| uc059php.1 | PKD1 | polycystic kidney disease 1 (autosomal dominant) (PKD1) var 2, (NM_000296) | NM_000296 |
| uc059phr.1 | PKD1 | polycystic kidney disease 1 (autosomal dominant) (PKD1) var 2, (NM_000296) | NM_000296 |
| uc059phu.1 | PKD1 | polycystic kidney disease 1 (autosomal dominant) (PKD1) var 2, (NM_000296) | NM_000296 |
| uc062mvd.1 | PLA1A | phospholipase A1 member A (PLA1A) var 3, (NM_001206961) | NM_001206961 |
| uc059rbn.1 | PLA2G10, | phospholipase A2, group X (PLA2G10), (NM_003561), | NM_003561 |
| uc062eed.1 | PLA2G6 | phospholipase A2, group VI (cytosolic, calcium-independent) (PLA2G6) var 2, (NM_001004426) | NM_001004426 |
| uc009ypi.4 | PLCB3 | phospholipase C, beta 3 (phosphatidylinositol-specific) (PLCB3) var 1, (NM_000932) | NM_000932 |
| uc062iet.1 | PLCD1 | phospholipase C, delta 1 (PLCD1) var 2, (NM_006225) | NM_006225 |
| uc061xac.1 | PLCG1 | phospholipase C, gamma 1 (PLCG1) var 2, (NM_182811) | NM_182811 |
| uc061xai.1 | PLCG1 | phospholipase C, gamma 1 (PLCG1) var 2, (NM_182811) | NM_182811 |
| uc064mek.1 | PLEKHA2 | pleckstrin homology domain containing, family A (phosphoinositide binding specific) member 2 (PLEKHA2), (NM_021623) | NM_021623 |
| uc059vsr.1 | PLEKHG4 | pleckstrin homology domain containing, family G (with RhoGef domain) member 4 (PLEKHG4) var 4, (NM_001129729) | NM_001129729 |
| uc063dul.1 | PLK2 | polo-like kinase 2 (PLK2) var 2, (NM_001252226) | NM_001252226 |
| uc058per.1 | PMEL | premelanosome protein (PMEL) var 3, (NM_006928) | NM_006928 |
| uc062erg.1 | PMM1 | phosphomannomutase 1 (PMM1), (NM_002676) | NM_002676 |
| uc064bfu.1 | PMS2 | PMS2 postmeiotic segregation increased 2 (S. cerevisiae) (PMS2) var 1, (NM_000535) | NM_000535 |
| uc060grk.1 | PNPO | pyridoxamine 5'-phosphate oxidase (PNPO), (NM_018129) | NM_018129 |
| uc061jis.1 | PNPT1 | polyribonucleotide nucleotidyltransferase 1 (PNPT1), (NM_033109) | NM_033109 |
| uc062avx.1 | POFUT2 | protein O-fucosyltransferase 2 (POFUT2) var 3, (NM_133635) | NM_133635 |
| uc062mui.1 | POGLUT1 | protein O-glucosyltransferase 1 (POGLUT1) var 1, (NM_152305) | NM_152305 |
| uc062uom.1 | POLN | polymerase (DNA directed) nu (POLN), (NM_181808) | NM_181808 |
| uc057kca.1 | POLR3GL | polymerase (RNA) III (DNA directed) polypeptide G (32 kD)-like (POLR3GL), (NM_032305) | NM_032305 |
| uc003baf.5 | POLR3H | polymerase (RNA) III (DNA directed) polypeptide H (22.9 kD) (POLR3H) var 1, (NM_138338) | NM_138338 |
| uc062eqw.1 | POLR3H | polymerase (RNA) III (DNA directed) polypeptide H (22.9 kD) (POLR3H) var 3, (NM_001018050) | NM_001018050 |
| uc060qpo.1 | POLRMT | polymerase (RNA) mitochondrial (DNA directed) (POLRMT), (NM_005035) | NM_005035 |
| uc064emi.1 | POM121C | POM121 transmembrane nucleoporin C (POM121C), (NM_001099415) | NM_001099415 |
| uc057tvj.1 | PPA1 | pyrophosphatase (inorganic) 1 (PPA1), (NM_021129) | NM_021129 |
| uc061isf.1 | PPM1B | protein phosphatase, Mg2+/Mn2+ dependent, 1B (PPM1B) var 1, (NM_002706) | NM_002706 |
| uc001oux.4 | PPME1 | protein phosphatase methylesterase 1 (PPME1) var 1, (NM_016147) | NM_016147 |
| uc061hsv.1 | PPP1CB | protein phosphatase 1, catalytic subunit, beta isozyme (PPP1CB) var 3, (NM_206876) | NM_206876 |
| uc058tfv.1 | PPP1CC | protein phosphatase 1, catalytic subunit, gamma isozyme (PPP1CC) var 1, (NM_002710) | NM_002710 |
| uc058zqd.1 | PPP1R3E | protein phosphatase 1, regulatory subunit 3E (PPP1R3E), (NM_001276318) | NM_001276318 |
| uc058zqh.1 | PPP1R3E | protein phosphatase 1, regulatory subunit 3E (PPP1R3E), (NM_001276318) | NM_001276318 |
| uc058hey.1 | PPP2R1B | protein phosphatase 2, regulatory subunit A, beta (PPP2R1B) var 3, (NM_181700) | NM_181700 |
| uc058enj.1 | PPP6R3 | protein phosphatase 6, regulatory subunit 3 (PPP6R3) var 3, (NM_001164164) | NM_001164164 |
| uc058enm.1 | PPP6R3 | protein phosphatase 6, regulatory subunit 3 (PPP6R3) var 3, (NM_001164164) | NM_001164164 |
| uc057ckh.1 | PRAMEF11 | PRAME family member 11 (PRAMEF11), (NM_001146344) | NM_001146344 |
| uc064yij.1 | PRDX4 | peroxiredoxin 4 (PRDX4), (NM_006406) | NM_006406 |
| uc063phe.1 | PRIM2 | primase, DNA, polypeptide 2 (58 kDa) (PRIM2) var 1, (NM_000947) | NM_000947 |
| uc010smd.3 | PRKAG1 | protein kinase, AMP-activated, gamma 1 non-catalytic subunit (PRKAG1) var 4, (NM_001206710) | NM_001206710 |
| uc060ttb.1 | PRKCSH | protein kinase C substrate 80K-H (PRKCSH) var 1, (NM_002743) | NM_002743 |
| uc010vlg.3 | PRMT7 | protein arginine methyltransferase 7 (PRMT7) var 2, (NM_001184824) | NM_001184824 |
| uc059wfl.1 | PRMT7 | protein arginine methyltransferase 7 (PRMT7) var 2, (NM_001184824) | NM_001184824 |
| uc059wfq.1 | PRMT7 | protein arginine methyltransferase 7 (PRMT7) var 1, (NM_019023) | NM_019023 |
| uc059wfw.1 | PRMT7 | protein arginine methyltransferase 7 (PRMT7) var 1, (NM_019023) | NM_019023 |
| uc057knz.1 | PRPF3 | pre-mRNA processing factor 3 (PRPF3), (NM_004698) | NM_004698 |
| uc059zhu.1 | PRPF8, | pre-mRNA processing factor 8 (PRPF8), (NM_006445), | NM_006445 |
| uc064wqo.1 | PRRC2B | proline-rich coiled-coil 2B (PRRC2B), (NM_013318) | NM_013318 |
| uc064wqp.1 | PRRC2B | proline-rich coiled-coil 2B (PRRC2B), (NM_013318) | NM_013318 |
| uc057nga.1 | PRRX1 | paired related homeobox 1 (PRRX1) var pmx-1b, (NM_022716) | NM_022716 |
| uc003njc.2 | PRSS16 | protease, serine, 16 (thymus) (PRSS16), (NM_005865) | NM_005865 |
| uc060irr.1 | PSMC5 | proteasome (prosome, macropain) 26S subunit, ATPase, 5 (PSMC5) var 1, (NM_002805) | NM_002805 |
| uc063mxz.1 | PSORS1C1, | psoriasis susceptibility 1 candidate 1 (PSORS1C1), (NM_014068), | NM_014068 |
| uc060qrc.1 | PTBP1 | polypyrimidine tract binding protein 1 (PTBP1) var 2, (NM_031990) | NM_031990 |
| uc060qrh.1 | PTBP1 | polypyrimidine tract binding protein 1 (PTBP1) var 1, (NM_002819) | NM_002819 |
| uc064ftl.1 | PTCD1 | pentatricopeptide repeat domain 1 (PTCD1), (NM_015545) | NM_015545 |
| uc064umt.1 | PTCH1 | patched 1 (PTCH1) var 1d, (NM_001083606) | NM_001083606 |
| uc064unb.1 | PTCH1 | patched 1 (PTCH1) var 1c', (NM_001083605) | NM_001083605 |
| uc061tni.1 | PTMA | prothymosin, alpha (PTMA) var 2, (NM_002823) | NM_002823 |

TABLE 9-continued

| GeneName | Symbol | Description | RefSeq |
|---|---|---|---|
| uc059kju.1 | PTPLAD1 | 3-hydroxyacyl-CoA dehydratase 3 (HACD3), (NM_016395) | NM_016395 |
| uc057olm.1 | PTPN7 | protein tyrosine phosphatase, non-receptor type 7 (PTPN7) var 1, (NM_002832) | NM_002832 |
| uc057ebo.1 | PTPRU | protein tyrosine phosphatase, receptor type, U (PTPRU) var 4, (NM_001195001) | NM_001195001 |
| uc058mvt.1 | PUS7L | pseudouridylate synthase 7 homolog (S. cerevisiae)-like (PUS7L) var 2, (NM_001098614) | NM_001098614 |
| uc062aqk.1 | PWP2 | PWP2 periodic tryptophan protein homolog (yeast) (PWP2), (NM_005049) | NM_005049 |
| uc061gcj.1 | PXDN | peroxidasin (PXDN), (NM_012293) | NM_012293 |
| uc061gcl.1 | PXDN | peroxidasin (PXDN), (NM_012293) | NM_012293 |
| uc058fzr.1 | RAB30 | RAB30, member RAS oncogene family (RAB30) var 2, (NM_014488) | NM_014488 |
| uc059cse.1 | RAD51B | RAD51 paralog B (RAD51B) var 2, (NM_133510) | NM_133510 |
| uc060sfo.1 | RANBP3 | RAN binding protein 3 (RANBP3) var 4, (NM_001300865) | NM_001300865 |
| uc058nbm.1 | RAPGEF3 | Rap guanine nucleotide exchange factor (GEF) 3 (RAPGEF3) var 2, (NM_006105) | NM_006105 |
| uc001scd.4 | RARG | retinoic acid receptor, gamma (RARG) var 2, (NM_001042728) | NM_001042728 |
| uc060uuc.1 | RASAL3 | RAS protein activator like 3 (RASAL3), (NM_022904) | NM_022904 |
| uc057emf.1 | RBBP4 | retinoblastoma binding protein 4 (RBBP4) var 3, (NM_001135256) | NM_001135256 |
| uc004dhf.4 | RBM10 | RNA binding motif protein 10 (RBM10) var 1, (NM_005676) | NM_005676 |
| uc004dhi.4 | RBM10 | RNA binding motif protein 10 (RBM10) var 5, (NM_001204468) | NM_001204468 |
| uc001tvn.5 | RBM19 | RNA binding motif protein 19 (RBM19) var 3, (NM_001146698) | NM_001146698 |
| uc063iia.1 | RBM27 | RNA binding motif protein 27 (RBM27), (NM_018989) | NM_018989 |
| uc057kbj.1 | RBM8A | RNA binding motif protein 8A (RBM8A), (NM_005105) | NM_005105 |
| uc058acp.1 | RCN1 | reticulocalbin 1, EF-hand calcium binding domain (RCN1), (NM_002901) | NM_002901 |
| uc010ffx.2 | REG1A | regenerating islet-derived 1 alpha (REG1A), (NM_002909) | NM_002909 |
| uc062vzw.1 | RFC1 | replication factor C (activator 1) 1, 145 kDa (RFC1) var 1, (NM_002913) | NM_002913 |
| uc059xcn.1 | RFWD3 | ring finger and WD repeat domain 3 (RFWD3), (NM_018124) | NM_018124 |
| uc032tgs.1 | RHOH | ras homolog family member H (RHOH) var 4, (NM_001278362) | NM_001278362 |
| uc032tgt.1 | RHOH | ras homolog family member H (RHOH) var 1, (NM_001278359) | NM_001278359 |
| uc032tgu.1 | RHOH | ras homolog family member H (RHOH) var 3, (NM_001278361) | NM_001278361 |
| uc032tgv.1 | RHOH | ras homolog family member H (RHOH) var 2, (NM_001278360) | NM_001278360 |
| uc062wcw.1 | RHOH | ras homolog family member H (RHOH) var 4, (NM_001278362) | NM_001278362 |
| uc064guf.1 | RINT1 | RAD50 interactor 1 (RINT1), (NM_021930) | NM_021930 |
| uc009yst.4 | RNF121 | ring finger protein 121 (RNF121) var 4, (NM_001300926) | NM_001300926 |
| uc057xhm.1 | RNH1 | ribonuclease/angiogenin inhibitor 1 (RNH1) var 6, (NM_203387) | NM_203387 |
| uc060nrm.1 | RNMT | RNA (guanine-7-) methyltransferase (RNMT) var 2, (NM_003799) | NM_003799 |
| uc064qmg.1 | RP11-157E21.1 | uncharacterized LOC101927822 (LOC101927822), long non-coding RNA. (NR_125424) | NR_125424 |
| uc059ugi.1 | RPGRIP1L | RPGRIP1-like (RPGRIP1L) var 2, (NM_001127897) | NM_001127897 |
| uc059scp.1 | RPL36 | ribosomal protein L36 (RPL36) var 1, (NM_033643) | NM_033643 |
| uc058cxm.1 | RPS6KA4 | ribosomal protein S6 kinase, 90 kDa, polypeptide 4 (RPS6KA4) var 3, (NM_001300802) | NM_001300802 |
| uc059dli.1 | RPS6KL1 | ribosomal protein S6 kinase-like 1 (RPS6KL1), (NM_031464) | NM_031464 |
| uc002jys.5 | RPTOR | regulatory associated protein of MTOR, complex 1 (RPTOR) var 2, (NM_001163034) | NM_001163034 |
| uc010wuf.2 | RPTOR | regulatory associated protein of MTOR, complex 1 (RPTOR) var 2, (NM_001163034) | NM_001163034 |
| uc003znj.4 | RRAGA | Ras-related GTP binding A (RRAGA), (NM_006570) | NM_006570 |
| uc001mlf.5 | RRAS2 | related RAS viral (r-ras) oncogene homolog 2 (RRAS2) var 1, (NM_012250) | NM_012250 |
| uc057vee.1 | RRP12 | ribosomal RNA processing 12 homolog (S. cerevisiae) (RRP12) var 3, (NM_001284337) | NM_001284337 |
| uc003xwa.3 | RRS1 | RRS1 ribosome biogenesis regulator homolog (S. cerevisiae) (RRS1), (NM_015169) | NM_015169 |
| uc060hiq.1 | RSAD1 | radical S-adenosyl methionine domain containing 1 (RSAD1) var 1, (NM_018346) | NM_018346 |
| uc064okw.1 | RUNX1T1 | runt-related transcription factor 1; translocated to, 1 (cyclin D-related) (RUNX1T1) var 3, (NM_175635) | NM_175635 |
| uc062oaq.1 | RYK | receptor-like tyrosine kinase (RYK) var 2, (NM_002958) | NM_002958 |
| uc060yct.1 | RYR1 | ryanodine receptor 1 (skeletal) (RYR1) var 2, (NM_001042723) | NM_001042723 |
| uc001fbv.2 | S100A7 | S100 calcium binding protein A7 (S100A7), (NM_002963) | NM_002963 |
| uc061akp.1 | SAE1 | SUMO1 activating enzyme subunit 1 (SAE1) var 1, (NM_005500) | NM_005500 |
| uc061yqp.1 | SAMD10 | sterile alpha motif domain containing 10 (SAMD10), (NM_080621) | NM_080621 |
| uc064psr.1 | SAMD12 | sterile alpha motif domain containing 12 (SAMD12) var 2, (NM_207506) | NM_207506 |
| uc060yhx.1 | SARS2 | seryl-tRNA synthetase 2, mitochondrial (SARS2) var 2, (NM_017827) | NM_017827 |
| uc010swx.2 | SART3 | squamous cell carcinoma antigen recognized by T cells 3 (SART3), (NM_014706) | NM_014706 |
| uc058suo.1 | SART3 | squamous cell carcinoma antigen recognized by T cells 3 (SART3), (NM_014706) | NM_014706 |
| uc001pxu.4 | SC5D | sterol-C5-desaturase (SC5D) var 1, (NM_006918) | NM_006918 |
| uc064bpk.1 | SCIN | scinderin (SCIN) var 2, (NM_033128) | NM_033128 |
| uc062iho.1 | SCN5A | sodium channel, voltage gated, type V alpha subunit (SCN5A) var 6, (NM_001160161) | NM_001160161 |
| uc057gqh.1 | SCP2 | sterol carrier protein 2 (SCP2) var 1, (NM_002979) | NM_002979 |
| uc062xkn.1 | SDAD1 | SDA1 domain containing 1 (SDAD1) var 1, (NM_018115) | NM_018115 |
| uc059ahe.1 | SDR39U1 | short chain dehydrogenase/reductase family 39U, member 1 (SDR39U1) var 1, (NM_020195) | NM_020195 |
| uc059xqn.1 | SDR42E1 | short chain dehydrogenase/reductase family 42E, member 1 (SDR42E1), (NM_145168) | NM_145168 |
| uc062dcv.1 | SEC14L2 | SEC14-like 2 (S. cerevisiae) (SEC14L2) var 2, (NM_033382) | NM_033382 |
| uc061vqr.1 | SEC23B | Sec23 homolog B (S. cerevisiae) (SEC23B) var 4, (NM_001172745) | NM_001172745 |
| uc060npf.1 | SEH1L | SEH1-like (S. cerevisiae) (SEH1L) var 1, (NM_001013437) | NM_001013437 |
| uc057rtz.1 | SEPHS1 | selenophosphate synthetase 1 (SEPHS1) var 2, (NM_001195602) | NM_001195602 |
| uc057nku.1 | SERPINC1 | serpin peptidase inhibitor, clade C (antithrombin), member 1 (SERPINC1), (NM_000488) | NM_000488 |
| uc062bvk.1 | SERPIND1 | serpin peptidase inhibitor, clade D (heparin cofactor), member 1 (SERPIND1), (NM_000185) | NM_000185 |
| uc058fon.1 | SERPINH1 | serpin peptidase inhibitor, clade H (heat shock protein 47), member 1, (collagen binding protein 1) (SERPINH1) var1, (NM_001207014) | NM_001207014 |
| uc058czs.1 | SF1 | splicing factor 1 (SF1) var 5, (NM_001178031) | NM_001178031 |
| uc003alf.5 | SFI1 | Sfi1 homolog, spindle assembly associated (yeast) (SFI1) var 2, (NM_014775) | NM_014775 |
| uc062djn.1 | SFI1 | Sfi1 homolog, spindle assembly associated (yeast) (SFI1) var 1, (NM_001007467) | NM_001007467 |
| uc062djs.1 | SFI1 | Sfi1 homolog, spindle assembly associated (yeast) (SFI1) var 2, (NM_014775) | NM_014775 |
| uc061kon.1 | SFXN5 | sideroflexin 5 (SFXN5), (NM_144579) | NM_144579 |
| uc061koq.1 | SFXN5 | sideroflexin 5 (SFXN5), (NM_144579) | NM_144579 |
| uc058hsd.1 | SIDT2 | SID1 transmembrane family, member 2 (SIDT2), (NM_001040455) | NM_001040455 |
| uc062anz.1 | SIK1 | salt-inducible kinase 1 (SIK1), (NM_173354) | NM_173354 |

TABLE 9-continued

| GeneName | Symbol | Description | RefSeq |
|---|---|---|---|
| uc001zwn.5 | SLC12A1 | solute carrier family 12 (sodium/potassium/chloride transporter), member 1 (SLC12A1) var 1, (NM_000338) | NM_000338 |
| uc001zwr.5 | SLC12A1 | solute carrier family 12 (sodium/potassium/chloride transporter), member 1 (SLC12A1) var 1, (NM_000338) | NM_000338 |
| uc010bem.4 | SLC12A1 | solute carrier family 12 (sodium/potassium/chloride transporter), member 1 (SLC12A1) var 2, (NM_001184832) | NM_001184832 |
| uc059wbp.1 | SLC12A4 | solute carrier family 12 (potassium/chloride transporter), member 4 (SLC12A4) var 5, (NM_001145964) | NM_001145964 |
| uc060aff.1 | SLC13A5 | solute carrier family 13 (sodium-dependent citrate transporter), member 5 (SLC13A5) var 2, (NM_001143838) | NM_001143838 |
| uc058qfi.1 | SLC16A7 | solute carrier family 16 (monocarboxylate transporter), member 7 (SLC16A7) var 3, (NM_004731) | NM_004731 |
| uc061pqs.1 | SLC25A12 | solute carrier family 25 (aspartate/glutamate carrier), member 12 (SLC25A12) var 1, (NM_003705) | NM_003705 |
| uc064wao.1 | SLC25A25 | solute carrier family 25 (mitochondrial carrier; phosphate carrier), member 25 (SLC25A25) var 1, (NM_052901) | NM_052901 |
| uc002gku.1 | SLC25A35 | solute carrier family 25, member 35 (SLC25A35), (NM_201520) | NM_201520 |
| uc003etr.3 | SLC25A36 | solute carrier family 25 (pyrimidine nucleotide carrier), member 36 (SLC25A36) var 1, (NM_001104647) | NM_001104647 |
| uc062okh.1 | SLC25A36 | solute carrier family 25 (pyrimidine nucleotide carrier), member 36 (SLC25A36) var 2, (NM_018155) | NM_018155 |
| uc060fzi.1 | SLC25A39 | solute carrier family 25, member 39 (SLC25A39) var 1, (NM_001143780) | NM_001143780 |
| uc057lww.1 | SLC25A44 | solute carrier family 25, member 44 (SLC25A44) var 2, (NM_014655) | NM_014655 |
| uc062chx.1 | SLC2A11, | solute carrier family 2 (facilitated glucose transporter), member 11 (SLC2A11) var 2, (NM_001024939) | NM_001024939 |
| uc062fuv.1 | SLC2A11, | solute carrier family 2 (facilitated glucose transporter), member 11 (SLC2A11) var 2, (NM_001024939), | NM_001024939 |
| uc001rpe.5 | SLC38A1 | solute carrier family 38, member 1 (SLC38A1) var 4, (NM_001278388) | NM_001278388 |
| uc062kbt.1 | SLC38A3 | solute carrier family 38, member 3 (SLC38A3), (NM_006841) | NM_006841 |
| uc063hum.1 | SLC4A9 | solute carrier family 4, sodium bicarbonate cotransporter, member 9 (SLC4A9) var 4, (NM_001258427) | NM_001258427 |
| uc062dml.1 | SLC5A1 | solute carrier family 5 (sodium/glucose cotransporter), member 1 (SLC5A1) var 2, (NM_001256314) | NM_001256314 |
| uc002gur.3 | SLC5A10 | solute carrier family 5 (sodium/sugar cotransporter), member 10 (SLC5A10) var 5, (NM_001282417) | NM_001282417 |
| uc062iym.1 | SLC6A20 | solute carrier family 6 (proline IMINO transporter), member 20 (SLC6A20) var 2, (NM_022405) | NM_022405 |
| uc059kor.1 | SMAD3 | SMAD family member 3 (SMAD3) var 3, (NM_001145103) | NM_001145103 |
| uc033eer.2 | SMC1A | structural maintenance of chromosomes 1A (SMC1A) var 1, (NM_006306) | NM_006306 |
| uc064zkv.1 | SMC1A | structural maintenance of chromosomes 1A (SMC1A) var 2, (NM_001281463) | NM_001281463 |
| uc002cxt.4 | SMIM22 | small integral membrane protein 22 (SMIM22) var 2, (NM_001253791) | NM_001253791 |
| uc059qjk.1 | SMIM22 | small integral membrane protein 22 (SMIM22) var 3, (NM_001253793) | NM_001253793 |
| uc061ver.1 | SMOX | spermine oxidase (SMOX) var 2, (NM_175840) | NM_175840 |
| uc001sff.3 | SMUG1 | single-strand-selective monofunctional uracil-DNA glycosylase 1 (SMUG1) var 1, (NM_014311) | NM_014311 |
| uc058ouu.1 | SMUG1 | single-strand-selective monofunctional uracil-DNA glycosylase 1 (SMUG1) var 1, (NM_014311) | NM_014311 |
| uc057qye.1 | SMYD3 | SET and MYND domain containing 3 (SMYD3) var 2, (NM_022743) | NM_022743 |
| uc064hsr.1 | SND1 | staphylococcal nuclease and tudor domain containing 1 (SND1), (NM_014390) | NM_014390 |
| uc064hsz.1 | SND1 | staphylococcal nuclease and tudor domain containing 1 (SND1), (NM_014390) | NM_014390 |
| uc001tfu.2 | SNORA53 | small nucleolar RNA, H/ACA box 53 (SNORA53), small nucleolar RNA. (NR_003015) | NR_003015 |
| uc058rza.1 | SNRPF | small nuclear ribonucleoprotein polypeptide F (SNRPF), (NM_003095) | NM_003095 |
| uc061gbe.1 | SNTG2, | syntrophin, gamma 2 (SNTG2), (NM_018968), | NM_018968 |
| uc061gbj.1 | SNTG2, | syntrophin, gamma 2 (SNTG2), (NM_018968), | NM_018968 |
| uc002dby.6 | SNX29 | sorting nexin 29 (SNX29), (NM_032167) | NM_032167 |
| uc064pbh.1 | SNX31 | sorting nexin 31 (SNX31), (NM_152628) | NM_152628 |
| uc064kzy.1 | SORBS3 | sorbin and SH3 domain containing 3 (SORBS3) var 1, (NM_005775) | NM_005775 |
| uc060jjo.1 | SOX9-AS1 | SOX9 antisense RNA 1 (SOX9-AS1) var 1, long non-coding RNA. (NR_103738) | NR_103738 |
| uc064szm.1 | SPAG8 | sperm associated antigen 8 (SPAG8) var 1, (NM_001039592) | NM_001039592 |
| uc064tit.1 | SPATA31A7 | SPATA31 subfamily A, member 7 (SPATA31A7), (NM_015667) | NM_015667 |
| uc059yny.1 | SPG7 | spastic paraplegia 7 (pure and complicated autosomal recessive) (SPG7) var 1, (NM_003119) | NM_003119 |
| uc060kiw.1 | SPHK1 | sphingosine kinase 1 (SPHK1) var 3, (NM_001142601) | NM_001142601 |
| uc060xzg.1 | SPINT2 | serine peptidase inhibitor, Kunitz type, 2 (SPINT2) var a, (NM_021102) | NM_021102 |
| uc001qrl.4 | SPSB2 | splA/ryanodine receptor domain and SOCS box containing 2 (SPSB2) var 2, (NM_001146316) | NM_001146316 |
| uc001qrm.4 | SPSB2 | splA/ryanodine receptor domain and SOCS box containing 2 (SPSB2) var 1, (NM_032641) | NM_032641 |
| uc063eby.1 | SREK1 | splicing regulatory glutamine/lysine-rich protein 1 (SREK1) var 4, (NM_001270493) | NM_001270493 |
| uc059cvw.1 | SRSF5 | serine/arginine-rich splicing factor 5 (SRSF5) var 2, (NM_006925) | NM_006925 |
| uc002kvn.4 | SS18 | synovial sarcoma translocation, chromosome 18 (SS18) var 2, (NM_005637) | NM_005637 |
| uc060vqs.1 | SSBP4 | single stranded DNA binding protein 4 (SSBP4) var 2, (NM_001009998) | NM_001009998 |
| uc058mcg.1 | SSPN | sarcospan (SSPN) var 2, (NM_001135823) | NM_001135823 |
| uc064qdv.1 | ST3GAL1 | ST3 beta-galactoside alpha-2,3-sialyltransferase 1 (ST3GAL1) var 2, (NM_173344) | NM_173344 |
| uc061lkd.1 | ST3GAL5 | ST3 beta-galactoside alpha-2,3-sialyltransferase 5 (ST3GAL5) var 1, (NM_003896) | NM_003896 |
| uc057yug.1 | ST5 | suppression of tumorigenicity 5 (ST5) var 3, (NM_213618) | NM_213618 |
| uc010rnb.2 | STIP1 | stress-induced phosphoprotein 1 (STIP1) var 3, (NM_001282653) | NM_001282653 |
| uc061szr.1 | STK11IP | serine/threonine kinase 11 interacting protein (STK11IP), (NM_052902) | NM_052902 |
| uc003nyt.4 | STK19 | serine/threonine kinase 19 (STK19) var 3, non-coding RNA. (NR_026717) | NR_026717 |
| uc061uro.1 | STK25 | serine/threonine kinase 25 (STK25) var 4, (NM_006374) | NM_006374 |
| uc057jcy.1 | STRIP1 | striatin interacting protein 1 (STRIP1) var 2, (NM_001270768) | NM_001270768 |
| uc064egn.1 | STX1A | syntaxin 1A (brain) (STX1A) var 1, (NM_004603) | NM_004603 |
| uc064egv.1 | STX1A | syntaxin 1A (brain) (STX1A) var 2, (NM_001165903) | NM_001165903 |
| uc060vzi.1 | SUGP1 | SURP and G patch domain containing 1 (SUGP1), (NM_172231) | NM_172231 |
| uc060vzm.1 | SUGP1 | SURP and G patch domain containing 1 (SUGP1), (NM_172231) | NM_172231 |
| uc057yyi.1 | SWAP70 | SWAP switching B-cell complex 70 kDa subunit (SWAP70) var 1, (NM_015055) | NM_015055 |
| uc064pol.1 | SYBU | syntabulin (syntaxin-interacting) (SYBU) var 15, (NM_001099755) | NM_001099755 |

TABLE 9-continued

| GeneName | Symbol | Description | RefSeq |
|---|---|---|---|
| uc060urm.1 | SYDE1 | synapse defective 1, Rho GTPase, homolog 1 (*C. elegans*) (SYDE1) var 2, (NM_001300910) | NM_001300910 |
| uc059cwr.1 | SYNJ2BP | synaptojanin 2 binding protein (SYNJ2BP), (NM_018373) | NM_018373 |
| uc057crf.1 | SZRD1 | SUZ RNA binding domain containing 1 (SZRD1) var 3, (NM_001271869) | NM_001271869 |
| uc060eds.1 | TAF15, | TAF15 RNA polymerase II, TATA box binding protein (TBP)-associated factor, 68 kDa (TAF15) var 1, (NM_139215), | NM_139215 |
| uc002kvt.5 | TAF4B | TAF4b RNA polymerase II, TATA box binding protein (TBP)-associated factor, 105 kDa (TAF4B) var 1, (NM_001293725) | NM_001293725 |
| uc058cmy.1 | TAF6L | TAF6-like RNA polymerase II, p300/CBP-associated factor (PCAF)-associated factor, 65 kDa (TAF6L), (NM_006473) | NM_006473 |
| uc062vjo.1 | TAPT1 | transmembrane anterior posterior transformation 1 (TAPT1), (NM_153365) | NM_153365 |
| uc062dbn.1 | TBC1D10A | TBC1 domain family, member 10A (TBC1D10A) var 2, (NM_031937) | NM_031937 |
| uc063eum.1 | TBCA | tubulin folding cofactor A (TBCA) var 2, (NM_004607) | NM_004607 |
| uc064efg.1 | TBL2 | transducin (beta)-like 2 (TBL2), (NM_012453) | NM_012453 |
| uc059pdz.1 | TBL3 | transducin (beta)-like 3 (TBL3), (NM_006453) | NM_006453 |
| uc060rei.1 | TCF3 | transcription factor 3 (TCF3) var 2, (NM_001136139) | NM_001136139 |
| uc060rek.1 | TCF3 | transcription factor 3 (TCF3) var 1, (NM_003200) | NM_003200 |
| uc060rel.1 | TCF3 | transcription factor 3 (TCF3) var 1, (NM_003200) | NM_003200 |
| uc061znt.1 | TCP10L | t-complex 10-like (TCP10L), (NM_144659) | NM_144659 |
| uc001trp.6 | TCTN1 | tectonic family member 1 (TCTN1) var 3, (NM_024549) | NM_024549 |
| uc059efi.1 | TDP1 | tyrosyl-DNA phosphodiesterase 1 (TDP1) var 1, (NM_018319) | NM_018319 |
| uc059efp.1 | TDP1 | tyrosyl-DNA phosphodiesterase 1 (TDP1) var 1, (NM_018319) | NM_018319 |
| uc009wnb.2 | TDRKH | tudor and KH domain containing (TDRKH) var 3, (NM_006862) | NM_006862 |
| uc057kyy.1 | TDRKH | tudor and KH domain containing (TDRKH) var 2, (NM_001083963) | NM_001083963 |
| uc060upn.1 | TECR | trans-2,3-enoyl-CoA reductase (TECR) var 1, (NM_138501) | NM_138501 |
| uc058ozd.1 | TESPA1 | thymocyte expressed, positive selection associated 1 (TESPA1) var 3, (NM_014796) | NM_014796 |
| uc057wqu.1 | TEX36 | testis expressed 36 (TEX36), (NM_001128202) | NM_001128202 |
| uc061ojm.1 | TEX41 | testis expressed 41 (non-protein coding), long non-coding RNA. (NR_033870) | NR_033870 |
| uc057lnm.1 | THBS3 | thrombospondin 3 (THBS3) var 3, (NM_001252608) | NM_001252608 |
| uc021oyw.2 | THEM5 | thioesterase superfamily member 5 (THEM5), (NM_182578) | NM_182578 |
| uc060rmh.1 | THOP1 | thimet oligopeptidase 1 (THOP1), (NM_003249) | NM_003249 |
| uc021twy.2 | THRA | thyroid hormone receptor, alpha (THRA) var 4, (NM_001190919) | NM_001190919 |
| uc060ewp.1 | THRA | thyroid hormone receptor, alpha (THRA) var 1, (NM_199334) | NM_199334 |
| uc061imh.1 | THUMPD2 | THUMP domain containing 2 (THUMPD2) var 1, (NM_025264) | NM_025264 |
| uc061kij.1 | TIA1 | TIA1 cytotoxic granule-associated RNA binding protein (TIA1) var 2, (NM_022173) | NM_022173 |
| uc065cbs.1 | TKTL1 | transketolase-like 1 (TKTL1) var 3, (NM_001145934) | NM_001145934 |
| uc061cns.1 | TMC4, | transmembrane channel-like 4 (TMC4) var 2, (NM_144686), | NM_144686 |
| uc061dxx.1 | TMC4, | transmembrane channel-like 4 (TMC4) var 2, (NM_144686), | NM_144686 |
| uc061ehh.1 | TMC4, | transmembrane channel-like 4 (TMC4) var 2, (NM_144686), | NM_144686 |
| uc061fhz.1 | TMC4, | transmembrane channel-like 4 (TMC4) var 2, (NM_144686), | NM_144686 |
| uc063kgz.1 | TMED9 | transmembrane emp24 protein transport domain containing 9 (TMED9), (NM_017510) | NM_017510 |
| uc010wrg.2 | TMEM104 | transmembrane protein 104 (TMEM104), (NM_017728) | NM_017728 |
| uc064frq.1 | TMEM130 | transmembrane protein 130 (TMEM130) var 2, (NM_152913) | NM_152913 |
| uc060vxm.1 | TMEM161A | transmembrane protein 161A (TMEM161A) var 2, (NM_001256766) | NM_001256766 |
| uc002cze.3 | TMEM186 | transmembrane protein 186 (TMEM186), (NM_015421) | NM_015421 |
| uc058qzc.1 | TMEM19 | transmembrane protein 19 (TMEM19), (NM_018279) | NM_018279 |
| uc062biz.1 | TMEM191B | transmembrane protein 191B (TMEM191B), (NM_001242313) | NM_001242313 |
| uc062bjc.1 | TMEM191B | transmembrane protein 191B (TMEM191B), (NM_001242313) | NM_001242313 |
| uc058ssh.1 | TMEM263 | transmembrane protein 263 (TMEM263), (NM_152261) | NM_152261 |
| uc065anc.1 | TMS815B | thymosin beta 15B (TMSB15B), (NM_194324) | NM_194324 |
| uc064vgq.1 | TNC | tenascin C (TNC), (NM_002160) | NM_002160 |
| uc064ldp.1 | TNFRSF10A | tumor necrosis factor receptor superfamily, member 10a (TNFRSF10A), (NM_003844) | NM_003844 |
| uc060aoh.1 | TNK1 | tyrosine kinase, non-receptor, 1 (TNK1) var 2, (NM_003985) | NM_003985 |
| uc059sfs.1 | TNRC6A | trinucleotide repeat containing 6A (TNRC6A), (NM_014494) | NM_014494 |
| uc058wug.1 | TPT1 | tumor protein, translationally-controlled 1 (TPT1) var 2, (NM_003295) | NM_003295 |
| uc010fgc.4 | TRABD2A | TraB domain containing 2A (TRABD2A) var 1, (NM_001277053) | NM_001277053 |
| uc057pch.1 | TRAF3IP3 | TRAF3 interacting protein 3 (TRAF3IP3) var 2, (NM_001287754) | NM_001287754 |
| uc060dem.1 | TRAF4 | TNF receptor-associated factor 4 (TRAF4), (NM_004295) | NM_004295 |
| uc062inh.1 | TRAK1 | trafficking protein, kinesin binding 1 (TRAK1) var 5, (NM_001265610) | NM_001265610 |
| uc059qbf.1 | TRAP1 | TNF receptor-associated protein 1 (TRAP1) var 2, (NM_001272049) | NM_001272049 |
| uc011ekt.3 | TRIM26, | tripartite motif containing 26 (TRIM26) var 1, (NM_003449), | NM_003449 |
| uc011exk.3 | TRIM26, | tripartite motif containing 26 (TRIM26) var 1, (NM_003449), | NM_003449 |
| uc011fvx.3 | TRIM26, | tripartite motif containing 26 (TRIM26) var 1, (NM_003449), | NM_003449 |
| uc011hlj.2 | TRIM26, | tripartite motif containing 26 (TRIM26) var 2, (NM_001242783), | NM_001242783 |
| uc011ihz.3 | TRIM26, | tripartite motif containing 26 (TRIM26) var 1, (NM_003449), | NM_003449 |
| uc061dud.1 | TRIM28 | tripartite motif containing 28 (TRIM28), (NM_005762) | NM_005762 |
| uc061duf.1 | TRIM28 | tripartite motif containing 28 (TRIM28), (NM_005762) | NM_005762 |
| uc011ekk.2 | TRIM31, | tripartite motif containing 31 (TRIM31), (NM_007028), | NM_007028 |
| uc002anm.3 | TRIP4 | thyroid hormone receptor interactor 4 (TRIP4), (NM_016213) | NM_016213 |
| uc064giq.1 | TRIP6 | thyroid hormone receptor interactor 6 (TRIP6), (NM_003302) | NM_003302 |
| uc062bqp.1 | TRMT2A | tRNA methyltransferase 2 homolog A (*S. cerevisiae*) (TRMT2A) var 2, (NM_182984) | NM_182984 |
| uc003gli.1 | TRMT44 | tRNA methyltransferase 44 homolog (*S. cerevisiae*) (TRMT44), (NM_152544) | NM_152544 |
| uc062vbu.1 | TRMT44 | tRNA methyltransferase 44 homolog (*S. cerevisiae*) (TRMT44), (NM_152544) | NM_152544 |
| uc059pfx.1 | TSC2 | tuberous sclerosis 2 (TSC2) var 4, (NM_001077183) | NM_001077183 |
| uc065api.1 | TSC22D3 | TSC22 domain family, member 3 (TSC22D3) var 1, (NM_198057) | NM_198057 |
| uc058qdb.1 | TSFM | Ts translation elongation factor, mitochondrial (TSFM) var 4, (NM_001172697) | NM_001172697 |
| uc058qdg.1 | TSFM | Ts translation elongation factor, mitochondrial (TSFM) var 4, (NM_001172697) | NM_001172697 |
| uc058qdh.1 | TSFM | Ts translation elongation factor, mitochondrial (TSFM) var 2, (NM_005726) | NM_005726 |
| uc061nme.1 | TSN | translin (TSN) var 1, (NM_004622) | NM_004622 |

TABLE 9-continued

| GeneName | Symbol | Description | RefSeq |
|---|---|---|---|
| uc057gla.1 | TTC39A | tetratricopeptide repeat domain 39A (TTC39A) var 3, (NM_001297662) | NM_001297662 |
| uc064ebm.1 | TYW1 | tRNA-yW synthesizing protein 1 homolog (*S. cerevisiae*) (TYW1), (NM_018264) | NM_018264 |
| uc064sra.1 | UBAP2 | ubiquitin associated protein 2 (UBAP2) var 1, (NM_018449) | NM_018449 |
| uc010gpe.4 | UBASH3A | ubiquitin associated and SH3 domain containing A (UBASH3A) var 3, (NM_001243467) | NM_001243467 |
| uc062atf.1 | UBE2G2 | ubiquitin-conjugating enzyme E2G 2 (UBE2G2) var 1, (NM_003343) | NM_003343 |
| uc064jrw.1 | UBE3C | ubiquitin protein ligase E3C (UBE3C), (NM_014671) | NM_014671 |
| uc062sbi.1 | UBXN7 | UBX domain protein 7 (UBXN7), (NM_015562) | NM_015562 |
| uc060xan.1 | USF2 | upstream transcription factor 2, c-fos interacting (USF2) var 1, (NM_003367) | NM_003367 |
| uc058fwv.1 | USP35 | ubiquitin specific peptidase 35 (USP35), (NM_020798) | NM_020798 |
| uc060kwg.1 | USP36 | ubiquitin specific peptidase 36 (USP36), (NM_025090) | NM_025090 |
| uc061lir.1 | USP39 | ubiquitin specific peptidase 39 (USP39) var 2, (NM_001256725) | NM_001256725 |
| uc061liu.1 | USP39 | ubiquitin specific peptidase 39 (USP39) var 2, (NM_001256725) | NM_001256725 |
| uc063nhu.1 | VARS, | valyl-tRNA synthetase (VARS), (NM_006295), | NM_006295 |
| uc063tkn.1 | VARS, | valyl-tRNA synthetase (VARS), (NM_006295), | NM_006295 |
| uc063uje.1 | VARS, | valyl-tRNA synthetase (VARS), (NM_006295), | NM_006295 |
| uc063vop.1 | VARS, | valyl-tRNA synthetase (VARS), (NM_006295), | NM_006295 |
| uc063xtp.1 | VARS, | valyl-tRNA synthetase (VARS), (NM_006295), | NM_006295 |
| uc064adp.1 | VARS, | valyl-tRNA synthetase (VARS), (NM_006295), | NM_006295 |
| uc064adt.1 | VARS, | valyl-tRNA synthetase (VARS), (NM_006295), | NM_006295 |
| uc001xss.4 | VASH1 | vasohibin 1 (VASH1), (NM_014909) | NM_014909 |
| uc001xst.3 | VASH1 | vasohibin 1 (VASH1), (NM_014909) | NM_014909 |
| uc064dtc.1 | IVOPP1 | vesicular, overexpressed in cancer, prosurvival protein 1 (VOPP1) var 3, (NM_001284283) | NM_001284283 |
| uc001ucd.4 | VPS33A | vacuolar protein sorting 33 homolog A (*S. cerevisiae*) (VPS33A), (NM_022916) | NM_022916 |
| uc058del.1 | VPS51 | vacuolar protein sorting 51 homolog (*S. cerevisiae*) (VPS51) var 1, (NM_013265) | NM_013265 |
| uc058deo.1 | VPS51 | vacuolar protein sorting 51 homolog (*S. cerevisiae*) (VPS51) var 1, (NM_013265) | NM_013265 |
| uc058dep.1 | VPS51 | vacuolar protein sorting 51 homolog (*S. cerevisiae*) (VPS51) var 1, (NM_013265) | NM_013265 |
| uc058des.1 | VPS51 | vacuolar protein sorting 51 homolog (*S. cerevisiae*) (VPS51) var 1, (NM_013265) | NM_013265 |
| uc064boy.1 | VWDE | von Willebrand factor D and EGF domains (VWDE), (NM_001135924) | NM_001135924 |
| uc059fdw.1 | WARS | tryptophanyl-tRNA synthetase (WARS) var 2, (NM_173701) | NM_173701 |
| uc064ecw.1 | WBSCR17 | Williams-Beuren syndrome chromosome region 17 (WBSCR17), (NM_022479) | NM_022479 |
| uc062vec.1 | WDR1 | WD repeat domain 1 (WDR1) var 2, (NM_005112) | NM_005112 |
| uc002tpg.3 | WDR33 | WD repeat domain 33 (WDR33) var 1, (NM_018383) | NM_018383 |
| uc057ixb.1 | WDR47 | WD repeat domain 47 (WDR47) var 3, (NM_001142551) | NM_001142551 |
| uc061kuu.1 | WDR54 | WD repeat domain 54 (WDR54), (NM_032118) | NM_032118 |
| uc059xdl.1 | WDR59 | WD repeat domain 59 (WDR59), (NM_030581) | NM_030581 |
| uc060plz.1 | WDR7 | WD repeat domain 7 (WDR7) var 2, (NM_052834) | NM_052834 |
| uc059zix.1 | WDR81, AC206360.1, | WD repeat domain 81 (WDR81) var 3, (NM_001163673), | NM_001163673 |
| uc064igt.1 | WDR91 | WD repeat domain 91 (WDR91), (NM_014149) | NM_014149 |
| uc064iqz.1 | WEE2, | WEE1 homolog 2 (S. pombe) (WEE2), (NM_001105558), | NM_001105558 |
| uc064juc.1 | WEE2, | WEE1 homolog 2 (S. pombe) (WEE2), (NM_001105558), | NM_001105558 |
| uc062unn.1 | WHSC1 | Wolf-Hirschhorn syndrome candidate 1 (WHSC1) var 3, (NM_133335) | NM_133335 |
| uc057bqa.1 | WRAP73 | WD repeat containing, antisense to TP73 (WRAP73), (NM_017818) | NM_017818 |
| uc064oeq.1 | WWP1 | WW domain containing E3 ubiquitin protein ligase 1 (WWP1), (NM_007013) | NM_007013 |
| uc057vxg.1 | XPNPEP1 | X-prolyl aminopeptidase (aminopeptidase P) 1, soluble (XPNPEP1) var 2, (NM_001167604) | NM_001167604 |
| uc060zlu.1 | XRCC1 | X-ray repair complementing defective repair in Chinese hamster cells 1 (XRCC1), (NM_006297) | NM_006297 |
| uc058fld.1 | XRRA1 | X-ray radiation resistance associated 1 (XRRA1) var 2, (NM_001270380) | NM_001270380 |
| uc060mzy.1 | ZBTB14 | zinc finger and BTB domain containing 14 (ZBTB14) var 2, (NM_001243704) | NM_001243704 |
| uc059qwq.1 | ZC3H7A | zinc finger CCCH-type containing 7A (ZC3H7A), (NM_014153) | NM_014153 |
| uc060pua.1 | ZCCHC2 | zinc finger, CCHC domain containing 2 (ZCCHC2) var 1, (NM_017742) | NM_017742 |
| uc063ezp.1 | ZCCHC9 | zinc finger, CCHC domain containing 9 (ZCCHC9) var 2, (NM_001131035) | NM_001131035 |
| uc001knl.5 | ZDHHC16 | zinc finger, DHHC-type containing 16 (ZDHHC16) var 2, (NM_198043) | NM_198043 |
| uc001knm.5 | ZDHHC16 | zinc finger, DHHC-type containing 16 (ZDHHC16) var 4, (NM_198045) | NM_198045 |
| uc001knn.5 | ZDHHC16 | zinc finger, DHHC-type containing 16 (ZDHHC16) var 3, (NM_198044) | NM_198044 |
| uc057vfd.1 | ZDHHC16 | zinc finger, DHHC-type containing 16 (ZDHHC16) var 7, (NM_001287804) | NM_001287804 |
| uc062brj.1 | ZDHHC8 | zinc finger, DHHC-type containing 8 (ZDHHC8) var 1, (NM_001185024) | NM_001185024 |
| uc057sot.1 | ZEB1 | zinc finger E-box binding homeobox 1 (ZEB1) var 9, (NM_001174096) | NM_001174096 |
| uc063moe.1 | ZFP57, | ZFP57 zinc finger protein (ZFP57), (NM_001109809), | NM_001109809 |
| uc063uya.1 | ZFP57, | ZFP57 zinc finger protein (ZFP57), (NM_001109809), | NM_001109809 |
| uc063wdn.1 | ZFP57, | ZFP57 zinc finger protein (ZFP57), (NM_001109809), | NM_001109809 |
| uc063xdl.1 | ZFP57, | ZFP57 zinc finger protein (ZFP57), (NM_001109809), | NM_001109809 |
| uc063yiu.1 | ZFP57, | ZFP57 zinc finger protein (ZFP57), (NM_001109809), | NM_001109809 |
| uc063zol.1 | ZFP57, | ZFP57 zinc finger protein (ZFP57), (NM_001109809), | NM_001109809 |
| uc059ygx.1 | ZFPM1 | zinc finger protein, FOG family member 1 (ZFPM1), (NM_153813) | NM_153813 |
| uc064pkv.1 | ZFPM2 | zinc finger protein, FOG family member 2 (ZFPM2), (NM_012082) | NM_012082 |
| uc010qpb.3 | ZFYVE27 | zinc finger, FYVE domain containing 27 (ZFYVE27) var 6, (NM_001174121) | NM_001174121 |
| uc010qpd.3 | ZFYVE27 | zinc finger, FYVE domain containing 27 (ZFYVE27) var 4, (NM_001174119) | NM_001174119 |
| uc061you.1 | ZGPAT | zinc finger, CCCH-type with G patch domain (ZGPAT) var 3, (NM_181485) | NM_181485 |
| uc057rdg.1 | ZMYND11 | zinc finger, MYND-type containing 11 (ZMYND11) var 1, (NM_006624) | NM_006624 |
| uc060tya.1 | ZNF136 | zinc finger protein 136 (ZNF136), (NM_003437) | NM_003437 |
| uc004aum.2 | ZNF169 | zinc finger protein 169 (ZNF169) var 2, (NM_194320) | NM_194320 |
| uc060wwz.1 | ZNF181 | zinc finger protein 181 (ZNF181) var 2, (NM_001145665) | NM_001145665 |
| uc057ybl.1 | ZNF195 | zinc finger protein 195 (ZNF195) var 2, (NM_001130519) | NM_001130519 |
| uc060zpk.1 | ZNF222 | zinc finger protein 222 (ZNF222) var 1, (NM_001129996) | NM_001129996 |
| uc010tbw.3 | ZNF268 | zinc finger protein 268 (ZNF268) var 5, (NM_001165883) | NM_001165883 |
| uc060boo.1 | ZNF286A | TBC1 domain family, member 26 (TBC1D26), (NM_178571) | NM_178571 |
| uc060bos.1 | ZNF286A | TBC1 domain family, member 26 (TBC1D26), (NM_178571) | NM_178571 |
| uc064fyo.1 | ZNF3 | zinc finger protein 3 (ZNF3) var 1, (NM_017715) | NM_017715 |

TABLE 9-continued

| GeneName | Symbol | Description | RefSeq |
|---|---|---|---|
| uc002nvr.3 | ZNF302 | zinc finger protein 302 (ZNF302) var 3, (NM_001289181) | NM_001289181 |
| uc003mjj.4 | ZNF354A | zinc finger protein 354A (ZNF354A), (NM_005649) | NM_005649 |
| uc060xsx.1 | ZNF383 | zinc finger protein 383 (ZNF383), (NM_152604) | NM_152604 |
| uc064lnx.1 | ZNF395 | zinc finger protein 395 (ZNF395), (NM_018660) | NM_018660 |
| uc060ols.1 | ZNF396 | zinc finger protein 396 (ZNF396), (NM_145756) | NM_145756 |
| uc063pfu.1 | ZNF451 | zinc finger protein 451 (ZNF451) var 2, (NM_015555) | NM_015555 |
| uc061bot.1 | ZNF473 | zinc finger protein 473 (ZNF473) var 1, (NM_015428) | NM_015428 |
| uc001ico.4 | ZNF496 | zinc finger protein 496 (ZNF496), (NM_032752) | NM_032752 |
| uc057rac.1 | ZNF496 | zinc finger protein 496 (ZNF496), (NM_032752) | NM_032752 |
| uc002mtq.3 | ZNF563 | zinc finger protein 563 (ZNF563), (NM_145276) | NM_145276 |
| uc060tza.1 | ZNF564 | zinc finger protein 564 (ZNF564), (NM_144976) | NM_144976 |
| uc060xvz.1 | ZNF571 | zinc finger protein 571 (ZNF571) var 2, (NM_016536) | NM_016536 |
| uc060zmo.1 | ZNF576 | zinc finger protein 576 (ZNF576) var 2, (NM_001145347) | NM_001145347 |
| uc061dnb.1 | ZNF586 | zinc finger protein 586 (ZNF586) var 2, (NM_001077426) | NM_001077426 |
| uc061dnf.1 | ZNF587 | zinc finger protein 587 (ZNF587) var 1, (NM_032828) | NM_032828 |
| uc061dng.1 | ZNF587 | zinc finger protein 587 (ZNF587) var 2, (NM_001204817) | NM_001204817 |
| uc061dnh.1 | ZNF587 | zinc finger protein 587 (ZNF587) var 2, (NM_001204817) | NM_001204817 |
| uc061dni.1 | ZNF587 | zinc finger protein 587 (ZNF587) var 2, (NM_001204817) | NM_001204817 |
| uc060weu.1 | ZNF626 | zinc finger protein 626 (ZNF626) var 2, (NM_145297) | NM_145297 |
| uc061bzw.1 | ZNF649 | zinc finger protein 649 (ZNF649), (NM_023074) | NM_023074 |
| uc062isr.1 | ZNF662 | zinc finger protein 662 (ZNF662) var 1, (NM_207404) | NM_207404 |
| uc059tkg.1 | ZNF668 | zinc finger protein 668 (ZNF668) var 2, (NM_024706) | NM_024706 |
| uc057fla.1 | ZNF691 | zinc finger protein 691 (ZNF691) var 1, (NM_001242739) | NM_001242739 |
| uc064rdd.1 | ZNF707 | zinc finger protein 707 (ZNF707) var 3, (NM_001100599) | NM_001100599 |
| uc064rdq.1 | ZNF707 | zinc finger protein 707 (ZNF707) var 6, (NM_001288807) | NM_001288807 |
| uc011kuo.3 | ZNF783 | zinc finger family member 783 (ZNF783), (NM_001195220) | NM_001195220 |
| uc003wfi.3 | ZNF786 | zinc finger protein 786 (ZNF786), (NM_152411) | NM_152411 |
| uc060tys.1 | ZNF799 | zinc finger protein 799 (ZNF799), (NM_001080821) | NM_001080821 |
| uc010ygn.3 | ZNF835 | zinc finger protein 835 (ZNF835), (NM_001005850) | NM_001005850 |
| uc061cbj.1 | ZNF841 | zinc finger protein 841 (ZNF841), (NM_001136499) | NM_001136499 |
| uc062iuy.1 | ZNF852 | zinc finger protein 852 (ZNF852), (NM_001287349) | NM_001287349 |
| uc062iuz.1 | ZNF852 | zinc finger protein 852 (ZNF852), (NM_001287349) | NM_001287349 |
| uc002bkr.4 | ZSCAN2 | zinc finger and SCAN domain containing 2 (ZSCAN2) var 1, (NM_181877) | NM_181877 |
| uc059mrx.1 | ZSCAN2 | zinc finger and SCAN domain containing 2 (ZSCAN2) var 1, (NM_181877) | NM_181877 |
| uc059mry.1 | ZSCAN2 | zinc finger and SCAN domain containing 2 (ZSCAN2) var 1, (NM_181877) | NM_181877 |
| uc059mrz.1 | ZSCAN2 | zinc finger and SCAN domain containing 2 (ZSCAN2) var 1, (NM_181877) | NM_181877 |
| uc059msa.1 | ZSCAN2 | zinc finger and SCAN domain containing 2 (ZSCAN2) var 1, (NM_181877) | NM_181877 |
| uc064fvy.1 | ZSCAN25 | zinc finger and SCAN domain containing 25 (ZSCAN25), (NM_145115) | NM_145115 |
| uc032wpp.2 | ZSCAN26 | zinc finger and SCAN domain containing 26 (ZSCAN26) var d, (NM_001287421) | NM_001287421 |
| uc032wpq.2 | ZSCAN26 | zinc finger and SCAN domain containing 26 (ZSCAN26) var a, (NM_001023560) | NM_001023560 |
| uc010uwx.4 | ZSCAN32 | zinc finger and SCAN domain containing 32 (ZSCAN32) var 4, (NM_001284529) | NM_001284529 |
| uc059pye.1 | ZSCAN32 | zinc finger and SCAN domain containing 32 (ZSCAN32) var 3, (NM_001284528) | NM_001284528 |

TABLE 10

| GeneName | Symbol | Description | GenBank | RefSeq |
|---|---|---|---|---|
| uc002yun.1 | AML1 | AML1 mRNA | X90981 | NM_001122607 |
| uc001psq.3 | CD3E | CD3E antigen, epsilon polypeptide precursor | NM_000733 | NM_000733 |
| uc009zez.1 | CD4 | T-cell surface glycoprotein CD4 precursor. | AK310652 | NM_000616 |
| uc009zfa.1 | CD4 | T-cell surface glycoprotein CD4 precursor. | AK310687 | NM_000616 |
| uc009zfb.1 | CD4 | T-cell surface glycoprotein CD4 precursor. | AK311495 | NM_000616 |
| uc001qqv.1 | CD4 | CD4 antigen precursor | NM_000616 | NM_000616 |
| uc010sfj.1 | CD4 | CD4 antigen precursor | AK316461 | NM_000616 |
| uc009zfc.1 | CD4 | T-cell surface glycoprotein CD4; | AK315898 | NM_000616 |
| uc010sfk.1 | CD4 | T-cell surface glycoprotein CD4; | AK300052 | NM_000616 |
| uc010sfl.1 | CD4 | T-cell surface glycoprotein CD4; | AK316462 | NM_000616 |
| uc010sfm.1 | CD4 | T-cell surface glycoprotein CD4; | AK303968 | NM_000616 |
| uc010sbs.1 | ETS1 | v-ets erythroblastosis virus E26 oncogene | NM_005238 | NM_005238 |
| uc009zch.2 | ETS1 | v-ets erythroblastosis virus E26 oncogene | NM_001162422 | NM_001162422 |
| uc009zcg.2 | ETS1 | ETS1 protein; V-ets erythroblastosis virus E26 oncogene homolog 1 CRA_a; | BC017314 | NM_005238 |
| uc001qej.2 | ETS1 | v-ets erythroblastosis virus E26 oncogene | NM_001143820 | NM_001143820 |
| uc001qej.2 | ETS1 | v-ets erythroblastosis virus E26 oncogene | NM_001143820 | NM_001143820 |
| uc011mnb.1 | FOXP3 | forkhead box P3 isoform a | BC143786 | NM_014009 |
| uc004dnf.3 | FOXP3 | forkhead box P3 isoform a | NM_014009 | NM_014009 |
| uc004dne.3 | FOXP3 | forkhead box P3 isoform b | NM_001114377 | NM_001114377 |
| uc010niq.1 | FOXP3 | forkhead box P3 isoform b | AJ005891 | NM_001114377 |
| uc058pgk.1 | IKZF4 | IKAROS family zinc finger 4 (Eos) (IKZF4), mRNA. (from RefSeq NM_022465) | NM_022465 | |
| uc001iiz.1 | IL2RA | interleukin 2 receptor, alpha chain precursor | NM_000417 | NM_000417 |
| uc009xih.1 | IL2RA | Interleukin 2 receptor, alpha; isoform CRA_b; | K03122 | NM_000417 |
| uc001ija.1 | IL2RA | Interleukin 2 receptor, alpha; Interleukin-2 receptor | AF008556 | NM_000417 |
| uc003aqv.1 | IL2RB | interleukin 2 receptor beta precursor | NM_000878 | NM_000878 |

TABLE 10-continued

| GeneName | Symbol | Description | GenBank | RefSeq |
|---|---|---|---|---|
| uc004dyv.1 | IL2RG | IL2RG nirs variant 4; | AB102796 | NM_000206 |
| uc004dyw.1 | IL2RG | interleukin 2 receptor, gamma precursor | NM_000206 | NM_000206 |
| uc004dyx.1 | IL2RG | IL2RG nirs variant 2; | AB102794 | NM_000206 |
| uc002yuh.2 | RUNX1 | runt-related transcription factor 1 isoform | NM_001001890 | NM_001001890 |
| uc002yui.2 | RUNX1 | runt-related transcription factor 1 isoform | CR622321 | NM_001001890 |
| uc010gmu.2 | RUNX1 | runt-related transcription factor 1 isoform | BC136380 | NM_001754 |
| uc010gmv.2 | RUNX1 | runt-related transcription factor 1 isoform | NM_001754 | NM_001754 |
| uc002yuj.3 | RUNX1 | runt-related transcription factor 1 isoform | D89790 | NM_001754 |
| uc002yuk.3 | RUNX1 | runt-related transcription factor 1 isoform | AK226159 | NM_001754 |
| uc002yul.1 | RUNX1 | RUNX1 gene for runt-related transcription factor 1 | AY509915 | NM_001754 |
| uc002yum.1 | RUNX1 | RUNX1 gene for runt-related transcription factor 1 | AY509916 | NM_001754 |
| uc002yuo.1 | RUNX1 | runt-related transcription factor 1 | NM_001122607 | NM_001122607 |
| uc057qye.1 | SMYD3 | SET and MYND domain containing 3 (SMYD3),var2, (from RefSeq NM_022743) | NM_022743 | |
| uc002sye.1 | ZAP70 | zeta-chain associated protein kinase 70 kDa | BC039039 | NM_001079 |

TABLE 11

| GeneName | Symbol | Description | RefSeq |
|---|---|---|---|
| uc010ugx.2 | AQP9 | aquaporin 9 (AQP9), mRNA. (from RefSeq NM_020980) | NM_020980 |
| uc010rva.2 | CASP5 | caspase 5, apoptosis-related cysteine peptidase (CASP5) | NM_004347 |
| uc001pss.2 | CD3D | CD3d molecule, delta (CD3-TCR complex) (CD3D) | NM_000732 |
| uc001quo.2 | CLEC4E | C-type lectin domain family 4, member E (CLEC4E | NM_014358 |
| uc061sid.1 | CXCR2 | chemokine (C-X-C motif) receptor 2 | NM_001168298 |
| uc002tbx.4 | IL18RAP | interleukin 18 receptor accessory protein (IL18RAP) | NM_003853 |
| uc001ovc.4 | KCNE3 | potassium channel, voltage gated subfamily E regulatory beta subunit 3 (KCNE3) | NM_005472 |
| uc001qye.4 | KLRC4 | killer cell lectin-like receptor subfamily C, member 4 (KLRC4) | NM_013431 |
| uc003apy.5 | NCF4, | neutrophil cytosolic factor 4, 40 kDa (NCF4), | NM_000631 |
| uc002qkv.4 | RPL28 | ribosomal protein L28 (RPL28) | NM_000991 |
| uc001fbr.2 | S100A12 | S100 calcium binding protein A12 (S100A12) | NM_005621 |
| uc001fbs.3 | S100A8 | S100 calcium binding protein A8 (S100A8) | NM_002964 |
| uc001fwq.5 | SLAMF7 | SLAM family member 7 (SLAMF7) | NM_021181 |
| uc004bjz.5 | TLR4 | toll-like receptor 4 (TLR4) | NM_138554 |
| uc002jup.3 | TMC8 | transmembrane channel-like 8 (TMC8) | NM_152468 |
| uc002txk.3 | TNFAIP6 | tumor necrosis factor, alpha-induced protein 6 (TNFAIP6) | NM_007115 |
| uc003xcy.4 | TNFRSF10C | tumor necrosis factor receptor superfamily, member 10c, | NM_003841 |

What is claimed is:

1. A method of treatment comprising:
(a) obtaining a blood sample from a human subject, wherein the blood sample is stabilized in a guanidinium denaturant;
(b) extracting RNA from the blood sample;
(c) measuring RNA expression levels for a plurality of RNA transcripts, wherein the plurality of RNA transcripts comprises RNA transcripts selected from DGKA, DLG1, ICOSLG, IKZF4/Eos, SMYD3, TCF3, TRIM28, and any combination of any of the foregoing, wherein the expression levels of each of the plurality of RNA transcripts are determined as a percentage of mean expression for each RNA transcript and normalized to calculate a cumulative score for the plurality of RNA transcripts;
(d) comparing the cumulative score to those of a reference set of values derived from patients without coronary artery disease;
(e) identifying the human subject having coronary artery disease based on the comparison performed in step (d) when the cumulative score of the human subject meets or exceeds a threshold fold change compared to that for patients without coronary artery disease, the threshold fold change set at a value of at least 1.5; and
(f) treating the human subject who tests positive for coronary artery disease with administration of a therapeutically effective amount of a medicament comprised of one or more of a statin, an aspirin, an angiotensin-converting enzyme inhibitor, a diuretic, a glucose control medication, a beta blocker, a salt of any of these, or any combination thereof.

2. The method of treatment of claim 1, wherein the blood sample comprises whole blood.

3. The method of treatment of claim 1, further comprising depleting ribosomal RNA from the extracted RNA prior to measuring RNA expression levels.

4. The method of treatment of claim 3, wherein depleting ribosomal RNA from the extracted RNA comprises treating the RNA with probes that are specific for ribosomal RNA.

5. The method of treatment of claim 1, wherein the measuring of RNA expression levels comprises measuring individual RNA expression levels of the plurality of RNA transcripts or cDNA transcripts thereof.

6. The method of treatment of claim 1, wherein the extracted RNA from the blood sample is stabilized with a non-cationic detergent.

7. The method of treatment of claim 1, further comprising performing a coronary imaging technique.

8. The method of treatment of claim 1, further comprising selecting the human subject that has been identified as having one or more risk factors for coronary artery disease prior to obtaining the blood sample from the human subject.

9. The method of treatment of claim 1, wherein the lifestyle changes are comprised of one or more of weight loss, smoking cessation, dietary changes, reducing stress, and increased exercise.

10. A method of treatment comprising:
(a) obtaining a blood sample from a human subject;
(b) extracting RNA from said blood sample;
(c) determining expression levels of a plurality of RNA transcripts in the blood sample using a technique other than microarray, wherein the plurality of RNA transcripts comprises RNA transcripts selected from DGKA, DLG1, ICOSLG, IKZF4/Eos, SMYD3, TCF3, TRIM28, and any combination of any of the foregoing, wherein the expression levels of each of the plurality of RNA transcripts are determined as a percentage of mean expression for each RNA transcript and normalized to calculate a cumulative score for the plurality of RNA transcripts;
(d) identifying the human subject having coronary artery disease based on the cumulative score determined in step (c) and a reference set of values derived from patients without coronary artery disease when the cumulative score of the human subject meets or exceeds a threshold fold change compared to that for patients without coronary artery disease, the threshold fold change set at a value of at least 1.5; and
(e) treating the human subject who tests positive for coronary artery disease with (i) lifestyle changes, (ii) a therapeutically effective amount of a medicament comprised of one or more of a statin, an aspirin, an angiotensin-converting enzyme inhibitor, a diuretic, a glucose control medication, a beta blocker, a salt of any of these, or any combination thereof, or (iii) both.

11. The method of treatment of claim 10, further comprising depleting ribosomal RNA from the extracted RNA prior to measuring RNA expression levels.

12. The method of treatment of claim 11, wherein depleting ribosomal RNA from the extracted RNA comprises treating the RNA with probes that are specific for ribosomal RNA.

13. The method of treatment of claim 10, wherein the measuring of RNA expression levels comprises measuring individual RNA expression levels of the plurality of RNA transcripts or cDNA transcripts thereof.

14. The method of treatment of claim 10, wherein the extracted RNA from the blood sample is stabilized with a non-cationic detergent.

15. The method of treatment of claim 10, further comprising performing a coronary imaging technique.

16. The method of treatment of claim 10, further comprising selecting the human subject that has been identified as having one or more risk factors for coronary artery disease prior to obtaining the blood sample from the human subject.

17. A method of treatment comprising treating a human subject who tests positive for coronary artery disease a therapeutically effective amount of a medicament comprised of one or more of a statin, an aspirin, an angiotensin-converting enzyme inhibitor, a diuretic, a glucose control medication, a beta blocker, a salt of any of these, or any combination thereof, wherein the human subject is tested for coronary artery disease by:
(a) obtaining a blood sample from the human subject;
(b) extracting RNA from said blood sample;
(c) measuring RNA expression levels for a plurality of RNA transcripts in the blood sample using a technique other than microarray, wherein the plurality of RNA transcripts comprises RNA transcripts selected from DGKA, DLG1, ICOSLG, IKZF4/Eos, SMYD3, TCF3, TRIM28, and any combination of any of the foregoing;
(d) comparing the RNA expression levels to those of a reference set of values derived from patients without coronary artery disease; and
(e) identifying the human subject having coronary artery disease based on the comparison performed in step (d) when the cumulative score of the human subject meets or exceeds a threshold fold change compared to that for patients without coronary artery disease, the threshold fold change set at a value of at least 1.5.

* * * * *

UNITED STATES PATENT AND TRADEMARK OFFICE
CERTIFICATE OF CORRECTION

Page 1 of 1

PATENT NO. : 12,104,210 B2
APPLICATION NO. : 17/498417
DATED : October 1, 2024
INVENTOR(S) : Timothy A. McCaffrey et al.

It is certified that error appears in the above-identified patent and that said Letters Patent is hereby corrected as shown below:

In the Claims

Claim 17, Column 82, Line 14, after "disease" insert --with--.

Signed and Sealed this
Twenty-fifth Day of March, 2025

Coke Morgan Stewart
*Acting Director of the United States Patent and Trademark Office*